US008063220B2

(12) United States Patent
Galambos et al.

(10) Patent No.: US 8,063,220 B2
(45) Date of Patent: *Nov. 22, 2011

(54) SULFONYL-QUINOLINE DERIVATIVES

(75) Inventors: Janos Galambos, Budapest (HU); Gyorgy Keseru, Telki (HU); Krisztina Gal, Budapest (HU); Monika Vastag, Budapest (HU); Amrita Agnes Bobok, Budapest (HU); Csaba Weber, Budapest (HU); Ibolya Prauda, Budapest (HU); Gabor Wagner, Budapest (HU)

(73) Assignee: Richter Gedeon Nyrt., Budapest (HU)

( * ) Notice: Subject to any disclaimer, the term of this patent is extended or adjusted under 35 U.S.C. 154(b) by 591 days.

This patent is subject to a terminal disclaimer.

(21) Appl. No.: 12/144,490

(22) Filed: Jun. 23, 2008

(65) Prior Publication Data

US 2009/0042934 A1 Feb. 12, 2009

Related U.S. Application Data

(63) Continuation of application No. PCT/HU2008/000068, filed on Jun. 17, 2008.

(60) Provisional application No. 60/945,628, filed on Jun. 22, 2007.

(51) Int. Cl.
*A61K 31/47* (2006.01)
*A61P 25/00* (2006.01)
*C07D 215/36* (2006.01)

(52) U.S. Cl. ...................... 546/153; 514/312
(58) Field of Classification Search .............. None
See application file for complete search history.

(56) References Cited

U.S. PATENT DOCUMENTS

2006/0276469 A1* 12/2006 Malherbe et al. ......... 514/232.5
2009/0270371 A1* 10/2009 Keseru et al. ............. 514/217.07

FOREIGN PATENT DOCUMENTS

| WO | WO 2005/030129 | 4/2005 |
| WO | WO 2005/058834 | 6/2005 |
| WO | WO 2005/070890 | 8/2005 |
| WO | WO 2006/120573 | 11/2006 |

OTHER PUBLICATIONS

Vippagunta et al., "Crystalline Solids", 48 Adv. Drug Delivery Rev. 3-26 (2001).*
Martin, Yvonne C. et al., Do Structurally Similar Molecules Have Similar Biological Activity?, 45 J. Med. Chem., 4350-4358, 4536 (2002).*
Zhang et al., Structure-Activity Relationship in a Novel Series of 7-Substituted-Aryl Quinolines and 5-substituted-aryl Benzothiazoles at the Metabotropic Glutamate Receptor Subtype 5, 18 Bioorg. & Med. Chem. Letts., 3026-3035 (2010).*
Aiba et al., "Deficient cerebellar long-term depression and impaired motor learning in mGluR1 mutant mice," Cell, 1994, 79:377-388.
Aiba et al., "Reduced hippocampal long-term potentiation and context-specific deficit in associative learning in mGluR1 mutant mice," Cell, 1994, 79(2):365-375.
Bashir et al., "Induction of LTP in the hippocampus needs synaptic activation of glutamate metabotropic receptors," Nature, 1993, 363:347-350.
Batra and Shea, "Novel trifunctional building blocks for fluorescent polymers," Org. Lett., 2003, 5(21):3895-3898.
Birch et al., "Syntheses of flosequinan: a novel 4-quinolone shown to be useful in congestive heart failure," J. Chem. Soc., Perkin Trans. 1, 1994, 387-392.
Bordi and Ugolini, "Group I metabotropic glutamate receptors: implications for brain diseases," Progress in Neurobiology, 1999, 59:55-79.
Bordi and Ugolini, "Involvement of mGluR5 on acute nociceptive transmission," Brain Res., 2000, 871:223-233.
Bortolotto et al., "A molecular switch activated by metabotropic glutamate receptors regulates induction of long-term potentiation," Nature, 1994, 368:740-743.
Cheng and Prusoff, "Relationship between the inhibition constant (K1) and the concentration of inhibitor which causes 50 per cent inhibition (I50) of an enzymatic reaction," Biochem. Pharmacol., 1973, 22:3099-3108.
Cunningham et al., "Excitatory amino acid receptors: a gallery of new targets for pharmacological intervention," Life Sci., 1994, 54:135-148.
Gasparini et al., "[3H]-M-MPEP, a potent, subtype-selective radioligand for the metabotropic glutamate receptor subtype 5," Bioorg. Med. Chem. Lett., 2002, 12:407-409.
Gasparini et al., "Allosteric modulators of group I metabotropic glutamate receptors: novel subtype-selective ligands and therapeutic perspectives," Curr. Opin. Pharmacol., 2002, 2:43-49.
Hollmann and Heinemann, "Cloned glutamate receptors," Annu. Rev. Neurosci., 1994, 17:31-108.
Johnson and Bunge, "Primary cell cultures of peripheral and central neurons and glia," Protocols for Neural Cell Culture, 1992, Fedoroff and Richardson (eds.), The Humana Press Inc., pp. 51-77.
Joly et al., "Molecular, functional, and pharmacological characterization of the metabotropic glutamate receptor type 5 splice variants: comparison with mGluR1," J. Neurosci., 1995, 15:3970-3981.
Knöpfel et al., "Metabotropic glutamate receptors: novel targets for drug development," J. Med. Chem., 1995, 38(9):1417-1426.
Lavreysen et al., "[3H]R214127: A Novel High-Affinity Radioligand for the mGlu1 Receptor Reveals a Common Binding Site Shared by Multiple Allosteric Antagonists," Mol..Pharm., 2003, 63(5):1082-1093.
Meller et al., "Acute mechanical hyperalgesia is produced by coactivation of AMPA and metabotropic glutamate receptors," Neuroreport, 1993, 4:879-882.
Minakami et al., "Molecular cloning and the functional expression of two isoforms of human metabotropic glutamate receptor subtype 5," BBRC, 1994, 199:1136-1143.

(Continued)

Primary Examiner — Janet Andres
Assistant Examiner — Timothy R Rozof
(74) Attorney, Agent, or Firm — Fish & Richardson P.C.

(57) ABSTRACT

The present invention relates to new mGluR1 and mGluR5 receptor subtype preferring ligands of formula (I) and/or salts and/or hydrates and/or solvates and/or polymorphs thereof. The invention also relates to processes and intermediates for their preparation, to pharmaceutical compositions containing these compounds and to their use in treatment and/or prevention of conditions which require modulation of mGluR1 and mGluR5 receptors.

17 Claims, No Drawings

OTHER PUBLICATIONS

Nakanishi, "Metabotropic glutamate receptors: synaptic transmission, modulation, and plasticity," *Neuron*, 1994, 13(5):1031-1037.

Neugebauer, "Metabotropic glutamate receptors—important modulators of nociception and pain behavior," *Pain*, 2002, 98:1-8.

Nishimura et al., "Conformational analysis of tandospirone in aqueous solution: lead evolution of potent dopamine D4 receptor ligands," *Bioorg. Med. Chem. Lett.*, 2001, 11(9):1141-1144.

Pin and Duvoisin, "The metabotropic glutamate receptors: Structure and functions," *Neuropharmacology*, 1995, 34:1-26.

Pin et al., "Alternative splicing generates metabotropic glutamate receptors inducing different patterns of calcium release in *Xenopus oocytes*," *PNAS*, 1992, 89:10331-10335.

Schoepp and Conn, "Metabotropic glutamate receptors in brain function pathology," *Trends Pharmacol. Sci.*, 1993, 14:13-20.

Schoepp, "Novel Functions for Subtypes of Metabotropic Glutamate Receptors," *Neurochem. Int.*, 1994, 24:439-449.

Slassi et al., "Recent advances in non-competitive mGlu5 receptor antagonists and their potential therapeutic applications," *Curr. Top. Med. Chem.*, 2005, 5(9):897-911.

Spooren et al., "Novel allosteric antagonists shed light on mGlu5 receptors and CNS disorders," *Trends Pharmacol. Sci.*, 2001, 22:331-337.

Tsou et al., "Optimization of 6,7-disubstituted-4-(arylamino)quinoline-3-carbonitriles as orally active, irreversible inhibitors of human epidermal growth factor receptor-2 kinase activity," *J. Med. Chem.*, 2005, 48(4):1107-1131.

* cited by examiner

US 8,063,220 B2

SULFONYL-QUINOLINE DERIVATIVES

CROSS REFERENCE TO RELATED APPLICATIONS

This application claims priority under 35 USC §120 to PCT/HU08/00068, filed Jun. 17, 2008, which claims priority to HU P07 00417 filed Jun. 18, 2007, and HU P08 00376 filed Jun. 12, 2008, and also claims priority under §119(e) to U.S. Provisional Patent Application No. 60/945,628 filed Jun. 22, 2007.

FIELD OF THE INVENTION

The present invention relates to new mGluR1 and mGluR5 receptor subtype preferring ligands of formula (I) and/or salts and/or hydrates and/or solvates and/or polymorphs thereof. The invention also relates to processes and intermediates for their preparation, to pharmaceutical compositions containing these compounds and to their use in treatment and/or prevention of conditions which require modulation of mGluR1 and mGluR5 receptors.

BACKGROUND OF THE INVENTION

A major excitatory neurotransmitter in the mammalian central nervous system (CNS) is the glutamate molecule, which binds to neurons, thereby activating cell surface receptors. These receptors can be divided into two major classes, ionotropic and metabotropic glutamate receptors, based on the structural features of the receptor proteins, the means by which the receptors transduce signals into the cell, and pharmacological profiles.

The metabotropic glutamate receptors (mGluRs) are G protein-coupled receptors that activate a variety of intracellular second messenger systems following the binding of glutamate. Activation of mGluRs in intact mammalian neurons elicits one or more of the following responses: activation of phospholipase C; increases in phosphoinositide (PI) hydrolysis; intracellular calcium release; activation of phospholipase D; activation or inhibition of adenyl cyclase; increases or decreases in the formation of cyclic adenosine monophosphate (cAMP); activation of guanylyl cyclase; increases in the formation of cyclic guanosine monophosphate (cGMP); activation of phospholipase A2; increases in arachidonic acid release; and increases or decreases in the activity of voltage- and ligand-gated ion channels. (*Trends Pharmacol. Sci.*, 1993, 14, 13; *Neurochem. Int.*, 1994, 24, 439; *Neuropharmacology*, 1995, 34, 1; *Prog. Neurobiol.*, 1999, 59, 55).

Eight distinct mGluR subtypes, termed mGluR1 through mGluR8, have been identified by molecular cloning (*Neuron*, 1994, 13, 1031; *Neuropharmacology*, 1995, 34, 1; *J. Med. Chem.*, 1995, 38, 1417). Further receptor diversity occurs via expression of alternatively spliced forms of certain mGluR subtypes (*PNAS*, 1992, 89, 10331; *BBRC*, 1994, 199, 1136; *J. Neurosci.*, 1995, 15, 3970).

Metabotropic glutamate receptor subtypes may be subdivided into three groups, Group I, Group II, and Group III mGluRs, based on amino acid sequence homology, the second messenger systems utilized by the receptors, and by their pharmacological characteristics. Group I mGluR comprises mGluR1, mGluR5 and their alternatively spliced variants.

Attempts at elucidating the physiological roles of Group I mGluRs suggest that activation of these receptors elicits neuronal excitation. Evidence indicates that this excitation is due to direct activation of postsynaptic mGluRs, but it also has been suggested that activation of presynaptic mGluRs occurs, resulting in increased neurotransmitter release (*Trends Pharmacol. Sci.*, 1992, 15, 92; *Neurochem. Int.*, 1994, 24, 439; *Neuropharmacology*, 1995, 34, 1; *Trends Pharmacol. Sci.*, 1994, 15, 33).

Metabotropic glutamate receptors have been implicated in a number of normal processes in the mammalian CNS. Activation of mGluRs has been shown to be required for induction of hippocampal long-term potentiation and cerebellar long-term depression (*Nature*, 1993, 363, 347; *Nature*, 1994, 368, 740; *Cell*, 1994, 79, 365; *Cell*, 1994, 79, 377). A role for mGluR activation in nociception and analgesia also has been demonstrated (*Neuroreport*, 1993, 4, 879; *Brain Res.*, 1999, 871, 223).

Group I metabotropic glutamate receptors and mGluR5 in particular, have been suggested to play roles in a variety of pathophysiological processes and disorders affecting the CNS. These include stroke, head trauma, anoxic and ischemic injuries, hypoglycemia, epilepsy, neurodegenerative disorders such as Alzheimer's disease, acute and chronic pain, substance abuse and withdrawal, obesity and gastroesophageal reflux disease (GERD) and irritable bowel syndrome (*Trends Pharmacol. Sci.*, 1993, 14, 13; *Life Sci.*, 1994, 54, 135; *Ann. Rev. Neurosci.*, 1994, 17, 31; *Neuropharmacology*, 1995, 34, 1; *J. Med. Chem.*, 1995, 38, 1417; *Trends Pharmacol. Sci.*, 2001, 22, 331; *Curr. Opin. Pharmacol.*, 2002, 2, 43; *Pain*, 2002, 98, 1, *Curr Top Med Chem.*, 2005; 5(9):897-911). Much of the pathology in these conditions is thought to be due to excessive glutamate-induced excitation of CNS neurons. As Group I mGluRs appear to increase glutamate-mediated neuronal excitation via postsynaptic mechanisms and enhanced presynaptic glutamate release, their activation probably contributes to the pathology. Accordingly, selective antagonists of Group I mGluR receptors could be therapeutically beneficial, specifically as neuroprotective agents, analgesics or anticonvulsants.

International Patent Publication No. WO 2006/120573 describes a method for inhibiting the proliferation of cancer cells in mammal by administering a therapeutically effective amount of heterocyclic mono-N-oxides.

General methods for the preparation of quinolines can be found in, e.g., International Patent Publication No. WO 2005/070890, *J. Med. Chem.*, 2003, 46, 49 and *J. Med. Chem.*, 2005, 48, 1107. 4-amino-3-cyano-quinoline derivatives are prepared by condensation of anilines with 2-cyano-3-ethoxyacrylic acid ethyl ester followed by the ring closure of the obtained intermediates. Thermal ring closure affords 3-cyano-4-hydroxy-quinoline derivatives that are converted into 3-cyano-4-chloro-quinoline derivatives using phosphorous (V) oxychloride. Ring closure with phosphorous(V) oxyhalogenides directly results in 3-cyano-4-halogen-quinoline derivatives.

International Patent Publication No. WO 2005/58834 discloses quinoline derivatives for use in treating liver X receptor (LXR) mediated diseases particularly multiple sclerosis, rheumatoid arthritis, inflammatory bowel disease and atherosclerosis, which compounds suppress Th-1 type lymphokine production, resulting in increased HDL levels, and cholesterol metabolism. The synthesis of 3-benzenesulfonyl-4-phenyl-8-trifluoromethyl-quinoline by the reaction of the appropriate aniline derivative (e.g., scheme 9 of WO 2005/58834) with 1,2-bis(benzenesulfonyl)-ethylene is described. This compound proved to be inactive on mGluR1 and mGluR5 receptors.

International Patent Publication No. WO 2005/30129 relates to compounds useful as potassium channel inhibitors. Compounds in this class may be useful as Kv1.5 antagonists for treating and preventing cardiac arrhythmias, and the like, and as Kv1.3 inhibitors for treatment of immunosuppression, autoimmune diseases, and the like.

None of the references disclose activity at the mGluR1 and/or mGluR5 receptors. Accordingly, there is a need for new compounds having activity on the mGluR1 and mGluR5 receptors.

SUMMARY OF THE INVENTION

The present invention relates to new mGluR1 and mGluR5 receptor subtype preferring ligands of formula (I):

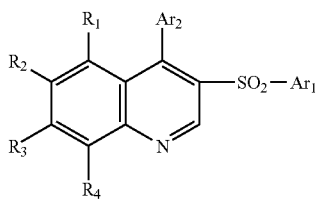

(I)

wherein

Ar$_1$ represents an optionally substituted phenyl or heteroaryl group;

Ar$_2$ represents a substituted phenyl or an optionally substituted heteroaryl group;

R$_1$, R$_2$, R$_3$ and R$_4$ represent independently a substituent selected from hydrogen, halogen, cyano, alkyl, alkoxy, hydroxy, trifluoromethyl, amino, alkylamino, dialkylamino, aminomethyl, alkylaminomethyl, dialkylaminomethyl, and/or salts and/or hydrates and/or solvates and/or polymorphs thereof. The invention also relates to processes and intermediates for producing the same, to pharmaceutical compositions containing the same and to their use in treatment and/or prevention of pathological conditions which require the modulation of mGluR1 and mGluR5 receptors such as, but not limited to, neurological disorders, psychiatric disorders, acute and chronic pain and neuromuscular dysfunctions of the lower urinary tract.

DETAILED DESCRIPTION OF THE INVENTION

In one aspect, the present invention relates to new mGluR1 and mGluR5 receptor subtype preferring ligands of formula (I):

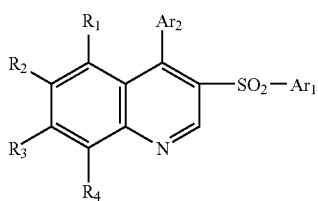

(I)

wherein

Ar$_1$ represents an optionally substituted phenyl or heteroaryl group;

Ar$_2$ represents a substituted phenyl or an optionally substituted heteroaryl group;

R$_1$, R$_2$, R$_3$ and R$_4$ represent independently a substituent selected from hydrogen, halogen, cyano, alkyl, alkoxy, hydroxy, trifluoromethyl, amino, alkylamino, dialkylamino, aminomethyl, alkylaminomethyl, dialkylaminomethyl, and/or salts and/or hydrates and/or solvates and/or polymorphs thereof.

When Ar$_1$ represents phenyl, the phenyl group may be optionally substituted with one or more substituent(s) selected from hydrogen, halogen, cyano, alkyl, alkoxy, trifluoromethyl, dialkylamino and combinations thereof. When Ar$_2$ represents phenyl, the phenyl group is substituted with one or more substituent(s) selected from halogen, cyano, alkyl, alkoxy, trifluoromethyl, dialkylamino and combinations thereof.

When Ar$_1$ and/or Ar$_2$ represent heteroaryl, the heteroaryl group may be an aromatic 5 to 6 membered heterocyclic ring containing 1 to 2 heteroatom(s) selected from O, N or S, such as, but not limited to, pyridyl, thiazolyl, oxazolyl. The heteroaryl group may be optionally substituted with one or more substituent(s) selected from hydrogen, alkyl, alkoxy, halogen and combinations thereof.

When R$_1$ and/or R$_2$ and/or R$_3$ and/or R$_4$ represent represents alkyl, the alkyl group contains 1 to 4 carbon atom(s) and may be straight or branched chain.

When R$_1$ and/or R$_2$ and/or R$_3$ and/or R$_4$ represent alkoxy, alkylamino, dialkylamino, alkylaminomethyl, or dialkylaminomethyl, the alkyl moiety of the group contains 1 to 4 carbon atom(s) and may be straight or branched chain.

As used herein, the term "halogen" includes fluorine, chlorine, bromine and iodine atoms.

As used herein, the term "halo" includes fluoro, chloro, bromo or iodo.

Compounds of formula (I) contain basic function(s) and thus may form salts with acids. The invention also relates to salts of compounds of formula (I) formed with acids, especially salts formed with pharmaceutically acceptable acids.

Both organic and inorganic acids can be used for the formation of acid addition salts. Suitable inorganic acids can be, for example, hydrochloric acid, sulfuric acid, nitric acid and phosphoric acid. Representatives of monovalent organic acids can be, for example, formic acid, acetic acid, propionic acid, and different butyric acids, valeric acids and capric acids. Representatives of bivalent organic acids can be, for example, oxalic acid, malonic acid, maleic acid, fumaric acid and succinic acid. Other organic acids can also be used, such as hydroxy acids, for example, citric acid, tartaric acid, or aromatic carboxylic acids, for example, benzoic acid or salicylic acid, as well as aliphatic and aromatic sulfonic acids, for example, methanesulfonic acid, naphthalenesulfonic acid and p-toluenesulfonic acid. A preferred group of acid addition salts are those in which the acid component itself is physiologically acceptable and does not have a therapeutic effect in the applied dose and/or it does not have unfavourable influence on the effect of the active ingredient. These acid addition salts are pharmaceutically acceptable acid addition salts. Acid addition salts which are not pharmaceutically acceptable acid addition salts can be advantageous in the purification and isolation of the desired compounds of formula (I), and are therefore also included within the scope of the present invention.

As used herein in the present specification and claims a "compound of formula (I)" will be deemed to encompass both the free base and salts, e.g., pharmaceutically acceptable salts, thereof.

Solvates and/or hydrates of compounds of formula (I), as well as solvates and/or hydrates of salts of compounds of formula (I) are also included within the scope of the present invention.

One of ordinary skill in the art will also recognize that some of the compounds of formula (I) can exist in different polymorphic forms. As known in the art, polymorphism is an ability of a compound to crystallize as more than one distinct crystalline or "polymorphic" species. A polymorph is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds.

In certain embodiments, compounds of the invention are those compounds of formula (I), wherein $Ar_1$ represents phenyl or heteroaryl group, optionally substituted with one or more substituent(s) selected from hydrogen, fluoro, chloro, cyano, methyl, methoxy and combinations thereof;

$Ar_2$ represents phenyl, substituted with one or more substituent(s) selected from fluoro, chloro, cyano, methyl, methoxy and combinations thereof; or heteroaryl, optionally substituted with one or more substituent(s) selected from hydrogen, fluoro, chloro, cyano, methyl, methoxy and combinations thereof;

$R_1$, $R_2$, $R_3$ and represent independently a substituent selected from hydrogen, fluoro, chloro, cyano, methyl, methoxy, hydroxy, trifluoromethyl, amino, methylamino, dimethylamino, aminomethyl, methylaminomethyl, dimethylaminomethyl, and/or salts and/or hydrates and/or solvates and/or polymorphs thereof.

In further embodiments, compounds of the invention are those compounds of formula (I), wherein $Ar_1$ represents phenyl, pyridyl, thienyl or oxazolyl group, optionally substituted with one or more substituent(s) selected from hydrogen, fluoro, chloro, cyano, methyl, methoxy and combinations thereof;

$Ar_2$ represents phenyl, substituted with one or more substituent(s) selected from fluoro, chloro, cyano, methyl, methoxy and combinations thereof; or pyridyl, thienyl or oxazolyl, optionally substituted with one or more substituent(s) selected from hydrogen, fluoro, chloro, cyano, methyl, methoxy and combinations thereof;

$R_1$, $R_2$, $R_3$ and $R_4$ represent independently a substituent selected from hydrogen, fluoro, chloro, cyano, methyl, methoxy, hydroxy, trifluoromethyl, amino, methylamino, dimethylamino, aminomethyl, methylaminomethyl, dimethylaminomethyl, and/or salts and/or hydrates and/or solvates and/or polymorphs thereof.

In a further embodiment, the compound of formula (I) is selected from 4-(4-chloro-phenyl)-3-(4-methyl-benzenesulfonyl)-quinoline,
7-chloro-3-(4-chloro-benzenesulfonyl)-4-(4-fluoro-phenyl)-quinoline,
8-chloro-4-(3-chloro-phenyl)-3-(3,4-dichloro-benzenesulfonyl)-quinoline,
7-fluoro-3-(4-fluoro-benzenesulfonyl)-4-(3-fluoro-phenyl)-quinoline,
4-(4-chloro-phenyl)-7-fluoro-3-(4-methoxy-benzenesulfonyl)-quinoline,
7-fluoro-3-(4-methoxy-benzenesulfonyl)-4-(4-methoxy-phenyl)-quinoline,
7-fluoro-3-(3-fluoro-benzenesulfonyl)-4-(3-fluoro-phenyl)-quinoline,
7-fluoro-3-(3-fluoro-benzenesulfonyl)-4-(4-fluoro-phenyl)-quinoline,
4-(3-chloro-phenyl)-3-(3,4-dimethyl-benzenesulfonyl)-7-fluoro-quinoline,
3-(3,4-dimethyl-benzenesulfonyl)-7-fluoro-4-(3-fluoro-phenyl)-quinoline,
3-(3,4-dimethyl-benzenesulfonyl)-7-fluoro-4-(3-methoxyphenyl)-quinoline,
4-(3-chloro-phenyl)-8-fluoro-3-(4-fluoro-benzenesulfonyl)-quinoline,
4-(4-chloro-phenyl)-8-fluoro-3-(4-fluoro-benzenesulfonyl)-quinoline,
8-fluoro-3-(4-fluoro-benzenesulfonyl)-4-(3-fluoro-phenyl)-quinoline,
8-fluoro-3-(4-fluoro-benzenesulfonyl)-4-(3-methoxy-phenyl)-quinoline,
4-(4-chloro-phenyl)-6-fluoro-3-(4-methoxy-benzenesulfonyl)-quinoline,
4-(4-chloro-phenyl)-3-(3,4-dimethyl-benzenesulfonyl)-6-fluoro-quinoline,
4-(4-chloro-phenyl)-3-(3,5-difluoro-benzenesulfonyl)-7-fluoro-quinoline,
3-(3,5-difluoro-benzenesulfonyl)-7-fluoro-4-(4-fluoro-phenyl)-quinoline,
4-(4-chloro-phenyl)-3-(3-cyano-benzenesulfonyl)-7-fluoro-quinoline,
3-(3-cyano-benzenesulfonyl)-7-fluoro-4-(3-fluoro-phenyl)-quinoline,
3-(3-cyano-benzenesulfonyl)-7-fluoro-4-(4-fluoro-phenyl)-quinoline,
7-fluoro-3-(4-fluoro-benzenesulfonyl)-4-(4-fluoro-phenyl)-quinoline,
4-(4-chloro-phenyl)-7-fluoro-3-(3-fluoro-benzenesulfonyl)-quinoline,
4-(3-chloro-phenyl)-7-fluoro-3-(3-methoxy-benzenesulfonyl)-quinoline,
7-fluoro-4-(4-fluoro-phenyl)-3-(3-methoxy-benzenesulfonyl)-quinoline,
4-(4-chloro-phenyl)-3-(3,4-dimethyl-benzenesulfonyl)-7-fluoro-quinoline,
3-(3,4-dimethyl-benzenesulfonyl)-7-fluoro-4-(4-fluoro-phenyl)-quinoline,
4-(3-chloro-phenyl)-3-(3-chloro-4-methoxy-benzenesulfonyl)-7-fluoro-quinoline,
3-(3-chloro-4-methoxy-benzenesulfonyl)-7-fluoro-4-(3-fluoro-phenyl)-quinoline,
3-(3-chloro-4-methoxy-benzenesulfonyl)-7-fluoro-4-(4-fluoro-phenyl)-quinoline,
3-(3,5-dichloro-benzenesulfonyl)-8-fluoro-4-(4-fluoro-phenyl)-quinoline,
3-(3,5-difluoro-benzenesulfonyl)-8-fluoro-4-(3-fluoro-phenyl)-quinoline,
8-fluoro-3-(4-fluoro-benzenesulfonyl)-4-(4-methoxy-phenyl)-quinoline,
4-(3-chloro-phenyl)-8-fluoro-3-(4-methoxy-benzenesulfonyl)-quinoline,
4-(4-chloro-phenyl)-8-fluoro-3-(4-methoxy-benzenesulfonyl)-quinoline,
8-fluoro-4-(4-fluoro-phenyl)-3-(4-methoxy-benzenesulfonyl)-quinoline,
8-fluoro-3-(4-methoxy-benzenesulfonyl)-4-(4-methoxy-phenyl)-quinoline,
8-fluoro-3-(4-methoxy-benzenesulfonyl)-4-(3-methoxy-phenyl)-quinoline,
4-(3-chloro-phenyl)-8-fluoro-3-(3-fluoro-benzenesulfonyl)-quinoline,
4-(4-chloro-phenyl)-8-fluoro-3-(3-fluoro-benzenesulfonyl)-quinoline, 8-fluoro-3-(3-fluoro-benzenesulfonyl)-4-(3-fluoro-phenyl)-quinoline,
8-fluoro-3-(3-fluoro-benzenesulfonyl)-4-(4-methoxy-phenyl)-quinoline,
8-fluoro-3-(3-fluoro-benzenesulfonyl)-4-(3-methoxy-phenyl)-quinoline,
8-fluoro-3-(3-fluoro-benzenesulfonyl)-4-(4-fluoro-phenyl)-quinoline,
3-(3-cyano-benzenesulfonyl)-6-fluoro-4-(3-fluoro-phenyl)-quinoline,
3-(3-cyano-benzenesulfonyl)-6-fluoro-4-(3-methoxy-phenyl)-quinoline,
3-(3-cyano-benzenesulfonyl)-6-fluoro-4-(4-fluoro-phenyl)-quinoline,
4-(3-chloro-phenyl)-6-fluoro-3-(3-methoxy-benzenesulfonyl)-quinoline,
6-fluoro-4-(4-fluoro-phenyl)-3-(3-methoxy-benzenesulfonyl)-quinoline,
3-(3-chloro-4-methoxy-benzenesulfonyl)-6-fluoro-4-(4-methoxy-phenyl)-quinoline,
3-(3-chloro-4-methoxy-benzenesulfonyl)-6-fluoro-4-(3-methoxy-phenyl)-quinoline,
4-(4-chloro-phenyl)-7-fluoro-3-(4-fluoro-benzenesulfonyl)-quinoline,
3-(3,4-dimethyl-benzenesulfonyl)-7-fluoro-4-(4-methoxy-phenyl)-quinoline,
3-(3-chloro-4-methoxy-benzenesulfonyl)-4-(4-chloro-phenyl)-6-fluoro-quinoline,
3-(3-chloro-4-methoxy-benzenesulfonyl)-6-fluoro-4-(3-fluoro-phenyl)-quinoline,
3-(3,5-dichloro-benzenesulfonyl)-7-fluoro-4-(4-methoxy-phenyl)-quinoline,
3-(3,5-dichloro-benzenesulfonyl)-7-fluoro-4-(3-methoxy-phenyl)-quinoline,
3-(3,5-difluoro-benzenesulfonyl)-7-fluoro-4-(4-fluoro-phenyl)-quinoline,
4-(3-chloro-phenyl)-7-fluoro-3-(3-fluoro-4-methyl-benzenesulfonyl)-quinoline,
7-fluoro-3-(3-fluoro-4-methyl-benzenesulfonyl)-4-(3-fluoro-phenyl)-quinoline,
7-fluoro-3-(3-fluoro-4-methyl-benzenesulfonyl)-4-(4-fluoro-phenyl)-quinoline,
3-(3,5-difluoro-benzenesulfonyl)-7-fluoro-4-(3-fluoro-phenyl)-quinoline,
3-(3,5-difluoro-benzenesulfonyl)-7-fluoro-4-(4-methoxy-phenyl)-quinoline,
3-(3,5-difluoro-benzenesulfonyl)-7-fluoro-4-(3-methoxy-phenyl)-quinoline,
4-(3-chloro-phenyl)-3-(3-cyano-benzenesulfonyl)-7-fluoro-quinoline,
3-(3-cyano-benzenesulfonyl)-7-fluoro-4-(4-methoxy-phenyl)-quinoline,
3-(3-cyano-benzenesulfonyl)-7-fluoro-4-(3-methoxy-phenyl)-quinoline,
3-(3-chloro-4-methyl-benzenesulfonyl)-7-fluoro-4-(3-fluoro-phenyl)-quinoline,
3-(3,4-difluoro-benzenesulfonyl)-7-fluoro-4-(3-fluoro-phenyl)-quinoline,
3-(3,4-difluoro-benzenesulfonyl)-7-fluoro-4-(4-methoxy-phenyl)-quinoline,
3-(3,4-difluoro-benzenesulfonyl)-7-fluoro-4-(3-methoxy-phenyl)-quinoline,
3-(3,4-difluoro-benzenesulfonyl)-7-fluoro-4-(4-fluoro-phenyl)-quinoline,
3-(3-chloro-4-fluoro-benzenesulfonyl)-4-(4-chloro-phenyl)-7-fluoro-quinoline,
3-(3-chloro-4-fluoro-benzenesulfonyl)-7-fluoro-4-(3-fluoro-phenyl)-quinoline,
3-(3-chloro-4-fluoro-benzenesulfonyl)-7-fluoro-4-(4-methoxy-phenyl)-quinoline,
3-(3-chloro-4-fluoro-benzenesulfonyl)-7-fluoro-4-(4-fluoro-phenyl)-quinoline,
3-(3,5-dichloro-benzenesulfonyl)-8-fluoro-4-(3-fluoro-phenyl)-quinoline,
3-(3,5-dichloro-benzenesulfonyl)-8-fluoro-4-(4-methoxy-phenyl)-quinoline,
3-(3,5-dichloro-benzenesulfonyl)-8-fluoro-4-(3-methoxy-phenyl)-quinoline,
4-(3-chloro-phenyl)-8-fluoro-3-(3-fluoro-4-methyl-benzenesulfonyl)-quinoline,
4-(4-chloro-phenyl)-8-fluoro-3-(3-fluoro-4-methyl-benzenesulfonyl)-quinoline,
8-fluoro-3-(3-fluoro-4-methyl-benzenesulfonyl)-4-(3-fluoro-phenyl)-quinoline,
8-fluoro-3-(3-fluoro-4-methyl-benzenesulfonyl)-4-(4-methoxy-phenyl)-quinoline,
8-fluoro-3-(3-fluoro-4-methyl-benzenesulfonyl)-4-(3-methoxy-phenyl)-quinoline,
8-fluoro-3-(3-fluoro-4-methyl-benzenesulfonyl)-4-(4-fluoro-phenyl)-quinoline,
4-(3-chloro-phenyl)-3-(3,5-difluoro-benzenesulfonyl)-8-fluoro-quinoline,
4-(4-chloro-phenyl)-3-(3,5-difluoro-benzenesulfonyl)-8-fluoro-quinoline,
3-(3,5-difluoro-benzenesulfonyl)-8-fluoro-4-(4-methoxy-phenyl)-quinoline,
3-(3,5-difluoro-benzenesulfonyl)-8-fluoro-4-(3-methoxy-phenyl)-quinoline,
3-(3,5-difluoro-benzenesulfonyl)-8-fluoro-4-(4-fluoro-phenyl)-quinoline,
4-(4-chloro-phenyl)-3-(3,4-difluoro-benzenesulfonyl)-8-fluoro-quinoline,
3-(3,4-difluoro-benzenesulfonyl)-8-fluoro-4-(3-fluoro-phenyl)-quinoline,
3-(3,4-difluoro-benzenesulfonyl)-8-fluoro-4-(4-methoxy-phenyl)-quinoline,
3-(3,4-difluoro-benzenesulfonyl)-8-fluoro-4-(4-fluoro-phenyl)-quinoline,
3-(3,5-dichloro-benzenesulfonyl)-6-fluoro-4-(3-fluoro-phenyl)-quinoline,
3-(3,5-dichloro-benzenesulfonyl)-6-fluoro-4-(4-methoxy-phenyl)-quinoline,
3-(3,5-dichloro-benzenesulfonyl)-6-fluoro-4-(3-methoxy-phenyl)-quinoline,
4-(3-chloro-phenyl)-6-fluoro-3-(3-fluoro-4-methyl-benzenesulfonyl)-quinoline,
6-fluoro-3-(3-fluoro-4-methyl-benzenesulfonyl)-4-(3-fluoro-phenyl)-quinoline,
6-fluoro-3-(3-fluoro-4-methyl-benzenesulfonyl)-4-(4-methoxy-phenyl)-quinoline,
6-fluoro-3-(3-fluoro-4-methyl-benzenesulfonyl)-4-(3-methoxy-phenyl)-quinoline,
6-fluoro-3-(3-fluoro-4-methyl-benzenesulfonyl)-4-(4-fluoro-phenyl)-quinoline,
4-(3-chloro-phenyl)-3-(3-cyano-benzenesulfonyl)-6-fluoro-quinoline,
4-(4-chloro-phenyl)-3-(3-cyano-benzenesulfonyl)-6-fluoro-quinoline,
3-(3-cyano-benzenesulfonyl)-6-fluoro-4-(4-methoxy-phenyl)-quinoline,
3-(3-chloro-4-methyl-benzenesulfonyl)-4-(3-chloro-phenyl)-6-fluoro-quinoline, 3-(3-chloro-4-methyl-benzenesulfonyl)-4-(4-chloro-phenyl)-6-fluoro-quinoline,
3-(3-chloro-4-methyl-benzenesulfonyl)-6-fluoro-4-(3-fluoro-phenyl)-quinoline,
3-(3-chloro-4-methyl-benzenesulfonyl)-6-fluoro-4-(3-methoxy-phenyl)-quinoline,
3-(3-chloro-4-methyl-benzenesulfonyl)-6-fluoro-4-(4-fluoro-phenyl)-quinoline,
4-(4-chloro-phenyl)-6-fluoro-3-(3-methoxy-benzenesulfonyl)-quinoline,
6-fluoro-3-(3-methoxy-benzenesulfonyl)-4-(3-methoxy-phenyl)-quinoline,
3-(3,4-dimethyl-benzenesulfonyl)-6-fluoro-4-(3-fluoro-phenyl)-quinoline,
3-(3,4-dimethyl-benzenesulfonyl)-6-fluoro-4-(4-methoxy-phenyl)-quinoline,
3-(3,4-dimethyl-benzenesulfonyl)-6-fluoro-4-(4-fluoro-phenyl)-quinoline,
3-(3,4-difluoro-benzenesulfonyl)-6-fluoro-4-(3-fluoro-phenyl)-quinoline,
3-(3,4-difluoro-benzenesulfonyl)-6-fluoro-4-(4-fluoro-phenyl)-quinoline,
3-(3-chloro-4-fluoro-benzenesulfonyl)-4-(4-chloro-phenyl)-6-fluoro-quinoline,
3-(3-chloro-4-fluoro-benzenesulfonyl)-6-fluoro-4-(3-methoxy-phenyl)-quinoline,
3-(3-chloro-4-fluoro-benzenesulfonyl)-6-fluoro-4-(4-fluoro-phenyl)-quinoline,
4-(3-chloro-phenyl)-3-(3,5-dichloro-benzenesulfonyl)-7-fluoro-quinoline,
4-(4-chloro-phenyl)-3-(3,5-dichloro-benzenesulfonyl)-7-fluoro-quinoline,
4-(3-chloro-phenyl)-3-(3,5-dichloro-benzenesulfonyl)-8-fluoro-quinoline,
4-(4-chloro-phenyl)-3-(3,5-dichloro-benzenesulfonyl)-8-fluoro-quinoline,
4-(3-chloro-phenyl)-3-(3,5-dichloro-benzenesulfonyl)-6-fluoro-quinoline,
4-(4-chloro-phenyl)-3-(3,5-dichloro-benzenesulfonyl)-6-fluoro-quinoline,
6-fluoro-3-(4-methoxy-benzenesulfonyl)-4-(4-methoxy-phenyl)-quinoline,
7-chloro-4-(4-chloro-phenyl)-3-(3,5-difluoro-benzenesulfonyl)-quinoline,
7-chloro-4-(4-chloro-phenyl)-3-(3,4-difluoro-benzenesulfonyl)-quinoline,
7-chloro-4-(4-chloro-phenyl)-3-(3-cyano-benzenesulfonyl)-quinoline,
7-chloro-3-(3,5-dichloro-benzenesulfonyl)-4-(4-fluoro-phenyl)-quinoline,
7-chloro-3-(4-fluoro-benzenesulfonyl)-4-(4-fluoro-phenyl)-quinoline,
7-chloro-3-(3-fluoro-benzenesulfonyl)-4-(4-fluoro-phenyl)-quinoline,
7-chloro-3-(3,4-difluoro-benzenesulfonyl)-4-(4-fluoro-phenyl)-quinoline,
7-chloro-3-(3-chloro-4-fluoro-benzenesulfonyl)-4-(4-fluoro-phenyl)-quinoline,
7-chloro-3-(3-cyano-5-fluoro-benzenesulfonyl)-4-(4-fluoro-phenyl)-quinoline,
6-chloro-3-(3-chloro-4-fluoro-benzenesulfonyl)-4-(4-chloro-phenyl)-7-fluoro-quinoline,
6-chloro-3-(3-chloro-4-fluoro-benzenesulfonyl)-7-fluoro-4-(4-fluoro-phenyl)-quinoline,
3-(3-chloro-4-fluoro-benzenesulfonyl)-7-cyano-4-(2-fluoro-phenyl)-quinoline,
7-chloro-3-(3,4-difluoro-benzenesulfonyl)-8-fluoro-4-(3-fluoro-phenyl)-quinoline,
7-chloro-3-(3-chloro-4-fluoro-benzenesulfonyl)-4-(4-fluoro-phenyl)-8-fluoro-quinoline,
7-chloro-3-(3-chloro-4-fluoro-benzenesulfonyl)-8-fluoro-4-(3-fluoro-phenyl)-quinoline,
7-chloro-4-(4-chloro-phenyl)-3-(3,4-difluoro-benzenesulfonyl)-8-fluoro-quinoline,
7-chloro-3-(3-chloro-4-fluoro-benzenesulfonyl)-8-fluoro-4-(4-fluoro-phenyl)-quinoline,
3-(3-cyano-4-fluoro-benzenesulfonyl)-4-(3-fluoro-phenyl)-quinoline,
3-(3-cyano-5-fluoro-benzenesulfonyl)-4-(3-fluoro-phenyl)-quinoline,
3-(3-chloro-4-fluoro-benzenesulfonyl)-4-(4-chloro-phenyl)-8-fluoro-quinoline,
3-(3-chloro-4-fluoro-benzenesulfonyl)-8-fluoro-4-(2-fluoro-phenyl)-quinoline,
3-(3-chloro-4-fluoro-benzenesulfonyl)-8-fluoro-4-(3-fluoro-phenyl)-quinoline,
3-(3-cyano-4-fluoro-benzenesulfonyl)-4-(4-fluoro-phenyl)-quinoline,
3-(3-chloro-4-fluoro-benzenesulfonyl)-8-fluoro-4-(4-fluoro-phenyl)-quinoline,
3-(3-cyano-benzenesulfonyl)-8-fluoro-4-(2-fluoro-phenyl)-quinoline,
3-(3-cyano-benzenesulfonyl)-4-(3-fluoro-phenyl)-quinoline,
3-(3-cyano-benzenesulfonyl)-8-fluoro-4-(3-fluoro-phenyl)-quinoline,
3-(3-cyano-4-fluoro-benzenesulfonyl)-7-fluoro-4-(3-fluoro-phenyl)-quinoline,
4-(3-chloro-phenyl)-3-(3-cyano-4-fluoro-benzenesulfonyl)-quinoline,
3-(3-cyano-5-fluoro-benzenesulfonyl)-7-fluoro-4-(4-fluoro-phenyl)-quinoline,
7-chloro-3-(3-cyano-4-fluoro-benzenesulfonyl)-4-(3-fluoro-phenyl)-quinoline,
3-(3,5-dichloro-benzenesulfonyl)-4-(3,4-difluoro-phenyl)-8-fluoro-quinoline,
7-chloro-3-(3-cyano-5-fluoro-benzenesulfonyl)-4-(3-fluoro-phenyl)-quinoline,
3-(3-cyano-benzenesulfonyl)-8-fluoro-4-(4-fluoro-phenyl)-quinoline,
3-(3,5-dichloro-benzenesulfonyl)-8-fluoro-4-(2-fluoro-phenyl)-quinoline,
3-(3-chloro-4-fluoro-benzenesulfonyl)-7-fluoro-4-(2-fluoro-phenyl)-quinoline,
4-(4-chloro-phenyl)-3-(3-cyano-benzenesulfonyl)-8-fluoro-quinoline,
4-(3-chloro-phenyl)-3-(3-cyano-5-fluoro-benzenesulfonyl)-quinoline,
7-chloro-3-(3-cyano-benzenesulfonyl)-4-(2-fluoro-phenyl)-quinoline,
3-(3-cyano-5-fluoro-benzenesulfonyl)-7-fluoro-4-(3-fluoro-phenyl)-quinoline,
3-(3-chloro-4-fluoro-benzenesulfonyl)-4-(3-chloro-phenyl)-8-fluoro-quinoline,
3-(3-cyano-benzenesulfonyl)-7-fluoro-4-(2-fluoro-phenyl)-quinoline,
3-(3-cyano-5-fluoro-benzenesulfonyl)-4-(3,4-difluoro-phenyl)-7-fluoro-quinoline,
3-(3-cyano-4-fluoro-benzenesulfonyl)-4-(3,4-dichloro-phenyl)-quinoline,
7-chloro-3-(3-chloro-4-fluoro-benzenesulfonyl)-4-(2-fluoro-phenyl)-quinoline, 7-chloro-3-(3-cyano-benzenesulfonyl)-4-(3-fluoro-phenyl)-quinoline,
4-(3-chloro-phenyl)-3-(3-cyano-4-fluoro-benzenesulfonyl)-7-fluoro-quinoline,
3-(3,4-difluoro-benzenesulfonyl)-4-(3,5-difluoro-phenyl)-8-fluoro-quinoline,
3-(3,4-difluoro-benzenesulfonyl)-4-(4-fluoro-phenyl)-quinoline,
3-(3,4-difluoro-benzenesulfonyl)-4-(3,4-difluoro-phenyl)-8-fluoro-quinoline,
3-(3,5-dichloro-benzenesulfonyl)-4-(3,4-difluoro-phenyl)-7-fluoro-quinoline,
3-(3,4-difluoro-benzenesulfonyl)-4-(3-fluoro-phenyl)-quinoline,
7-chloro-3-(3-cyano-benzenesulfonyl)-4-(4-fluoro-phenyl)-quinoline,
7-chloro-4-(3-chloro-phenyl)-3-(3-cyano-4-fluoro-benzenesulfonyl)-quinoline,
3-(3,4-difluoro-benzenesulfonyl)-8-fluoro-4-(2-fluoro-phenyl)-quinoline,
4-(3-chloro-phenyl)-3-(3-cyano-5-fluoro-benzenesulfonyl)-7-fluoro-quinoline,
3-(3-cyano-benzenesulfonyl)-4-(3,5-difluoro-phenyl)-7-fluoro-quinoline,
4-(3-chloro-phenyl)-3-(3-cyano-benzenesulfonyl)-8-fluoro-quinoline,
4-(4-chloro-phenyl)-3-(3,4-difluoro-benzenesulfonyl)-7-fluoro-quinoline,
7-chloro-3-(3,4-dichloro-benzenesulfonyl)-4-(3,4-difluoro-phenyl)-quinoline,
3-(3,5-dicyano-benzenesulfonyl)-7-fluoro-4-(4-fluoro-phenyl)-quinoline,
7-chloro-3-(3-chloro-5-fluoro-benzenesulfonyl)-4-(3-chloro-phenyl)-quinoline,
3-(3,4-difluoro-benzenesulfonyl)-4-(3,4-difluoro-phenyl)-7-fluoro-quinoline,
7-chloro-4-(3-chloro-phenyl)-3-(3,5-dichloro-benzenesulfonyl)-8-fluoro-quinoline,
7-chloro-4-(3-chloro-phenyl)-3-(3-cyano-benzenesulfonyl)-8-fluoro-quinoline,
7-chloro-4-(3-chloro-phenyl)-3-(3-cyano-benzenesulfonyl)-quinoline,
7-chloro-3-(3,5-dichloro-benzenesulfonyl)-4-(2-fluoro-phenyl)-quinoline,
3-(3,5-dicyano-benzenesulfonyl)-4-(3,4-difluoro-phenyl)-7-fluoro-quinoline,
3-(3,5-dichloro-benzenesulfonyl)-7-fluoro-4-(2-fluoro-phenyl)-quinoline,
3-(3-chloro-4-fluoro-benzenesulfonyl)-4-(3-chloro-phenyl)-7-fluoro-quinoline,
4-(3-chloro-phenyl)-3-(3,4-difluoro-benzenesulfonyl)-8-fluoro-quinoline,
4-(3,4-dichloro-phenyl)-3-(3,4-difluoro-benzenesulfonyl)-quinoline,
3-(3,4-difluoro-benzenesulfonyl)-7-fluoro-4-(2-fluoro-phenyl)-quinoline,
7-chloro-3-(3-chloro-4-fluoro-benzenesulfonyl)-4-(3,5-difluoro-phenyl)-quinoline,
7-chloro-4-(3-chloro-phenyl)-3-(3,5-dichloro-benzenesulfonyl)-quinoline,
7-amino-3-(3,4-difluoro-benzenesulfonyl)-4-(3-fluoro-phenyl)-quinoline,
4-(3-chloro-phenyl)-3-(3-cyano-benzenesulfonyl)-quinoline,
3-(3-cyano-5-fluoro-benzenesulfonyl)-4-(3,4-difluoro-phenyl)-quinoline,
3-(3-cyano-5-fluoro-benzenesulfonyl)-7-fluoro-4-(4-fluoro-phenyl)-quinoline,
4-(4-chloro-phenyl)-3-(3-cyano-5-fluoro-benzenesulfonyl)-7-fluoro-quinoline,
7-chloro-3-(3-chloro-5-fluoro-benzenesulfonyl)-4-(4-chloro-phenyl)-quinoline,
7-chloro-3-(3-chloro-5-fluoro-benzenesulfonyl)-4-(4-fluoro-phenyl)-quinoline,
3-(3-chloro-5-fluoro-benzenesulfonyl)-4-(4-fluoro-phenyl)-quinoline,
3-(3-chloro-5-fluoro-benzenesulfonyl)-4-(4-chloro-phenyl)-quinoline,
3-(3-chloro-4-fluoro-benzenesulfonyl)-4-(4-chloro-phenyl)-quinoline,
3-(3-chloro-4-fluoro-benzenesulfonyl)-4-(4-chloro-phenyl)-7-fluoro-quinoline,
3-(3-chloro-4-fluoro-benzenesulfonyl)-7-fluoro-4-(4-fluoro-phenyl)-quinoline,
7-chloro-3-(3-chloro-4-fluoro-benzenesulfonyl)-4-(4-fluoro-phenyl)-quinoline,
7-chloro-3-(3-chloro-4-fluoro-benzenesulfonyl)-4-(4-chloro-phenyl)-quinoline,
7-amino-3-(3-chloro-5-fluoro-benzenesulfonyl)-4-(4-fluoro-phenyl)-quinoline,
7-amino-3-(3-chloro-5-fluoro-benzenesulfonyl)-4-(3-fluoro-phenyl)-quinoline,
and/or salts and/or hydrates and/or solvates and/or polymorphs thereof.

In another aspect, the present invention relates to compounds of formula (IV):

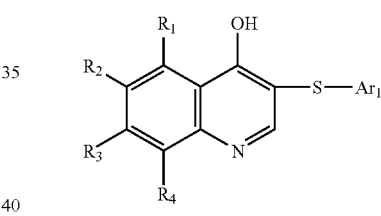

wherein
$Ar_1$ represents an optionally substituted phenyl or heteroaryl group; and
$R_1$, $R_2$, and $R_3$ represent independently a substituent selected from hydrogen, halogen, cyano, alkyl, alkoxy, hydroxy, trifluoromethyl, amino, alkylamino, dialkylamino, aminomethyl, alkylaminomethyl, dialkylaminomethyl,
$R_4$ is selected from hydrogen, halogen, cyano, alkyl, alkoxy, hydroxy, amino, alkylamino, dialkylamino, aminomethyl, alkylaminomethyl, dialkylaminomethyl,
and/or salts and/or hydrates and/or solvates and/or polymorphs thereof.

In another aspect, the present invention relates to compounds of formula (V):

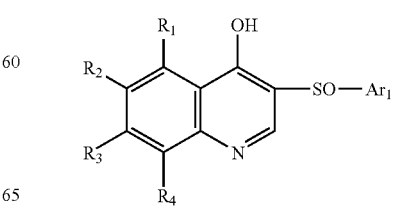

wherein

Ar₁ represents an optionally substituted phenyl or heteroaryl group; and

R₁, R₂, R₃ and R₄ represent independently a substituent selected from hydrogen, halogen, cyano, alkyl, alkoxy, hydroxy, trifluoromethyl, amino, alkylamino, dialkylamino, aminomethyl, alkylaminomethyl, dialkylaminomethyl, and/or salts and/or hydrates and/or solvates and/or polymorphs thereof.

In another aspect, the present invention relates to compounds of formula (VI):

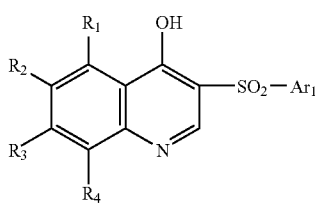
(VI)

wherein

Ar₁ represents an optionally substituted phenyl or heteroaryl group; and

R₁, R₂, R₃ and R₄ represent independently a substituent selected from hydrogen, halogen, cyano, alkyl, alkoxy, hydroxy, trifluoromethyl, amino, alkylamino, dialkylamino, aminomethyl, alkylaminomethyl, dialkylaminomethyl, and/or salts and/or hydrates and/or solvates and/or polymorphs thereof.

In another aspect, the present invention relates to compounds of formula (VII):

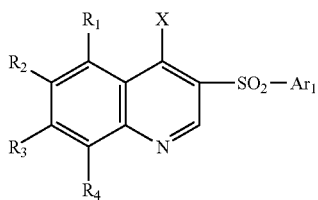
(VII)

wherein

X is chloro, bromo, benzenesulfonyloxy, 4-fluoro-benzenesulfonyloxy, 4-methyl-benzenesulfonyloxy, methanesulfonyloxy or trifluoromethanesulfonyloxy;

Ar₁ represents an optionally substituted phenyl or heteroaryl group; and

R₁, R₂, R₃ and 1 represent independently a substituent selected from hydrogen, halogen, cyano, alkyl, alkoxy, hydroxy, trifluoromethyl, amino, alkylamino, dialkylamino, aminomethyl, alkylaminomethyl, dialkylaminomethyl, and/or salts and/or hydrates and/or solvates and/or polymorphs thereof.

Synthetic Methods

The present invention also provides processes for preparing compounds of formula (I).

In one embodiment, the present invention is directed to a process for the preparation of compounds of formula (I):

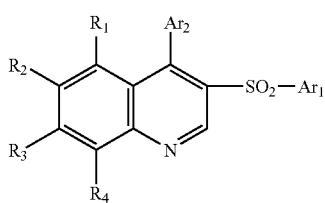
(I)

wherein

Ar₁ represents an optionally substituted phenyl or heteroaryl group;

Ar₂ represents a substituted phenyl or an optionally substituted heteroaryl group;

R₁, R₂, R₃ and 1 represent independently a substituent selected from hydrogen, halogen, cyano, alkyl, alkoxy, hydroxy, trifluoromethyl, amino, alkylamino, dialkylamino, aminomethyl, alkylaminomethyl, dialkylaminomethyl, said process involving (i) reacting a compound of formula (II):

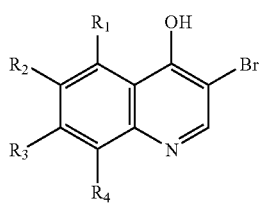
(II)

wherein R₁, R₂, R₃ and R₄ are as defined above for a compound of formula (I), with a compound of formula (III):

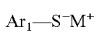
Ar₁—S⁻M⁺ (III)

wherein M is selected from alkali metals and alkaline-earth metals and Ar₁ is as defined above for compounds of formula (I), to afford a compound of formula (IV):

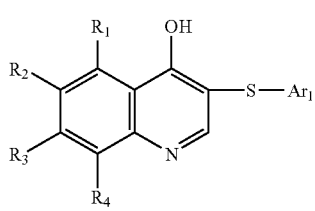
(IV)

wherein R₁, R₂, R₃, R₄ and Ar₁ are as defined above for compounds of formula (I), (ii) oxidizing the compound of formula (IV) to obtain a compound of formula (V):

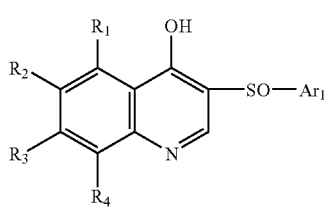
(V)

wherein R₁, R₂, R₃, R₄ and Ar₁ are as defined above for compounds of formula (I), (iii) oxidizing the compound of formula (V) to obtain a compound of formula (VI):

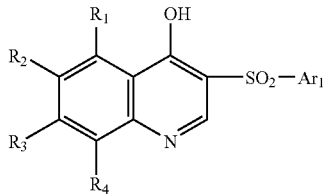
(VI)

wherein $R_1$, $R_2$, $R_3$, $R_4$ and $Ar_1$ are as defined above for compounds of formula (I), (iv) converting the compound of formula (VI) to a compound of formula (VII):

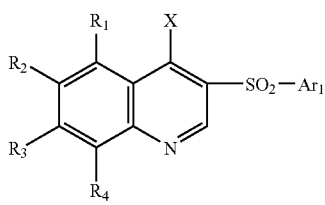
(VII)

wherein X is selected from chloro, bromo, benzenesulfonyloxy, 4-fluoro-benzenesulfonyloxy, 4-methyl-benzenesulfonyloxy, methanesulfonyloxy or trifluoromethanesulfonyloxy and $R_1$, $R_2$, $R_3$, $R_4$ and $Ar_1$ are as defined above for compounds of formula (I), (v) reacting the compound of formula (VII) with a boronic acid derivative of formula (VIII):

$$Ar_2—B(OH)_2 \quad (VIII)$$

in the presence of base (e.g. sodium carbonate) and catalyst (e.g. tetrakis(triphenylphosphine)-palladium(0)) in a solvent, and optionally thereafter forming salts and/or hydrates and/or solvates of the compound of formula (I).

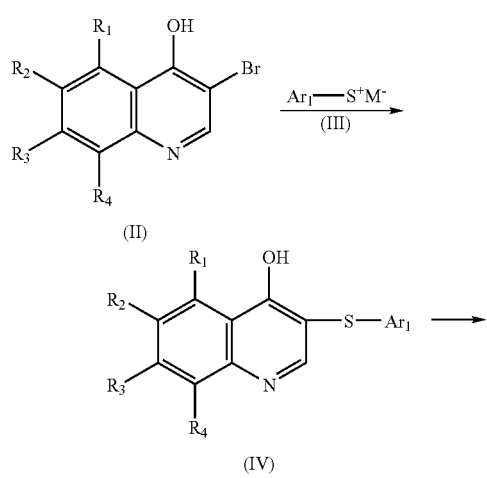

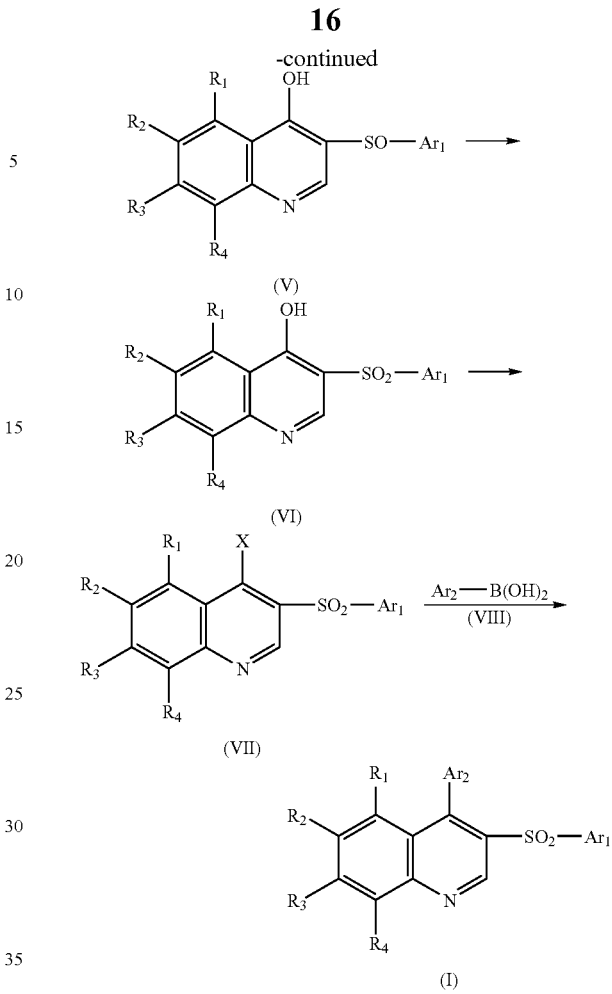

According to Scheme 1,3-Bromo-quinolin-4-ol derivatives of formula (II) can be reacted with alkali or alkaline-earth metal salts (e.g. sodium salt) of thiophenols of formula (III) to provide a compound of formula (IV) (see, e.g. *Bioorg. Med. Chem. Lett.*, 2001, 9, 1141). Advantageously the reaction may be carried out in the presence of palladium catalyst and under microwave conditions. 3-Bromo-quinolin-4-ol derivatives of formula (II) are known (e.g. 3-bromo-6-chloro-quinolin-4-ol: see *J. Chem. Soc.*, 1950, 384; 3-bromo-7-trifluoromethyl-quinolin-4-ol: see *Synthesis*, 1977, 865) or can be synthesised by conventional methods. Alkali or alkaline-earth metal salts of thiophenols of formula (III) are commercially available or can be prepared by conventional methods.

Oxidation of 3-arenesulfanyl-quinolin-4-ol derivatives of formula (IV) can be accomplished in a suitable acid (e.g. trifluoroacetic acid) with hydrogen peroxide to give sulfoxides of formula (V). Further oxidation of sulfoxides of formula (V) using similar reagents and conditions affords sulfones of formula (VI).

Conversion of 3-arenesulfonyl-quinolin-4-ol derivatives of formula (VI) to compounds of formula (VII) can be carried out by known halogenation methods with suitable reagents (e.g. $POCl_3$, $SOCl_2$, $PCl_5$, $POBr_3$, $PBr_3$), or by acylation with the appropriate sulfonic acid halogenide or sulfonic acid anhydride derivatives.

Another method to prepare intermediates of formula (VI) involves:

(i) reacting a compound of formula (IX):

$$Ar_1—SO_2Na \quad (IX)$$

wherein $Ar_1$ is as defined above for a compound of formula (I), with α-halogen-acetic acid esters of formula (X):

wherein Hlg is halogen and $R_5$ is an alkyl (e.g., ethyl or methyl) group, to obtain a compound of formula (XI):

wherein $Ar_1$ is as defined above for a compound of formula (I) and $R_5$ is as defined above for compounds of formula (X);
(ii) reacting the compound of formula (XI) with a trialkyl orthoformate of formula (XII):

$$CH(OR_6)_3 \quad (XII)$$

wherein $R_6$ is an alkyl (e.g., ethyl or methyl) group, to obtain a compound of formula (XIII):

wherein $Ar_1$ is as defined above for a compound of formula (I), $R_5$ is as defined above for compounds of formula (X) and $R_6$ is as defined above for compounds of formula (XII);
(iii) reacting the compound of formula (XIII) with an aniline derivative of formula (XIV):

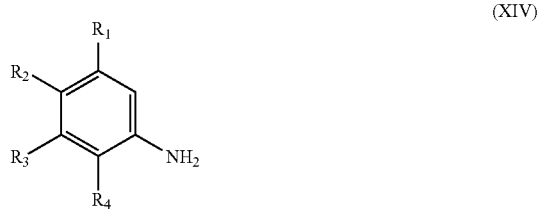

wherein $R_1$, $R_2$, $R_3$ and $R_4$ are as defined above for a compound of formula (I), to obtain a compound of formula (VI).

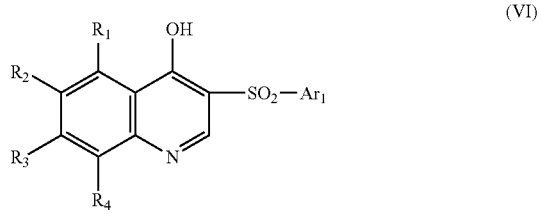

wherein $R_1$, $R_2$, $R_3$ and $R_4$ are as defined above for a compound of formula (I),
The compound of formula (VI) may then be converted to a compound of formula (I) as described above.

Scheme 2

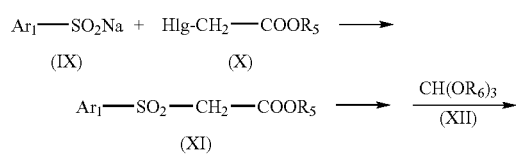

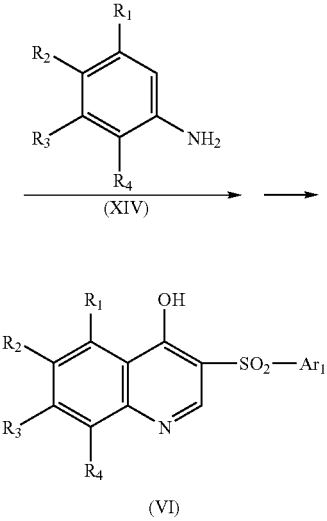

According to Scheme 2 compounds of formula (IX) are reacted with α-halogen-acetic acid esters of formula (X) in a suitable solvent (e.g. DMF, water). Compounds of formula (IX) are commercially available or can be prepared from the appropriate benzenesulfonyl chloride derivatives by known methods (see, e.g., *Org. Lett.*, 2003, 5(21), 3895). Compounds of formula (XIII) can be prepared by the reaction of compounds of formula (XI) and compounds of formula (XII) in the presence of acetic anhydride [see, e.g., *J. Org. Chem. USSR* (*Engl. Transl.*, 1980, 16(7), 1275; *Zh. Org. Khim.*, 1980, 16(7), 1483]. Reaction of compounds of formula (XIII) with aniline derivatives of compounds of formula (XIV) gives benzenesulfonyl-phenylamino-acrylic acid esters [see, e.g., *J. Org. Chem. USSR* (*Engl. Transl.*, 1980, 16(7), 1275; *Zh. Org. Khim.*, 1980, 16(7), 1483-1487] that can be converted in situ into quinolin-4-ol derivatives of formula (VI) (see analogous reaction: *J. Chem. Soc. Perkin Trans.*, 1, 1994, 4, 387-392).

Compounds of formula (I) contain basic function(s) and thus be transformed into salts thereof with acids and/or can be liberated from the obtained acid addition salts by treatment with a base.

Compounds of formula (I) can also be transformed into hydrates and/or solvates.

Compounds of formula (I) can optionally be intercoverted to a different compound of formula (I) by conventional synthetic methods.

Pharmaceutical Formulations

The invention also relates to the pharmaceutical compositions containing the compounds of formula (I) and/or salts and/or hydrates and/or solvates and/or polymorphs thereof as active ingredient and one or more physiologically acceptable carriers.

The compounds of formula (I) and/or salts and/or hydrates and/or solvates and/or polymorphs thereof may be administered by any convenient method, for example by oral, parenteral (including subcutaneous, intramuscular, and intravenous), buccal, sublingual, nasal, rectal or transdermal administration and the pharmaceutical compositions adapted accordingly.

The compounds of formula (I) and/or salts and/or hydrates and/or solvates and/or polymorphs thereof which are active when given orally can be formulated as liquids or solids, for example syrups, suspensions or emulsions, tablets, capsules and lozenges.

A liquid formulation of the compounds of formula (I) and/or salts and/or hydrates and/or solvates and/or polymorphs thereof is generally a suspension or solution of the compound of formula (I) and/or salts and/or hydrates and/or solvates and/or polymorphs thereof in a suitable liquid carrier(s) for example an aqueous solvent, such as water and ethanol or glycerine, or a non-aqueous solvent, such as polyethylene glycol or an oil. The formulation may also contain one or more suspending agent, preservative, flavouring or colouring agent or combinations thereof.

A composition in the solid form of a tablet can be prepared using any suitable pharmaceutical carrier(s) routinely used for preparing solid formulations. Examples of solid carriers include, for example, lactose, terra alba, sucrose, talc, gelatine, agar, pectin, acacia, magnesium stearate, stearic acid etc. Optionally, tablets may be coated by standard aqueous or nonaqueous techniques.

A composition in the solid form of a capsule can be prepared using routine encapsulation procedures. For example, pellets containing the active ingredient can be prepared using standard carriers and then these are filled into a hard gelatine capsule; alternatively, a dispersion or suspension can be prepared using any suitable pharmaceutical carrier(s), for example aqueous gums, celluloses, silicates or oils and the dispersion or suspension then is filled into a soft gelatine capsule.

Parenteral compositions are typically a solution or suspension of the compound of formula (I) and/or salts and/or hydrates and/or solvates and/or polymorphs thereof in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions of the present invention for nasal administration containing a compound of formula (I) and/or salts and/or hydrates and/or solvates and/or polymorphs thereof may conveniently be formulated as aerosols, drops, gels and powders. Aerosol formulations of the present invention typically comprise a solution or fine suspension of the compound of formula (I) and/or salts and/or hydrates and/or solvates and/or polymorphs thereof in a physiologically acceptable aqueous or non-aqueous solvent and are usually presented in a single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal once the contents of the container have been exhausted. If the dosage form comprises an aerosol dispenser, it will contain a propellant which can be a compressed gas, such as compressed air or an organic propellant, such as a fluorochlorohydrocarbon. The aerosol dosages form can also take the form of a pump-atomiser.

Compositions of the present invention containing a compound of formula (I) and/or salts and/or hydrates and/or solvates and/or polymorphs thereof are suitable for buccal or sublingual administration including tablets, lozenges and pastilles, wherein the active ingredient is formulated with a carrier, such as sugar and acacia, tragacanth, or gelatine, glycerin etc.

Compositions of the present invention containing a compound of formula (I) and/or salts and/or hydrates and/or solvates and/or polymorphs thereof for rectal administration are conveniently in the form of suppositories containing a conventional suppository base, such as cocoa butter and other materials commonly used in the art. The suppositories may be conveniently formed by first admixing the composition with the softened or melted carrier(s) followed by chilling and shaping in moulds.

Compositions of the present invention containing a compound of formula (I) and/or salts and/or hydrates and/or solvates and/or polymorphs thereof for transdermal administration include ointments, gels and patches.

A composition of the present invention containing a compound of formula (I) and/or salts and/or hydrates and/or solvates and/or polymorphs thereof is preferably in a unit dose form, such as tablet, capsule or ampoule.

Each dosage unit of the present invention for oral administration contains preferably from 0.1 to 500 mg of a compound of formula (I) and/or salts and/or hydrates and/or solvates and/or polymorphs thereof calculated as a free base.

Each dosage unit of the present invention for parenteral administration contains preferably from 0.1 to 500 mg of a compound of formula (I) and/or salts and/or hydrates and/or solvates and/or polymorphs thereof calculated as a free base.

The compounds of formula (I) and/or salts and/or hydrates and/or solvates and/or polymorphs thereof can normally be administered in a daily dosage regimen. In the treatment of mGluR1 and mGluR5 mediated disorders, such as, but not limited to, schizophrenia, anxiety, depression, panic, bipolar disorders, and circadian disorders or chronic and acute pain disorders the dosage levels from about 0.01 mg/kg to about 140 mg/kg of body weight per day are useful or alternatively about 0.5 mg to about 7 g per patient per day.

The amount of active ingredient that may be combined with the carrier materials to produce a single dosage form will vary depending upon the host treated and the particular mode of administration. For example, a formulation intended for the oral administration to humans may conveniently contain from about 0.5 mg to about 5 g of active agent, compounded with an appropriate and convenient amount of carrier material which may vary from about 5 to about 95 percent of the total composition. Unit dosage forms will generally contain between from about 1 mg to about 1000 mg of the active ingredient, typically 25 mg, 50 mg, 100 mg, 200 mg, 250-300 mg, 400 mg, 500 mg, 600 mg, 800 mg or 1000 mg.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

Medical Use

The compounds of formula (I) and/or salts and/or hydrates and/or solvates and/or polymorphs thereof have been found to exhibit biological activity at mGluR1 and mGluR5 receptors and are expected to be useful in the treatment and/or prevention of mGluR1 and mGluR5 mediated disorders.

It has been found that the compounds of formula (I) and/or salts and/or hydrates and/or solvates and/or polymorphs thereof exhibit a high degree of potency and selectivity for individual metabotropic glutamate receptor (mGluR) subtypes. In particular, the compounds are potent and selective for mGluR1 and mGluR5 receptors. Accordingly, the compounds are expected to be useful in the prevention and/or treatment of conditions associated with excitatory activation of mGluR1 and mGluR5 receptor and for inhibiting neuronal damage caused by excitatory activation of mGluR1 and mGluR5 receptor. The compounds may be used to produce an inhibitory effect of mGluR1 and mGluR5, in mammals, including, but not limited to, humans.

Thus, it is expected that the compounds of formula (I) and/or salts and/or hydrates and/or solvates and/or polymorphs thereof are well suited for the prevention and/or treatment of mGluR1 and mGluR5 receptor-mediated disorders such as, but not limited to, acute and chronic neurological and psychiatric disorders, chronic and acute pain disorders and neuromuscular dysfunctions of the lower urinary tract.

The dose required for the therapeutic or preventive treatment of a particular disorder will necessarily be varied depending on the host treated and the route of administration.

The invention relates to compounds of formula (I) and/or salts and/or hydrates and/or solvates and/or polymorphs thereof, for use in therapy.

The invention relates to compounds of formula (I) and/or salts and/or hydrates and/or solvates and/or polymorphs thereof, for use in prevention and/or treatment of mGluR1 and mGluR5 receptor-mediated disorders.

The invention relates to compounds of formula (I) and/or salts and/or hydrates and/or solvates and/or polymorphs thereof, for use in prevention and/or treatment of neurological disorders.

The invention relates to compounds of formula (I) and/or salts and/or hydrates and/or solvates and/or polymorphs thereof, for use in prevention and/or treatment of psychiatric disorders.

The invention relates to compounds of formula (I) and/or salts and/or hydrates and/or solvates and/or polymorphs thereof, for use in prevention and/or treatment of chronic and acute pain disorders.

The invention relates to compounds of formula (I) and/or salts and/or hydrates and/or solvates and/or polymorphs thereof, for use in prevention and/or treatment of neuromuscular dysfunctions of the lower urinary tract.

The invention relates to compounds of formula (I) and/or salts and/or hydrates and/or solvates and/or polymorphs thereof, for use in prevention and/or treatment of pain related to migraine, inflammatory pain, neuropathic pain disorders such as diabetic neuropathies, arthritis and rheumatoid diseases, low back pain, post-operative pain and pain associated with various conditions including angina, in renal or biliary colic, menstruation, migraine and gout.

The invention relates to compounds of formula (I) and/or salts and/or hydrates and/or solvates and/or polymorphs thereof, for use in prevention and/or treatment of Alzheimer's disease senile dementia, AIDS-induced dementia Parkinson's disease, amyotrophic lateral sclerosis, Huntington's Chorea, migraine, epilepsy, schizophrenia, depression, anxiety, acute anxiety, obesity, obsessive compulsive disorder, opthalmological disorders such as retinopathies, diabetic retinopathies, glaucoma, auditory neuropathic disorders such as tinnitus, chemotherapy induced neuropathies, post-herpetic neuralgia and trigeminal neuralgia, tolerance, substance abuse and withdrawal, Fragile X, autism, mental retardation, schizophrenia and Down's Syndrome.

The invention relates to compounds of formula (I) and/or salts and/or hydrates and/or solvates and/or polymorphs thereof, for use in prevention and/or treatment of stroke, head trauma, anoxic and ischemic injuries, hypoglycemia, cardiovascular diseases and epilepsy.

The compounds of formula (I) and/or salts and/or hydrates and/or solvates and/or polymorphs thereof, are also well suited for the treatment of neuromuscular dysfunction of the lower urinary tract, such as urinary urgency, overactive bladder, greater urinary frequency, reduced urinary compliance, cystitis, incontinence, enuresis and dysuria.

The compounds of formula (I) and/or salts and/or hydrates and/or solvates and/or polymorphs thereof, are also well suited for the treatment of gastrointestinal disorders, such as transient lower esophageal sphincter relaxation (TLESR), gastrointestinal reflux disease and irritable bowel syndrome.

The present invention relates also to the use of a compound of formula (I) and/or salts and/or hydrates and/or solvates and/or polymorphs thereof, in the manufacture of a medicament for the prevention and/or treatment of mGluR1 and mGluR5 receptor-mediated disorders and any disorder listed above.

The invention also provides a method of treatment and/or prevention of mGluR1 and mGluR5 receptor mediated disorders and any disorder listed above, in a patient suffering from, or at risk of, said condition, which comprises administering to the patient an effective amount of a compound of formula (I) and/or salts and/or hydrates and/or solvates and/or polymorphs thereof.

In the context of the present specification, the term "therapy" includes treatment as well as prevention, unless there are specific indications to the contrary. The terms "therapeutic" and "therapeutically" should be construed accordingly.

In this specification, unless stated otherwise, the term "antagonist" means a compound that by any means, partly or completely blocks the transduction pathway leading to the production of a response by the ligand.

The term "disorder", unless stated otherwise, means any condition and disease associated with metabotropic glutamate receptor activity.

EXAMPLES

The present invention will now be further described by way of the following non-limiting examples. In applying the disclosure of these examples, it should be kept clearly in mind that the examples are merely illustrative of the present invention and should not be construed as limiting the scope of the invention in any way as many variations and equivalents that are encompassed by the present invention will become apparent to those skilled in the art upon reading the present disclosure All starting materials are either commercially available or can be synthesized by different known methods described in the literature.

Unless specifically stated otherwise, all operation were carried out at room temperature, that is at a temperature range of 18-25° C. The course of reactions was followed by thin layer chromatography (TLC) and reaction times are given for illustration only. The structure of all intermediates and end products were elucidated by IR, NMR and MS spectroscopy. When given yields are for illustration only. When given, NMR data are in the form of delta (δ) values for major diagnostic protons, given in parts per million (ppm) relative to tetramethylsilane (TMS) as internal standard, using the indicated solvent. Conventional abbreviations are used for signal shape.

Example 1

4-(4-chloro-phenyl)-3-(4-methyl-benzenesulfonyl)-quinoline

Table I, compound 1

3-(4-Methyl benzenesulfanyl)-quinolin-4-ol

A mixture of 3-bromo-quinolin-4-ol (0.448 g, 2 mmol; *J. Am. Chem. Soc.* 1946, 68, 1229-1231), 4-methylbenzenethiol (0.30 g, 2.4 mmol), tetrakis-(triphenylphosphin)palladium(0)

(0.115 g, 0.1 mmol), sodium-tert-butylate (0.23 g, 2.4 mmol) and DMF (2.0 ml) was stirred and irradiated at 142° C. for 3 hours in a 8-ml microwave vial. The solvent was evaporated in vacuo and the residue was purified by gradient silica gel flashchromatography (80 g silica gel, eluent A: chloroform, eluent B: chloroform:methanol=95:5) to give 0.33 g of the title compound in 62% yield.

MS (EI) $M^+$=268.2

3-(4-Methyl-benzenesulfonyl)-quinolin-4-ol

To a mixture of 3-(4-Methyl-benzenesulfanyl)-quinolin-4-ol (0.25 g, 0.936 mmol) and trifluoroacetic acid (5.0 ml) a solution of hydrogen peroxide in trifluoroacetic acid (c=3.0M, 3.7 ml) was added dropwise. The solution was stirred for 8 hours at room temperature. To the reaction mixture 6 ml of water was added dropwise. The precipitate was filtered off, washed with water and dried in vacuo to give 0.24 g of the title compound in 86%.

MS (EI) $M^+$=300.1

4-Chloro-3-(4-methyl-benzenesulfonyl)-quinoline

A mixture of 3-(4-methyl-benzenesulfonyl)-quinolin-4-ol (0.24 g, 0.8 mmol) and phosphorus(V) oxychloride (15 ml) was refluxed for 5 hours. Phosphorus(V) oxychloride was distilled off, and the residue was poured onto ice. The slurry was stirred for 2 hours at 0-5° C., neutralized with sodium carbonate and extracted with chloroform (50 ml). The organic layer was dried over anhydrous sodium sulfate, filtered and the solvent was removed in vacuo to give 0.23 g of the title compound in 90% yield.

MS (EI) $M^+$=318.2

4-(4-chloro-phenyl)-3-(4-methyl-benzenesulfonyl)-quinoline

A mixture of 4-chloro-3-(4-methyl-benzenesulfonyl)-quinolin-4-ol (0.2 g, 0.67 mmol) and 4-chlorophenylboronic acid (0.16 g, 1.0 mmol) in 8 ml dioxane was stirred for 20 hours at 90° C. with potassium carbonate (0.5 g, 3.6 mmol) and tetrakis-(triphenylphosphin)palladium(0) (0.04 g, 0.035 mmol). After cooling the mixture was concentrated in vacuo. The crude residue was purified by column chromatography on silica gel (Kieselgel 60, eluent: chloroform) to obtain 0.21 g of the title compound in 80% yield.

$^1$H NMR (500 MHz, DMSO-$d_6$): 9.61 (s, 1H); 8.21 (dm, J=8.6 Hz, 1H); 7.98 (ddd, J=8.5, 6.8, 1.4 Hz, 1H); 7.64 (ddd, J=8.5, 6.8, 1.2 Hz, 1H); 7.49-7.44 (m, 2H); 7.37-7.32 (m, 2H); 7.30-7.24 (m, 3H); 7.04-6.98 (m, 2H); 2.36 (s, 3H).

MS (EI) $M^+$=393.8

4-(4-chloro-phenyl)-3-(4-methyl-benzenesulfonyl)-quinoline hydrochloride 4-(4-chloro-phenyl)-3-(4-methyl-benzenesulfonyl)-quinoline (40 mg, 0.102 mmol) was dissolved in ethyl acetate (1.5 ml) and a solution of hydrogen chloride in ethyl acetate (c=1.6M, 0.14 ml, 0.224 mmol) was added dropwise to the solution. The solid was filtered off, washed with ethyl acetate and dried in vacuo to give 35 mg of the title compound in 80% yield.

$^1$H NMR (500 MHz, DMSO-$d_6$): 9.61 (s, 1H); 8.22 (dm, J=8.6 Hz, 1H); 7.98 (ddd, J=8.6, 6.8, 1.4 Hz, 1H); 7.64 (ddd, J=8.6, 6.8, 1.2 Hz, 1H); 7.50-7.43 (m, 2H); 7.37-7.31 (m, 2H); 7.31-7.23 (m, 3H); 7.05-6.98 (m, 2H); 2.36 (s, 3H).

MS (EI) $M^+$=393.8

Example 2

(4-Chloro-benzenesulfonyl)-acetic acid methyl ester (intermediate)

A mixture of methyl bromoacetate (11.25 ml, 116 mmol) and sodium 4-chloro-benzenesulfinate (25.2 g, 116 mmol) in DMF (120 ml) was stirred and heated at 80° C. for 2 h. The solution was diluted with water (360 ml). The separated oil was extracted with chloroform (200 ml) and washed with water (3×80 ml). The organic phase was evaporated in vacuo to obtain 22.4 g of the title compound in 77.7% yield.

MS (EI) $M^+$=249.1.

Applying the above procedure the following compounds were prepared: e.g. (3-chloro-benzenesulfonyl)-acetic acid methyl ester (MS (EI) $M^+$=249.1); (3,5-dichloro-benzenesulfonyl)-acetic acid methyl ester (MS (EI) $M^+$=283.1); (4-methoxy-benzenesulfonyl)-acetic acid methyl ester (MS (EI) $M^+$=245.1); (3-chloro-4-fluoro-benzenesulfonyl)-acetic acid methyl ester (MS (EI) $M^+$=267.1); (3,5-difluoro-benzenesulfonyl)-acetic acid methyl ester (MS (EI) $M^+$=251.1); (3-fluoro-benzenesulfonyl)-acetic acid methyl ester (MS (EI) $M^+$=233.2).

Example 3

2-(4-Chloro-benzenesulfonyl)-3-ethoxy-acrylic acid methyl ester (intermediate)

The mixture of (4-chloro-benzenesulfonyl)-acetic acid methyl ester (22.4 g, 90 mmol), triethyl orthoformate (33.2 ml, 216 mmol) and acetic anhydride (19.1 ml, 203 mmol) was refluxed for 3 h with simultaneous distillation of ethanol, triethyl orthoformate and acetic anhydride, and then evaporated to dryness. The crude material (22.7 g, 82.8%) was used in the next step without purification.

MS (EI) $M^+$=305.1.

Applying the above procedure the following compounds were prepared: e.g. 2-(3-chloro-benzenesulfonyl)-3-ethoxy-acrylic acid methyl ester (MS (EI) $M^+$=305.1); 2-(3-chloro-4-fluoro-benzenesulfonyl)-3-ethoxy-acrylic acid methyl ester (MS (EI) $M^+$=323.1); 2-(3,5-dichloro-benzenesulfonyl)-3-ethoxy-acrylic acid methyl ester (MS (EI) $M^+$=340.1); 2-(4-fluoro-benzenesulfonyl)-3-ethoxy-acrylic acid methyl ester (MS (EI) $M^+$=289.1); 2-(3-cyano-5 fluoro-benzenesulfonyl)-3-ethoxy-acrylic acid methyl ester (MS (EI) $M^+$=314.2).

Example 4

7-Chloro-3-(4-chloro-benzenesulfonyl)-quinolin-4-ol (intermediate)

The mixture of 2-(4-chloro-benzenesulfonyl)-3-ethoxy-acrylic acid methyl ester (7.62 g, 25 mmol) and 3-chloroaniline (3.19 g, 25 mmol) in diphenyl ether (20 ml) was heated at near reflux for 1 h. After cooling the precipitate was filtered and washed with ether to obtain 4.25 g of the title compound in 48.0% yield.

MS (EI) $M^+$=355.1.

Applying the above procedure the following compounds were prepared: e.g. 8-chloro-3-(4-chloro-benzenesulfonyl)-quinolin-4-ol (MS (EI) $M^+$=355.1); 6-chloro-3-(4-fluoro-benzenesulfonyl)-quinolin-4-ol (MS (EI) $M^+$=338.1); 6-cyano-3-(4-fluoro-benzenesulfonyl)-quinolin-4-ol (MS (EI)

M⁺=329.2); 8-chloro-3-(3,4-dichloro-benzenesulfonyl)-quinolin-4-ol (MS (EI) M$^+$=390.1); 7-chloro-3-(3,5-difluoro-benzenesulfonyl)-quinolin-4-ol (MS (EI) M$^+$=356.1).

Example 5

3-(4-chloro-benzenesulfonyl)-4,7-dichloroquinoline (intermediate)

7-Chloro-3-(4-chloro-benzenesulfonyl)-4-hydroxyquinoline (4.25 g, 12 mmol) in phosphorus(V) oxychloride (5.6 ml, 60 mmol) was refluxed for 3 h. The reaction mixture was poured into water (50 ml) and was alkalized with 5M sodium hydroxyde solution. After cooling the precipitate was filtered and washed with water to obtain 3.8 g of the title compound in 85.0% yield.

MS (EI) M$^+$=373.2.

Applying the above procedure the following compounds were prepared: e.g. 3-(3-chloro-benzenesulfonyl)-4,6-dichloroquinoline (MS (EI) M$^+$=373.2); 3-(4-chloro-benzenesulfonyl)-4,8-dichloroquinoline (MS (EI) M$^+$=373.2); 4-chloro-6-cyano-3-(4-fluoro-benzenesulfonyl)-quinoline (MS (EI) M$^+$=347.1); 4-chloro-3-(4-chloro-benzenesulfonyl)-6-fluoro-quinoline (MS (EI) M$^+$=357.1).

Example 6

4-bromo-7-chloro-3-(4-chloro-benzenesulfonyl)-quinoline (intermediate)

A mixture of 7-chloro-3-(4-chloro-benzenesulfonyl)-quinolin-4-ol (0.5 g, 1.41 mmol) and phosphorus(V) oxybromide (1.2 g, 4.2 mmol) in chloroform (30 ml) and triethylamine (1 ml) was refluxed for 6 hours. The reaction mixture was diluted with water (30 ml) and the pH was adjusted to 10 with aqueous sodium hydroxide solution. The organic layer was separated, dried over sodium sulfate, filtered, and concentrated in vacuo. The obtained crude product was purified by crystallization from diethyl ether to obtain 0.45 g of the title compound in 77% yield.

MS (EI) M$^+$=418.1.

Applying the above procedure the following compounds were prepared: e.g. 4-bromo-3-(4-chloro-benzenesulfonyl)-6-fluoro-quinoline (MS (EI) M$^+$=347.1); 4-bromo-7-chloro-3-(3,5-difluoro-benzenesulfonyl)-quinoline (MS (EI) M$^+$=420.1); 4-bromo-7-chloro-3-(4-chloro-benzenesulfonyl)-6-fluoro-quinoline (MS (EI) M$^+$=436.1); 4-bromo-7-chloro-3-(4-fluoro-benzenesulfonyl)-quinoline (MS (EI) M$^+$=402.1); 4-bromo-7-chloro-3-(3-fluoro-benzenesulfonyl)-quinoline (MS (EI) M$^+$=402.1); 4-bromo-7-chloro-3-(3-cyano-benzenesulfonyl)-quinoline (MS (EI) M$^+$=409.2); 4-bromo-7-chloro-3-(3-cyano-5-fluoro-benzenesulfonyl)-quinoline (MS (EI) M$^+$=427.1).

Example 7

7-chloro-3-(4-chloro-benzenesulfonyl)-4-(4-fluoro-phenyl)-quinoline

Table I compound 4

A mixture of 4-bromo-7-chloro-3-(4-chloro-benzenesulfonyl)-quinoline (0.42 g, 1 mmol), 4-fluorophenylboronic acid (0.21 g, 1.5 mmol) and tetrakis-(triphenylphosphin)palladium(0) (0.08 g, 0.07 mmol) in 30 ml 1,2-dimethoxyethane and 8 ml of 2M aqueous sodium carbonate solution was stirred for 2 hours at 70° C. After cooling the mixture was concentrated in vacuo. The crude residue was purified by column chromatography on silica gel (Kieselgel 60, eluent: chloroform) and crystallized from methanol to obtain 0.29 g of the title compound in 67% yield.

$^1$H NMR (400 MHz, DMSO-d$_6$): 6.92-6.98 m (2H) [H-14, 18]; 7.06-7.13 m (2H) [H-15,17]; 7.25-7.32 m (5H) [H-6, 22,23,25, 26]; 7.44 dd (1H) [H-7]; 9.23 d (1H) [H-9]; 9.77 s (1H) [H-2]

MS (EI) M$^+$=433.2

Applying the above procedure the following compounds were prepared: e.g.
7-fluoro-3-(4-fluoro-benzenesulfonyl)-4-(3-fluoro-phenyl)-quinoline (Table I compound 9, MS (EI) M$^+$=400.2),
4-(3-chloro-phenyl)-3-(3,4-dimethyl-benzenesulfonyl)-7-fluoro-quinoline (Table I compound 17, MS (EI) M$^+$=426.2),
4-(4-chloro-phenyl)-3-(3,5-difluoro-benzenesulfonyl)-7-fluoro-quinoline (Table I compound 35, MS (EI) M$^+$=434.2),
4-(3-chloro-phenyl)-8-fluoro-3-(4-methoxy-benzenesulfonyl)-quinoline (Table I compound 53, MS (EI) M$^+$=428.2),
3-(3-cyano-benzenesulfonyl)-6-fluoro-4-(3-methoxy-phenyl)-quinoline (Table I compound 68, MS (EI) M$^+$=419.3),
3-(3,4-difluoro-benzenesulfonyl)-7-fluoro-4-(4-fluoro-phenyl)-quinoline (Table I compound 101, MS (EI) M$^+$=418.2),
7-chloro-3-(3,4-difluoro-benzenesulfonyl)-4-(3-fluoro-phenyl)-quinoline (Table I compound 170, MS (EI) M$^+$=434.2),
7-chloro-3-(3-cyano-5-fluoro-benzenesulfonyl)-4-(4-fluoro-phenyl)-quinoline (Table I compound 186, MS (EI) M$^+$=441.2).

Example 8

Preparation of Pharmaceutical Compositions a) Tablets:

0.01-50% of active ingredient of formula (I), 15-50% of lactose, 15-50% of potato starch, 5-15% of polyvinyl pyrrolidone, 1-5% of talc, 0.01-3% of magnesium stearate, 1-3% of colloid silicon dioxide and 2-7% of ultraamylopectin are mixed, then granulated by wet granulation and pressed to tablets.

b) Dragées, film coated tablets:

The tablets made according to the method described above are coated by a layer consisting of entero- or gastrosolvent film, or of sugar and talc. The dragées are polished by a mixture of beeswax and carnuba wax.

c) Capsules:

0.01-50% of active ingredient of formula (I), 1-5% of sodium lauryl sulfate, 15-50% of starch, 15-50% of lactose, 1-3% of colloid silicon dioxide and 0.01-3% of magnesium stearate are thoroughly mixed, the mixture is passed through a sieve and filled in hard gelatin capsules.

d) Suspensions:

Ingredients: 0.01-15% of active ingredient of formula (I), 0.1-2% of sodium hydroxide, 0.1-3% of citric acid, 0.05-0.2% of nipagin (sodium methyl 4-hydroxybenzoate), 0.005-0.02% of nipasol, 0.01-0.5% of carbopol (polyacrilic acid), 0.1-5% of 96% ethanol, 0.1-1% of flavoring agent, 20-70% of sorbitol (70% aqueous solution) and 30-50% of distilled water.

To solution of nipagin and citric acid in 20 ml of distilled water, carbopol is added in small portions under vigorous stirring, and the solution is left to stand for 10-12 h. Then the sodium hydroxide in 1 ml of distilled water, the aqueous solution of sorbitol and finally the ethanolic raspberry flavor were added with stirring. To this carrier the active ingredient is added in small portions and suspended with an immersing homogenizator. Finally the suspension is filled up to the desired final volume with distilled water and the suspension syrup was passed through a colloid milling equipment.

e) Suppositories:

For each suppository 0.01-15% of active ingredient of formula (I) and 1-20% of lactose are thoroughly mixed, then 50-95% of adeps pro suppository (for example Witepsol 4) is melted, cooled to 35° C. and the mixture of active ingredient and lactose is mixed in it with homogenizator. The obtained mixture was mould in cooled forms.

f) Lyophilized Powder Ampoule Compositions:

A 5% solution of mannitol or lactose is made with bidistilled water for injection use, and the solution is filtered so as to have sterile solution. A 0.01-5% solution of the active ingredient of formula (I) is also made with bidistilled water for injection use, and this solution is filtered so as to have sterile solution. These two solutions are mixed under aseptic conditions, filled in 1 ml portions into ampoules, the content of the ampoules is lyophilized, and the ampoules are sealed under nitrogen. The contents of the ampoules are dissolved in sterile water or 0.9% (physiological) sterile aqueous sodium chloride solution before administration.

Example 9

3-(3,4-Difluoro-benzenesulfonyl)-7-nitro-quinolin-4-ol (intermediate)

The title compound was prepared applying the procedure described in Example 4 from 2-(3,4-difluoro-benzenesulfonyl)-3-ethoxy-acrylic acid methyl ester (3.49 g, 11.4 mmol) and 3-nitroaniline (1.57 g, 11.4 mmol). The yield was 1.6 g (38.3%).

MS (EI) $M^+$=367.2.

In the same way was prepared: e.g. 3-(3-cyano-5-fluoro-benzenesulfonyl)-8-nitro-quinolin-4-ol (MS (EI) $M^+$=374.3).

Example 10

4-Bromo-3-(3,4-difluoro-benzenesulfonyl)-7-nitro-quinoline (intermediate)

A mixture of 3-(3,4-difluoro-benzenesulfonyl)-7-nitro-quinolin-4-ol (1.6 g, 4.37 mmol) and phosphorus(V) oxybromide (2.5 g, 8.72 mmol) in DMF (16 ml) was stirred at 65° C. for 1 hour. The reaction mixture was diluted with water (100 ml) and the pH was adjusted to 10 with aqueous sodium hydroxide solution. After cooling the precipitate was filtered and washed with water. The obtained crude product was purified by crystallization from ethanol to obtain 1.25 g of the title compound in 67% yield.

MS (EI) $M^+$=430.9.

Applying the above procedure the following compound was prepared: e.g. 4-bromo-3-(3-cyano-5-fluoro-benzenesulfonyl)-8-nitro-quinoline (MS (EI) $M^+$=437.2).

Example 11

3-(3,4-Difluoro-benzenesulfonyl)-4-(3-fluoro-phenyl)-7-nitro-quinoline (intermediate)

The title compound was prepared applying the procedure described in Example 7 from 4-Bromo-3-(3,4-difluoro-benzenesulfonyl)-7-nitro-quinoline (0.53 g, 1.23 mmol) and 3-fluorophenylboronic acid (0.21 g, 1.5 mmol). The crude product was purified by column chromatography on silica gel (Kieselgel 60, eluent: chloroform) and crystallized from methanol to obtain 0.31 g of the title compound in 57% yield.

MS (EI) $M^+$=445.3.

In the same way were prepared: e.g. 3-(3-cyano-5-fluoro-benzenesulfonyl)-4-(4-fluoro-phenyl)-8-nitro-quinoline (MS (EI) $M^+$=452.3); 3-(3-cyano-5-fluoro-benzenesulfonyl)-4-(3-fluoro-phenyl)-8-nitro-quinoline (MS (EI) $M^+$=452.3).

Example 12

7-Amino-3-(3,4-difluoro-benzenesulfonyl)-4-(3-fluoro-phenyl)-quinoline

Table I compound 264

A mixture of 3-(3,4-difluoro-benzenesulfonyl)-4-(3-fluoro-phenyl)-7-nitro-quinoline (0.31 g, 0.69 mmol) and iron powder (0.15 g, 2.6 mmol) in acetic acid was stirred for 30 minutes at 60° C. The reaction mixture was diluted with water (5 ml). The precipitate was filtered and washed with water (2×5 ml). The obtained crude product was purified by crystallization from methanol to obtain 0.12 g of the title compound in 42% yield.

MS (EI) $M^+$=415.1.

Applying the above procedure the following compounds were prepared: e.g. 7-amino-3-(3-chloro-5-fluoro-benzenesulfonyl)-4-(4-fluoro-phenyl)-quinoline (MS (EI) $M^+$=422.1); 7-amino-3-(3-chloro-5-fluoro-benzenesulfonyl)-4-(3-fluoro-phenyl)-quinoline (MS (EI) $M^+$=422.1)

Biological Test Methods

MGluR1 Receptor Binding Test

MGluR1 receptor binding tests were performed according to modified method of Lavreysen et al. (Mol. Pharm., 2003, 63, 1082). Based on the high homology between the human and rat mGluR1 receptors, rat cerebellar membrane preparation was used to determine the binding characteristics of reference compounds and novel compounds to the rat mGluR1. [3H]R214127 (3 nM) was used as radioligand and the nonspecific binding was determined in the presence of 1 μM of R214127.

IC-50 values were determined from displacement curves by nonlinear regression analysis and were converted to Ki values using the equation method of Cheng and Prusoff (Biochem. Pharmacol., 1973, 22, 3099).

MGluR5 Receptor Binding Tests

MGluR5 receptor binding was determined according to the method of Gasparini et. al. (Bioorg. Med. Chem. Lett. 2000, 12:407-409) with modifications. Rat cerebro-cortical membrane preparation was used to determine the binding characteristics of reference compounds and novel compounds to the rat mGluR5. The A18 cell line expressing hmGluR5a (purchased from Euroscreen) was used to determine binding characteristics of the chemical compounds to the human mGluR5a receptor. [3H]-M-MPEP (2 nM) was used as radioligand. The nonspecific binding was determined in the presence of 10 μM M-MPEP.

Assessment of Functional Activity

Cell Cultures for Native Rat mGluR5 and mGluR1 Receptors

Functional potency at native rat mGluR5 and mGluR1 receptors was estimated using primary neocortical cell cultures derived from 17 day old Charles River rat embryos and primary cerebellar cell cultures derived from 4-day old Wistar rats, respectively. For details on the preparation of neural cell cultures see Johnson, M. I.; Bunge, R. P. (1992): Primary cell cultures of peripheral and central neurons and glia. In: Protocols for Neural Cell Culture, eds: Fedoroff, S.; Richardson A., The Humana Press Inc., 51-77. After isolation the cells were plated onto standard 96-well microplates and the cultures were maintained in an atmosphere of 95% air-5% $CO_2$ at 37° C. The neocortical and cerebellar cultures were used for the calcium measurements after 5-7 and 3-4 days in vitro, respectively.

Cell Cultures for Recombinant Human mGluR5a Receptors

Chinese hamster ovary (CHO) cells stably expressing recombinant human mGluR5a (CHO-mGluR5a, purchased from Euroscreen) receptors were cultured in F12 medium containing 10% FCS, 1% antibiotic antimycotic solution, 400 µg/ml G418, 250 µg/ml zeocin, 5 µg/ml puromycin. Cells were kept at 37° C. in a humidified incubator in an atmosphere of 5% $CO_2$/95% air and were passaged three times a week. Cells were plated at 2.5-3.5×104 cell/well on standard 96-well microplates, receptor expression was induced by adding 600 ng/ml doxycycline on the next day. The calcium measurements were carried out 16-24 hours after the addition of the inducing agent.

Fluorimetric Measurement of Cytosolic Calcium Concentration

Measurements of cytosolic calcium concentration ($[Ca^{2+}]_i$) were carried out on primary neocortical and cerebellar cultures, and on CHO-mGluR5a cells stably expressing human mGluR5a receptors. Cells were grown in standard 96-well microplates and before the measurement were loaded with a fluorescent $Ca^{2+}$-sensitive dye, fluo-4/AM (2 µM): the neural cultures were loaded in their growth medium, CHO-mGluR5a cells were loaded in assay buffer (145 mM NaCl, 5 mM KCl, 2 mM $MgCl_2$, 2 mM $CaCl_2$, 10 mM HEPES, 20 mM D-glucose, 2 mM probenecid, pH=7.4) supplemented with 2 mM Na-pyruvate and 30 µg/ml glutamate-pyruvate transaminase (in case of CHO-mGluR5a cells these supplements were also present during the course of the $[Ca^{2+}]_i$ measurements). Loading was done by incubating the cells with 100 µl/well dye solution at 37° C. in a humidified incubator in an atmosphere of 5% CO2/95% air for 40-120 min. To stop dye loading cells were washed twice with assay buffer. After washing, various concentrations of the test compounds (diluted in assay buffer from a DMSO or a dimethylformamide (DMF) stock solution, final DMSO/DMF concentration was <0.1%) or buffer were added to each well depending on the experimental setup. In the case of neocortical cultures the assay buffer also contained TTX (0.5 µM, to suppress spontaneous oscillations of [Ca2+]i, in the case of cerebellar cultures probenecid was substituted with sulfinpyrazone (0.25 mM).

After incubation at 37° C. for 10-20 min. baseline and agonist-evoked changes of [Ca2+]i were measured column by column with a plate reader fluorimeter (FlexStation II, Molecular Devices). Excitation and detection of emission was carried out from the bottom of the plate. The whole measurement process was performed at 37° C. and was controlled by custom software. Inhibitory potency of the test compounds was assessed by measuring the reduction in the agonist-evoked $[Ca^{2+}]_i$-elevation in the presence of different concentrations of the compounds. DHPG was used as agonist for all three cultures, the concentration was 20 and 100 µM for neocortical and cerebellar cultures, respectively. In the case of CHO-mGluR5a cells DHPG was applied at an EC80 concentration, the EC80-values were derived from daily determined dose-response curves. Fluorescence data were expressed as ΔF/F (fluorescence change normalized to baseline).

All treatments on a single plate were measured in multiple wells. Data from all wells with the same treatment were averaged and the average values were used for analysis. Inhibitory potency of a compound at a single concentration point was expressed as percent inhibition of the control agonist response. Sigmoidal concentration-inhibition curves were fitted to the data (derived from at least three independent experiments) and IC50-values were determined as the concentration that produces half of the maximal inhibition caused by the compound. Raw fluorescence data were analyzed using Soft Max Pro (Molecular Devices), curve fitting was done with GraphPad Prism.

Results

Compounds of formula (I) of the present invention showed affinity for both rat and human mGluR1 and mGluR5 receptors and proved to be functional antagonists that inhibited functional responses elicited by stimulation of mGluR5 receptors.

Examples of compounds of formula (I) and their affinity for rat mGluR1 and mGluR5 receptors are given in the table below.

TABLE 1

| Comp. No. | Structure | $(M + H)^+$ or $M^+$ | mGlu5 $K_i$ (nM) | mGlu1 $K_i$ (nM) |
|---|---|---|---|---|
| 1. | 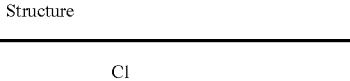 | 393.8 | * |  |

TABLE 1-continued

| Comp. No. | Structure | (M + H)+ or M+ | mGlu5 K$_i$ (nM) | mGlu1 K$_i$ (nM) |
|---|---|---|---|---|
| 2. | 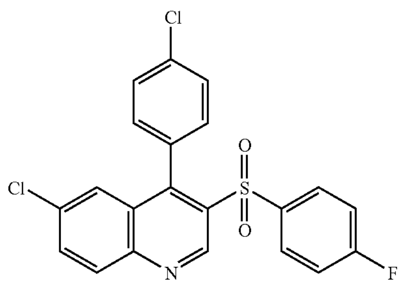 | 433.2 | * | * |
| 3. | 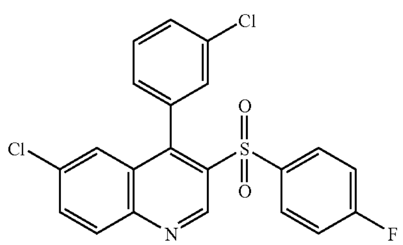 | 433.2 | * | * |
| 4. | 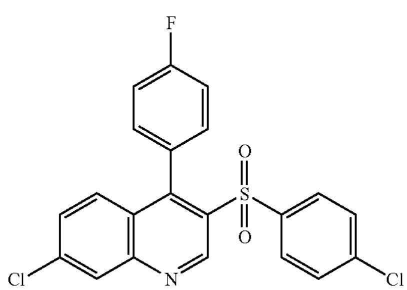 | 433.2 | * |  |
| 5. | 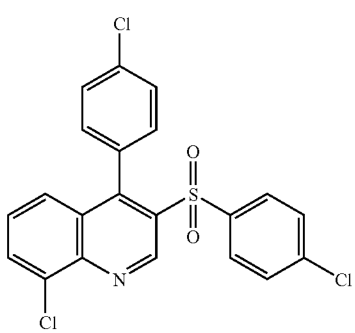 | 450.1 | ** | * |
| 6. | 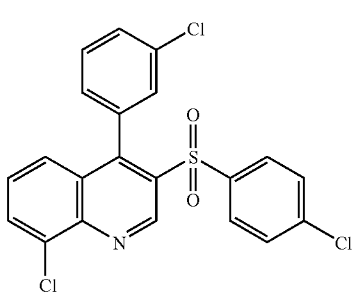 | 450.1 | ** | * |

TABLE 1-continued

| Comp. No. | Structure | (M + H)+ or M+ | mGlu5 K$_i$ (nM) | mGlu1 K$_i$ (nM) |
|---|---|---|---|---|
| 7. | 4-(3-chlorophenyl)-8-chloro-3-[(3,4-dichlorophenyl)sulfonyl]quinoline | 484.1 | *** | *** |
| 8. | 4-(3-chlorophenyl)-6-fluoro-3-[(4-chlorophenyl)sulfonyl]quinoline | 433.2 | * | * |
| 9. | 4-(3-fluorophenyl)-7-fluoro-3-[(4-fluorophenyl)sulfonyl]quinoline | 400.2 | *** | ** |
| 10. | 4-(4-methoxyphenyl)-7-fluoro-3-[(4-fluorophenyl)sulfonyl]quinoline | 412.2 | ** | * |
| 11. | 4-(4-chlorophenyl)-7-fluoro-3-[(4-methoxyphenyl)sulfonyl]quinoline | 428.2 | *** | * |

TABLE 1-continued
| Comp. No. | Structure | (M + H)+ or M+ | mGlu5 K$_i$ (nM) | mGlu1 K$_i$ (nM) |
|---|---|---|---|---|
| 12. | 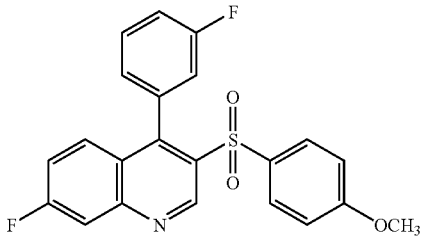 | 412.2 | ** | * |
| 13. | 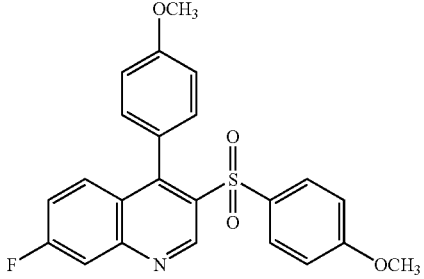 | 424.2 | *** | * |
| 14. | 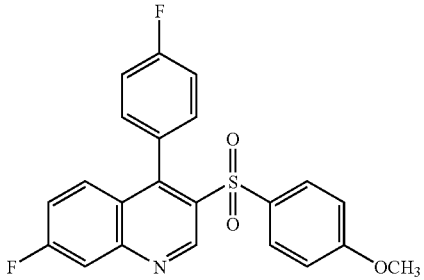 | 412.2 | ** | * |
| 15. | 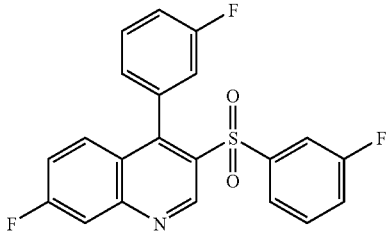 | 400.2 | * |  |
| 16. | 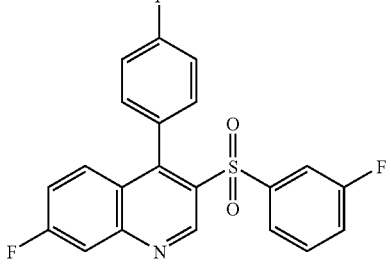 | 400.2 | *** | * |

TABLE 1-continued

| Comp. No. | Structure | (M + H)+ or M+ | mGlu5 $K_i$ (nM) | mGlu1 $K_i$ (nM) |
|---|---|---|---|---|
| 17. | 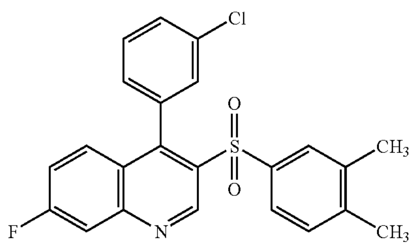 | 426.2 | *** | * |
| 18. | 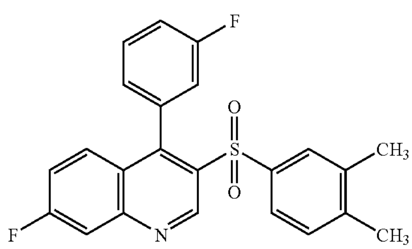 | 410.2 | *** | * |
| 19. | 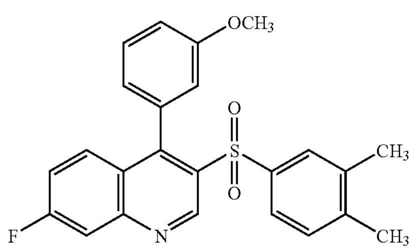 | 422.3 | *** | * |
| 20. | 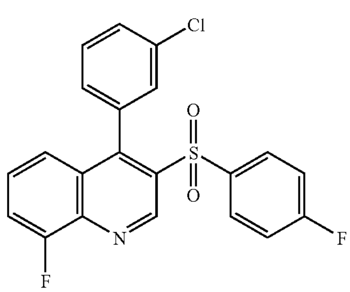 | 416.2 | * | * |
| 21. | 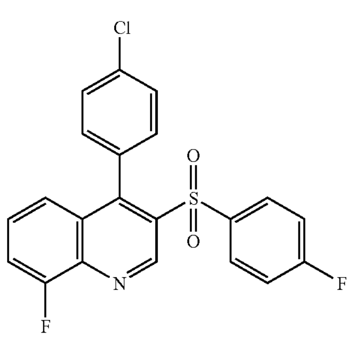 | 416.2 | * |  |

TABLE 1-continued

| Comp. No. | Structure | (M + H)+ or M+ | mGlu5 $K_i$ (nM) | mGlu1 $K_i$ (nM) |
|---|---|---|---|---|
| 22. | 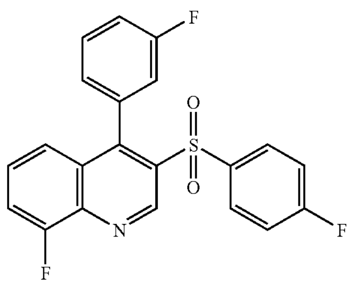 | 400.2 | * |  |
| 23. | 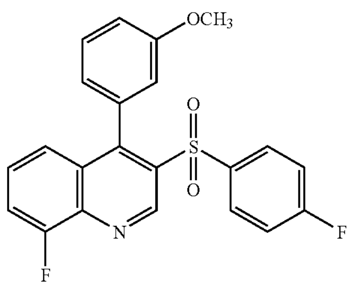 | 412.2 | *** | * |
| 24. | 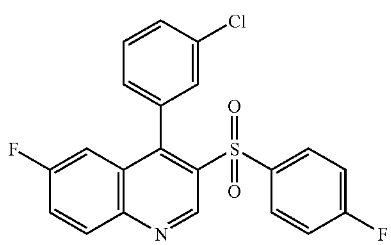 | 416.2 | * | * |
| 25. | 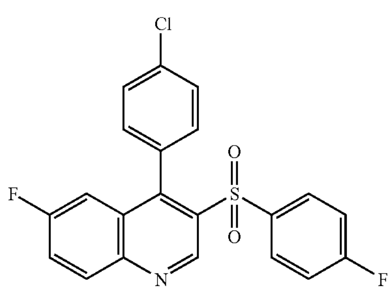 | 416.2 | ** | * |
| 26. | 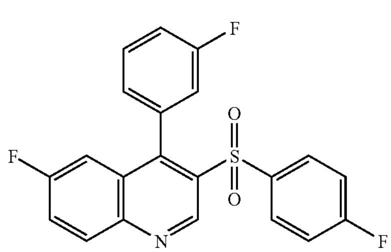 | 400.2 | ** | * |

TABLE 1-continued

| Comp. No. | Structure | $(M + H)^+$ or $M^+$ | mGlu5 $K_i$ (nM) | mGlu1 $K_i$ (nM) |
|---|---|---|---|---|
| 27. | 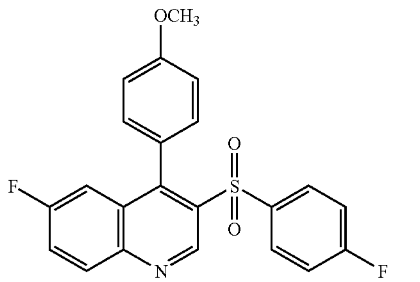 | 412.2 | * | * |
| 28. | 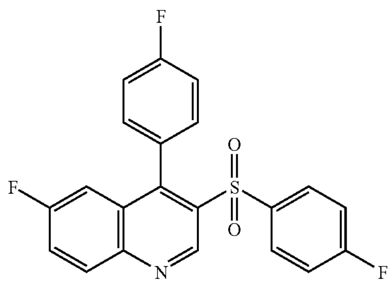 | 400.2 | * | * |
| 29. | 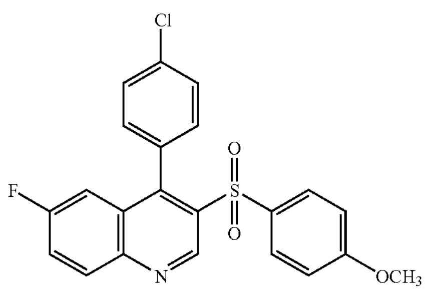 | 428.2 | *** | * |
| 30. | 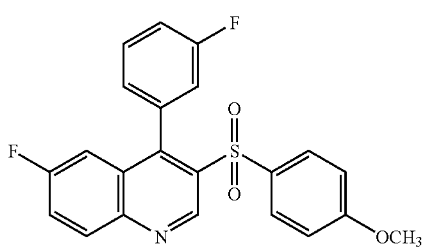 | 412.2 | ** | * |
| 31. | 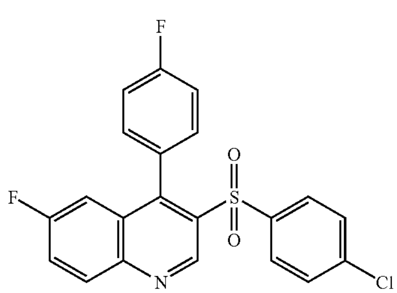 | 416.2 | * | * |

TABLE 1-continued

| Comp. No. | Structure | (M + H)+ or M+ | mGlu5 $K_i$ (nM) | mGlu1 $K_i$ (nM) |
|---|---|---|---|---|
| 32. | 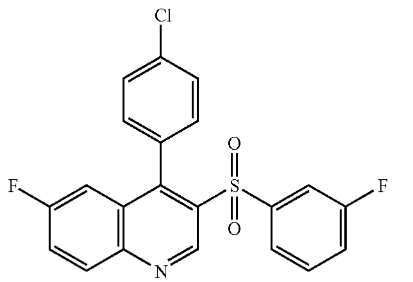 | 416.2 | * | * |
| 33. | 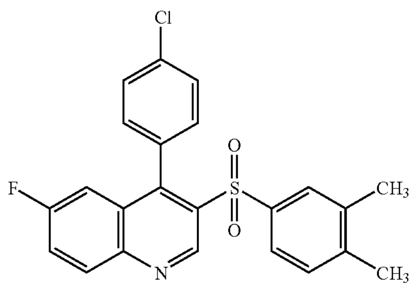 | 426.2 | *** | * |
| 34. | 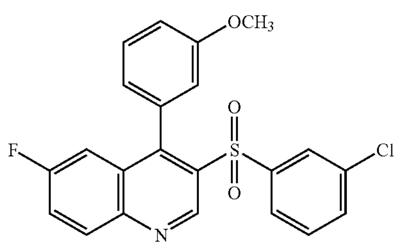 | 428.2 | * | * |
| 35. | 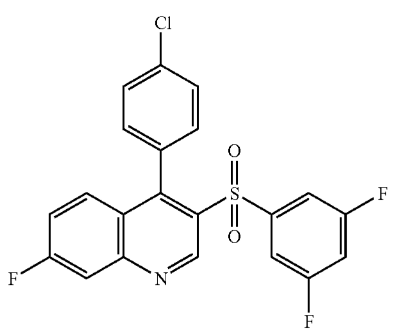 | 434.2 | *** | * |
| 36. | 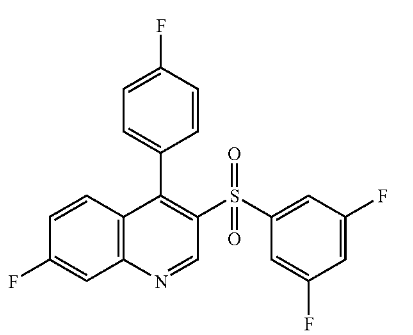 | 418.2 | *** | * |

TABLE 1-continued

| Comp. No. | Structure | (M + H)+ or M+ | mGlu5 K$_i$ (nM) | mGlu1 K$_i$ (nM) |
|---|---|---|---|---|
| 37. | 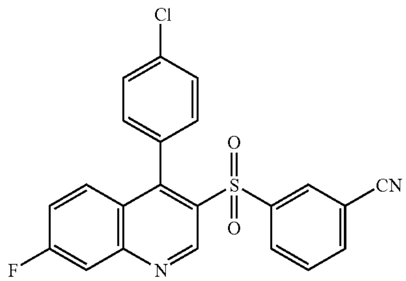 | 423.2 | * |  |
| 38. | 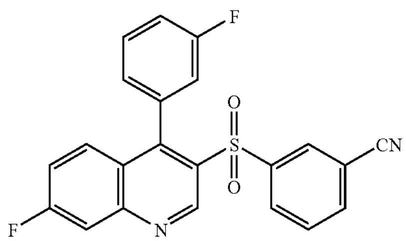 | 407.2 | * |  |
| 39. | 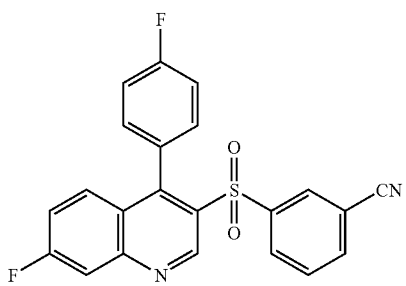 | 407.2 | * |  |
| 40. | 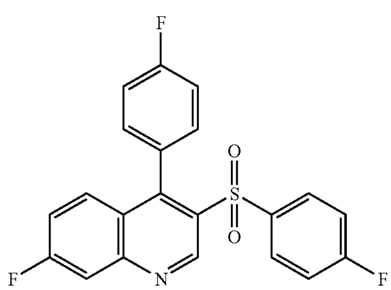 | 400.2 | *** | * |
| 41. | 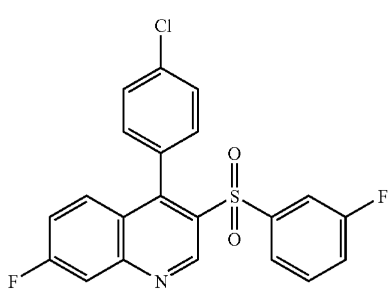 | 416.2 | *** | * |

TABLE 1-continued

| Comp. No. | Structure | (M + H)+ or M+ | mGlu5 $K_i$ (nM) | mGlu1 $K_i$ (nM) |
|---|---|---|---|---|
| 42. | 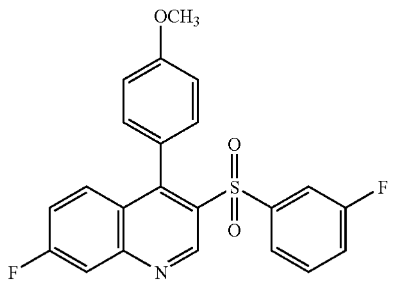 | 412.2 | ** | * |
| 43. | 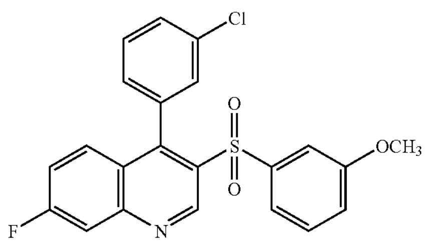 | 428.2 | *** | * |
| 44. | 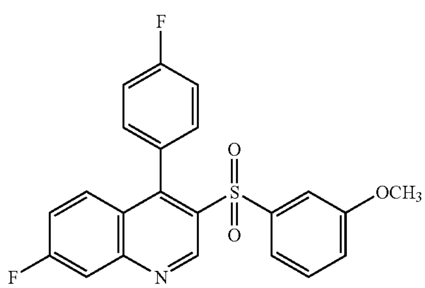 | 412.2 | *** | * |
| 45. | 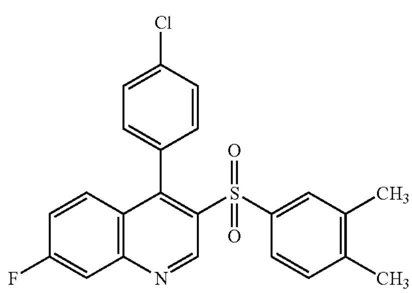 | 426.2 | *** | * |
| 46. | 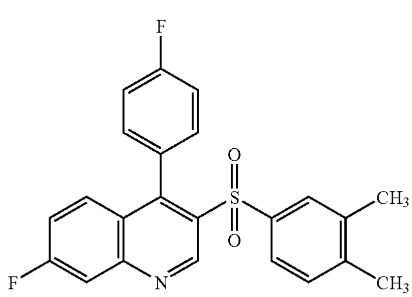 | 410.2 | *** | * |

TABLE 1-continued

| Comp. No. | Structure | (M + H)+ or M+ | mGlu5 K$_i$ (nM) | mGlu1 K$_i$ (nM) |
|---|---|---|---|---|
| 47. | 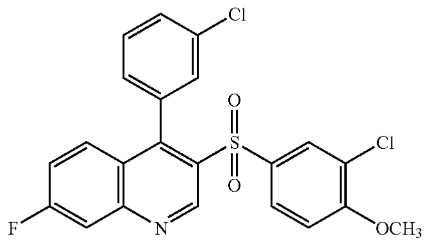 | 463.2 | * |  |
| 48. | 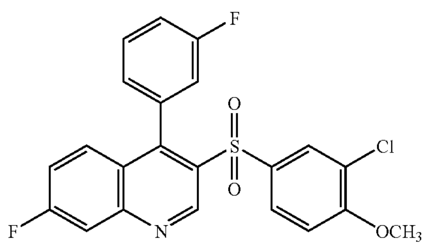 | 446.2 | *** | * |
| 49. | 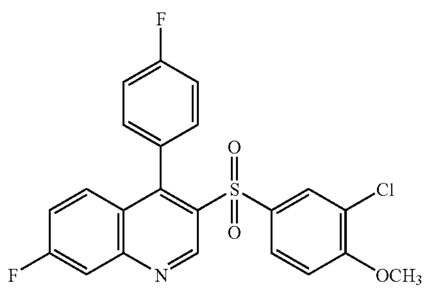 | 446.2 | *** | * |
| 50. | 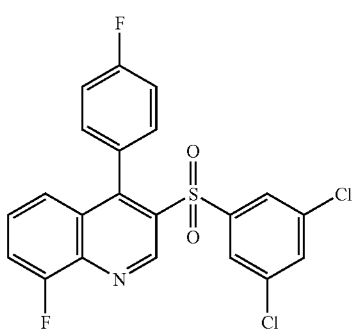 | 451.2 | * | * |
| 51. | 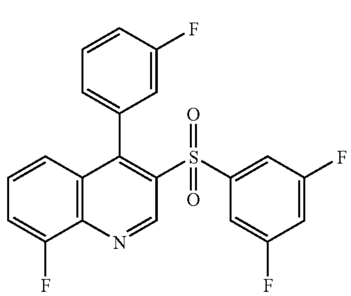 | 418.2 | *** | * |

TABLE 1-continued

| Comp. No. | Structure | (M + H)+ or M+ | mGlu5 K$_i$ (nM) | mGlu1 K$_i$ (nM) |
|---|---|---|---|---|
| 52. | (4-methoxyphenyl at 4-position; 4-fluorophenylsulfonyl at 3-position; 8-fluoroquinoline) | 412.2 | *** | * |
| 53. | (3-chlorophenyl at 4-position; 4-methoxyphenylsulfonyl at 3-position; 8-fluoroquinoline) | 428.2 | *** | * |
| 54. | (4-chlorophenyl at 4-position; 4-methoxyphenylsulfonyl at 3-position; 8-fluoroquinoline) | 428.2 | *** | *** |
| 55. | (3-fluorophenyl at 4-position; 4-methoxyphenylsulfonyl at 3-position; 8-fluoroquinoline) | 412.2 | *** | * |
| 56. | (4-methoxyphenyl at 4-position; 4-methoxyphenylsulfonyl at 3-position; 8-fluoroquinoline) | 424.2 | *** | * |

TABLE 1-continued

| Comp. No. | Structure | $(M + H)^+$ or $M^+$ | mGlu5 $K_i$ (nM) | mGlu1 $K_i$ (nM) |
|---|---|---|---|---|
| 57. | 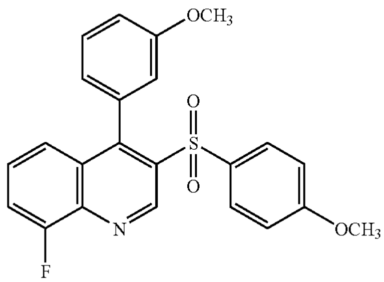 | 424.2 | *** | * |
| 58. | 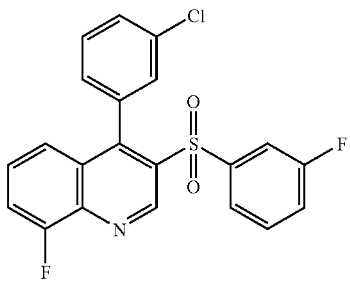 | 416.2 | * |  |
| 59. | 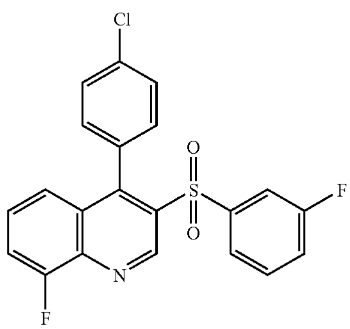 | 416.2 | * |  |
| 60. | 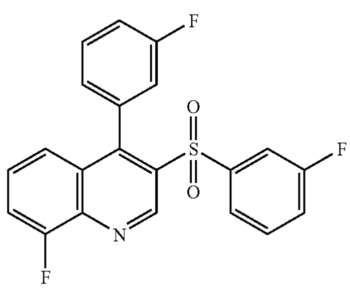 | 400.2 | * |  |
| 61. | 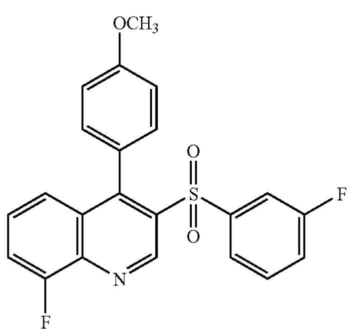 | 412.2 | *** | * |

TABLE 1-continued

| Comp. No. | Structure | (M + H)+ or M+ | mGlu5 K$_i$ (nM) | mGlu1 K$_i$ (nM) |
|---|---|---|---|---|
| 62. | 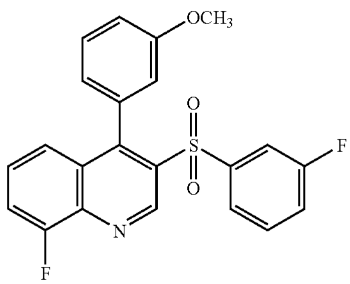 | 412.2 | *** | * |
| 63. | 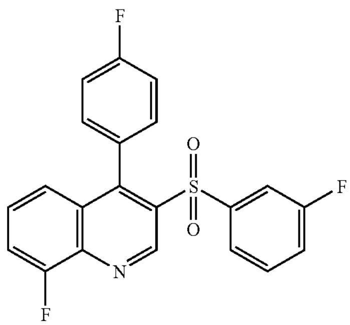 | 400.2 | * |  |
| 64. | 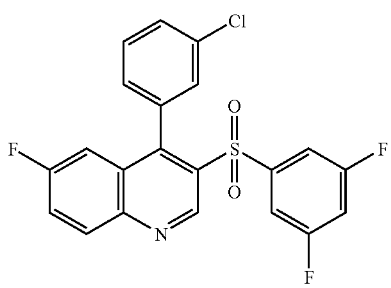 | 434.2 | * | * |
| 65. | 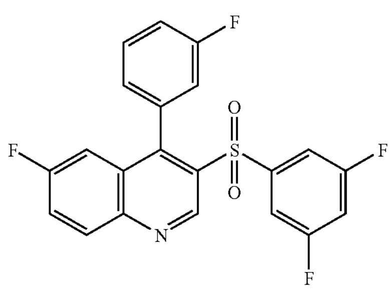 | 418.2 |  |  |
| 66. | 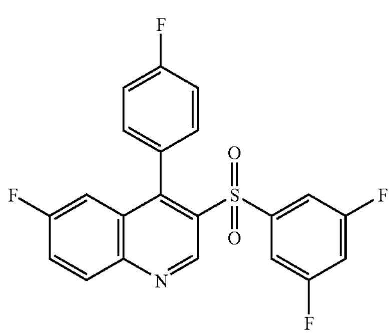 | 418.2 | ** | * |

TABLE 1-continued

| Comp. No. | Structure | (M + H)+ or M+ | mGlu5 $K_i$ (nM) | mGlu1 $K_i$ (nM) |
|---|---|---|---|---|
| 67. | 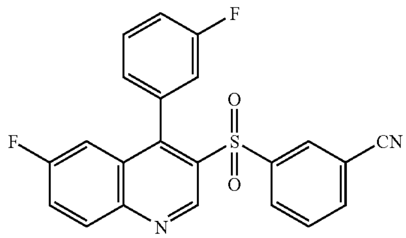 | 407.2 | * |  |
| 68. | 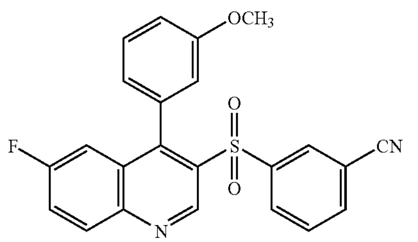 | 419.3 | *** | * |
| 69. | 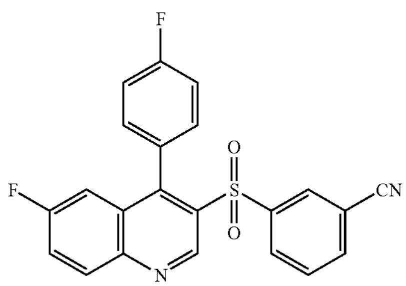 | 407.2 | * |  |
| 70. | 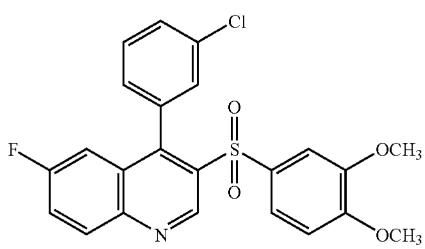 | 458.3 | * | * |
| 71. | 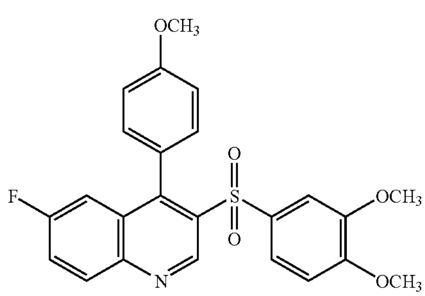 | 454.3 | * | * |
| 72. | 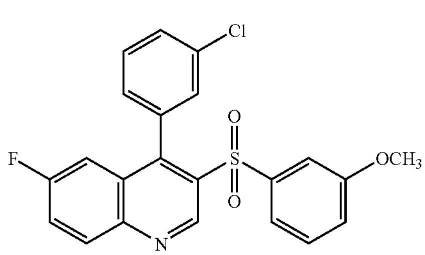 | 428.2 | *** | * |

TABLE 1-continued

| Comp. No. | Structure | (M + H)+ or M+ | mGlu5 $K_i$ (nM) | mGlu1 $K_i$ (nM) |
|---|---|---|---|---|
| 73. | 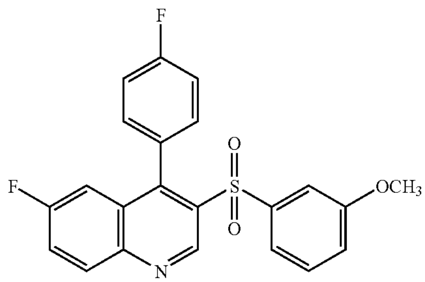 | 412.2 | *** | * |
| 74. | 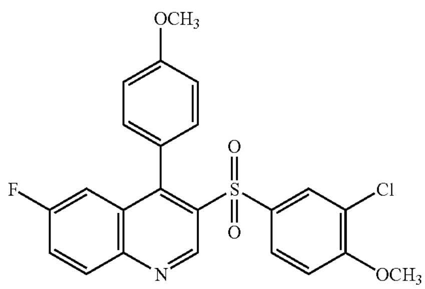 | 458.3 | *** | * |
| 75. | 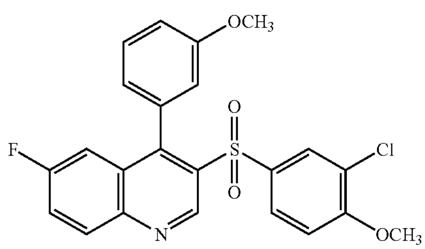 | 458.3 | *** | * |
| 76. | 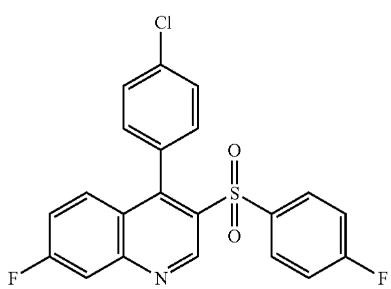 | 416.2 | *** | * |
| 77. | 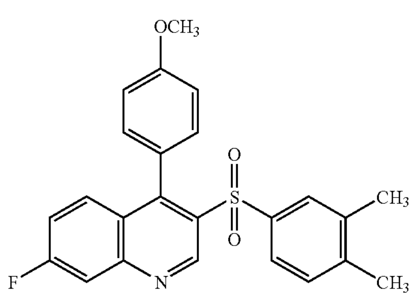 | 422.3 | *** | * |

TABLE 1-continued

| Comp. No. | Structure | $(M + H)^+$ or $M^+$ | mGlu5 $K_i$ (nM) | mGlu1 $K_i$ (nM) |
| --- | --- | --- | --- | --- |
| 78. | 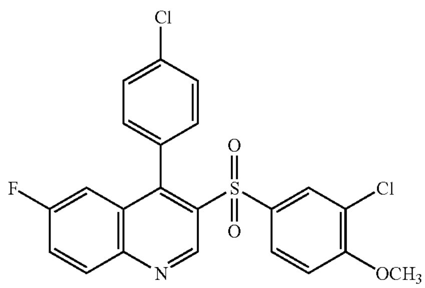 | 463.2 | *** | * |
| 79. | 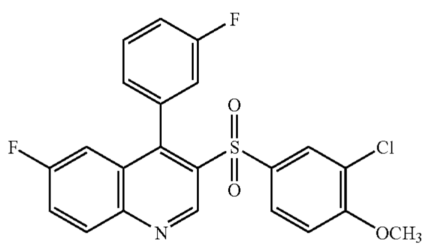 | 446.2 | *** | * |
| 80. | 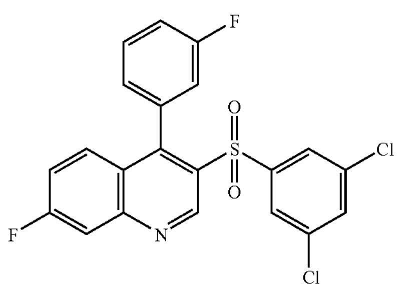 | 451.2 | * |  |
| 81. | 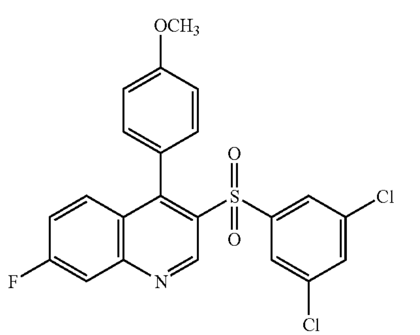 | 463.2 | *** | * |
| 82. | 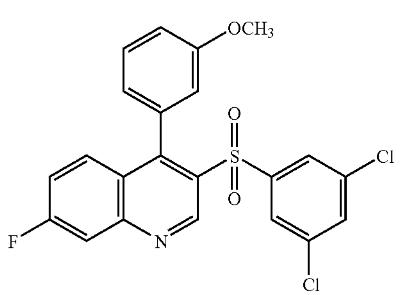 | 463.2 | *** | * |

TABLE 1-continued

| Comp. No. | Structure | (M + H)+ or M+ | mGlu5 K$_i$ (nM) | mGlu1 K$_i$ (nM) |
|---|---|---|---|---|
| 83. | 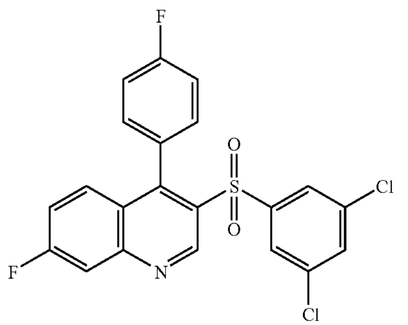 | 451.2 | | ** |
| 84. | 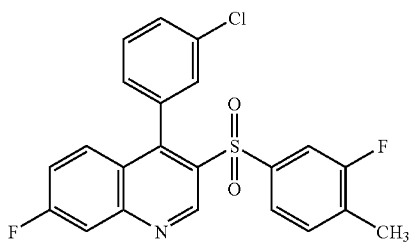 | 430.2 | *** | * |
| 85. | 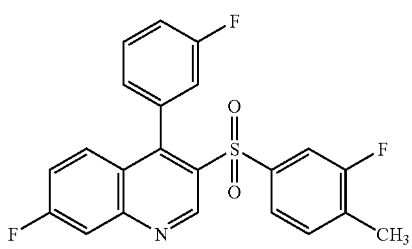 | 414.2 | *** | * |
| 86. | 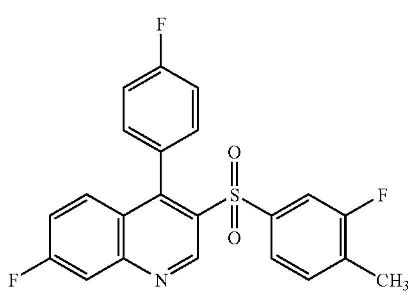 | 414.2 | *** | * |
| 87. | 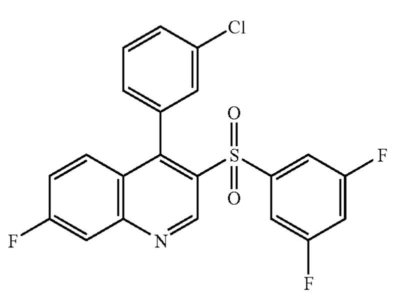 | 434.2 | ** | * |

TABLE 1-continued
| Comp. No. | Structure | (M + H)+ or M+ | mGlu5 K$_i$ (nM) | mGlu1 K$_i$ (nM) |
|---|---|---|---|---|
| 88. | 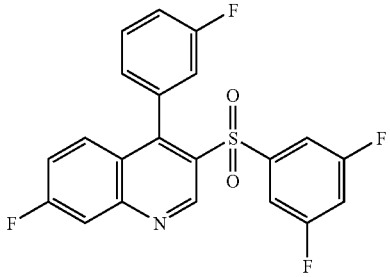 | 418.2 | * |  |
| 89. | 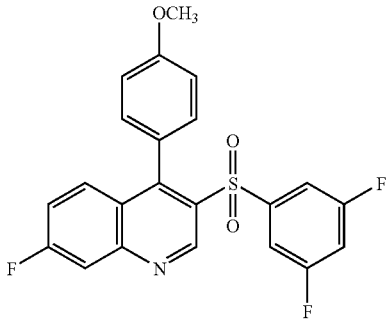 | 430.3 | *** | * |
| 90. | 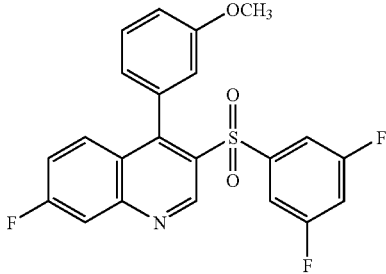 | 430.3 | *** | * |
| 91. | 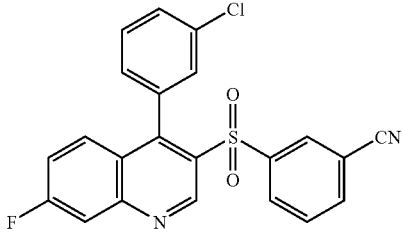 | 423.2 | * | * |
| 92. | 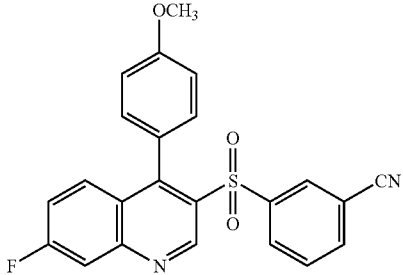 | 419.3 | * |  |

TABLE 1-continued

| Comp. No. | Structure | (M + H)+ or M+ | mGlu5 $K_i$ (nM) | mGlu1 $K_i$ (nM) |
|---|---|---|---|---|
| 93. | 4-(3-methoxyphenyl)-3-(3-cyanophenylsulfonyl)-7-fluoroquinoline | 419.3 | *** | * |
| 94. | 4-(3-fluorophenyl)-3-(3-chloro-4-methylphenylsulfonyl)-7-fluoroquinoline | 430.2 | *** | * |
| 95. | 4-(3-fluorophenyl)-3-(3-methoxyphenylsulfonyl)-7-fluoroquinoline | 412.2 | ** | * |
| 96. | 4-(3-methoxyphenyl)-3-(3-chloro-4-methoxyphenylsulfonyl)-7-fluoroquinoline | 458.3 | ** | * |
| 97. | 4-(3-chlorophenyl)-3-(3,4-difluorophenylsulfonyl)-7-fluoroquinoline | 434.2 | ** | ** |
| 98. | 4-(3-fluorophenyl)-3-(3,4-difluorophenylsulfonyl)-7-fluoroquinoline | 418.2 | *** | ** |

TABLE 1-continued

| Comp. No. | Structure | (M + H)+ or M+ | mGlu5 K$_i$ (nM) | mGlu1 K$_i$ (nM) |
|---|---|---|---|---|
| 99. | 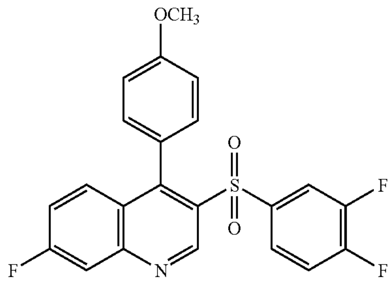 | 430.3 | *** | * |
| 100. | 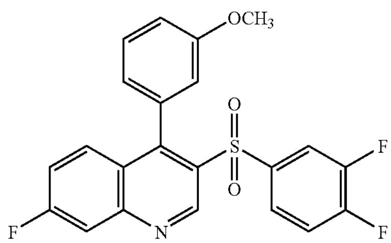 | 430.3 | *** | * |
| 101. | 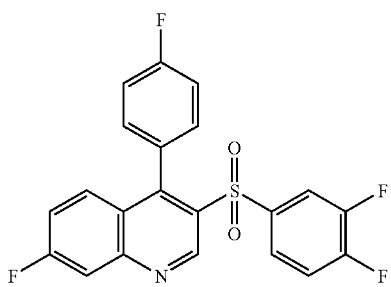 | 418.2 | * |  |
| 102. | 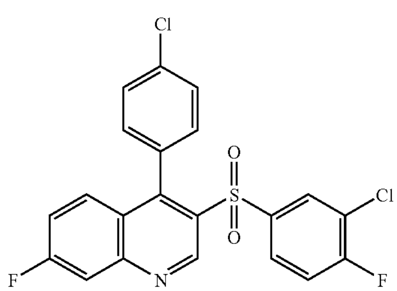 | 451.2 | * |  |
| 103. | 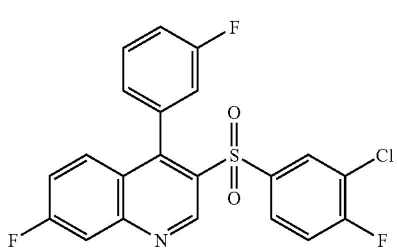 | 434.2 | * | * |

TABLE 1-continued

| Comp. No. | Structure | (M + H)+ or M+ | mGlu5 K$_i$ (nM) | mGlu1 K$_i$ (nM) |
|---|---|---|---|---|
| 104. | 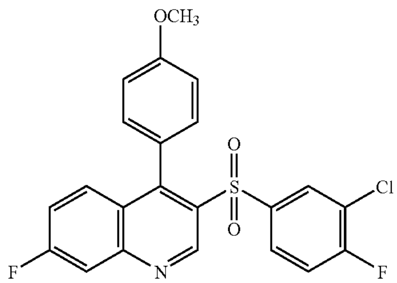 | 446.2 | * |  |
| 105. | 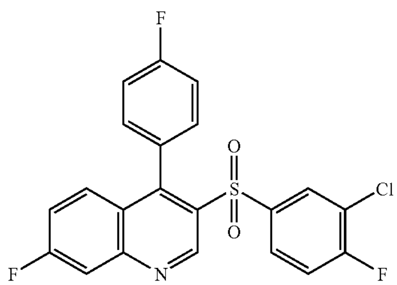 | 434.2 | * | * |
| 106. | 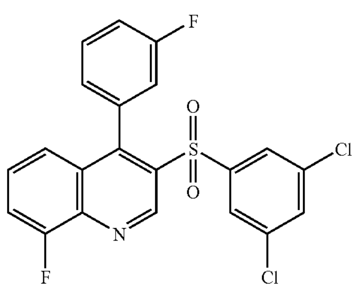 | 451.2 | *** | * |
| 107. | 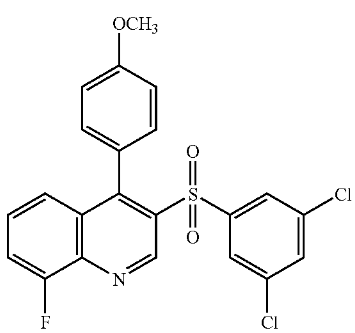 | 463.2 | *** | * |
| 108. | 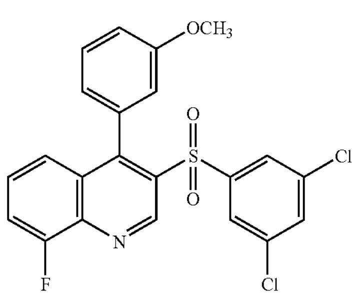 | 463.2 | *** | * |

TABLE 1-continued

| Comp. No. | Structure | $(M + H)^+$ or $M^+$ | mGlu5 $K_i$ (nM) | mGlu1 $K_i$ (nM) |
|---|---|---|---|---|
| 109. | 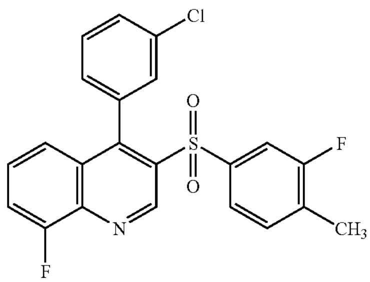 | 430.2 | *** | * |
| 110. | 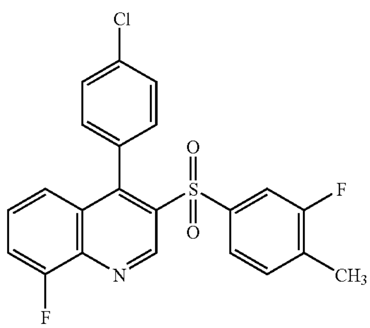 | 430.2 | *** | * |
| 111. | 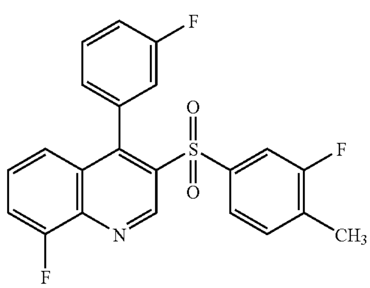 | 414.2 | *** | * |
| 112. | 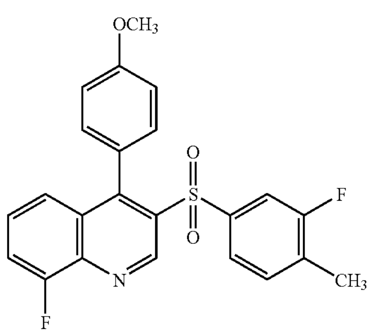 | 426.3 | *** | * |
| 113. | 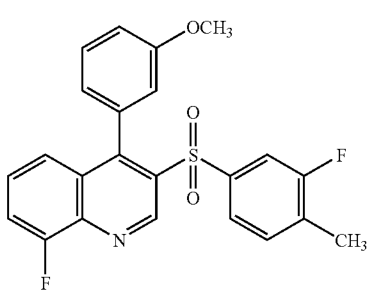 | 426.3 | *** | * |

TABLE 1-continued

| Comp. No. | Structure | (M + H)+ or M+ | mGlu5 $K_i$ (nM) | mGlu1 $K_i$ (nM) |
|---|---|---|---|---|
| 114. | 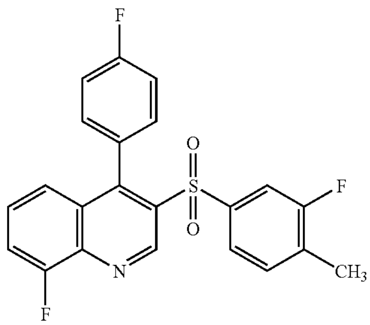 | 414.2 | *** | * |
| 115. | 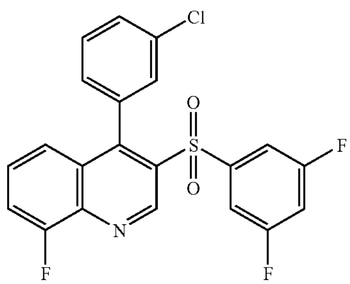 | 434.2 | * |  |
| 116. | 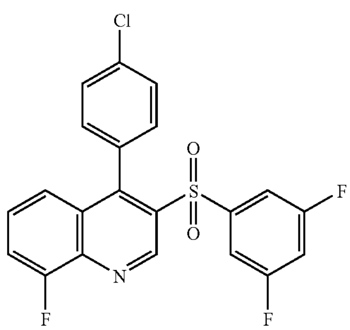 | 434.2 | * |  |
| 117. | 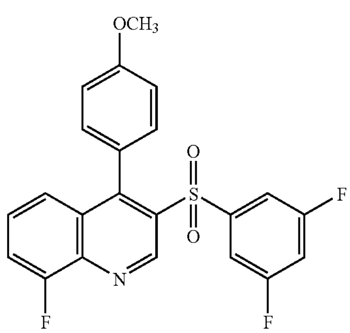 | 430.3 | *** | * |
| 118. | 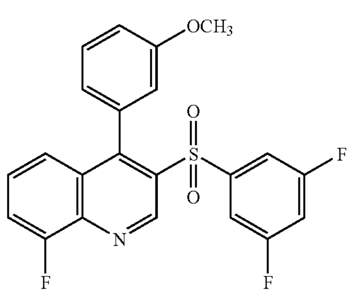 | 430.3 | *** | * |

TABLE 1-continued

| Comp. No. | Structure | (M + H)+ or M+ | mGlu5 $K_i$ (nM) | mGlu1 $K_i$ (nM) |
|---|---|---|---|---|
| 119. | 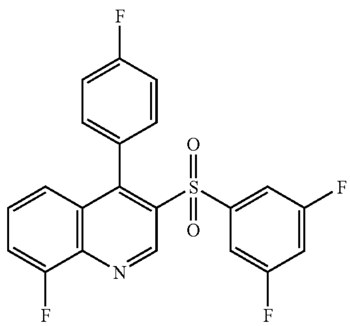 | 418.2 | * | * |
| 120. | 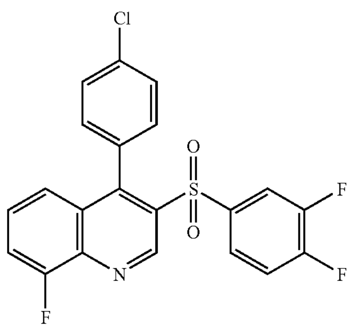 | 434.2 | * |  |
| 121. | 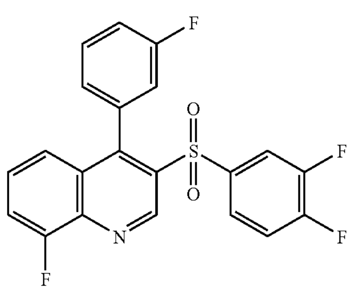 | 418.2 | * | * |
| 122. | 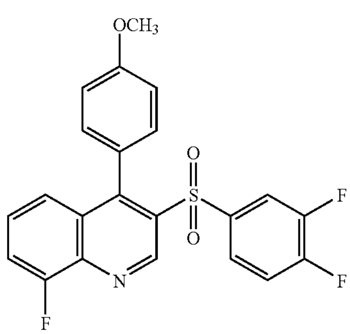 | 430.3 | *** | * |

TABLE 1-continued

| Comp. No. | Structure | (M + H)+ or M+ | mGlu5 K_i (nM) | mGlu1 K_i (nM) |
|---|---|---|---|---|
| 123. | 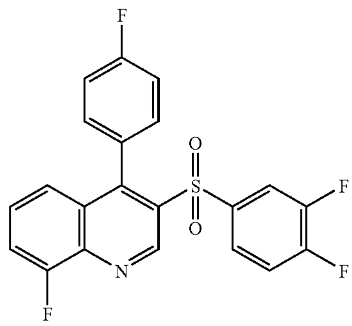 | 418.2 | * | * |
| 124. | 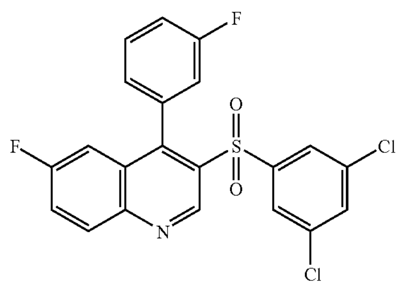 | 451.2 | * |  |
| 125. | 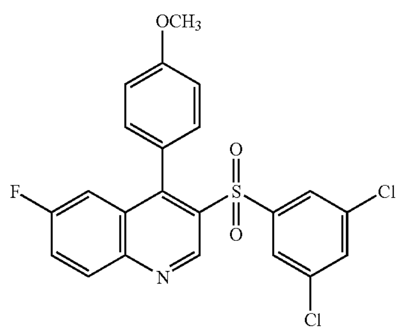 | 463.2 | *** | * |
| 126. | 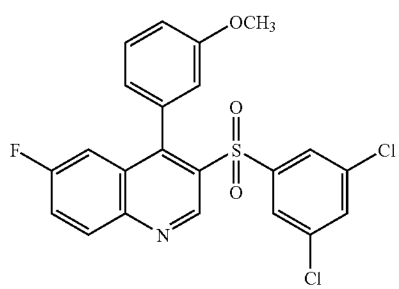 | 463.2 | *** | * |
| 127. | 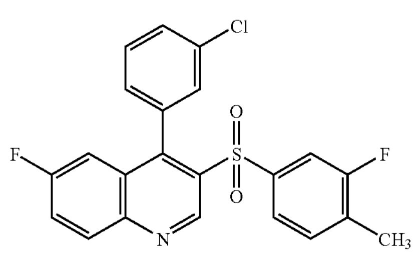 | 430.2 | *** | * |

TABLE 1-continued

| Comp. No. | Structure | (M + H)+ or M+ | mGlu5 K$_i$ (nM) | mGlu1 K$_i$ (nM) |
|---|---|---|---|---|
| 128. | 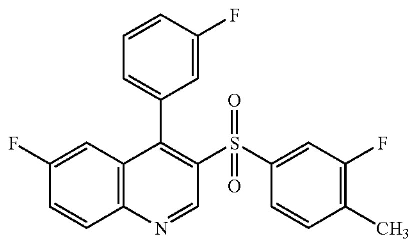 | 414.2 | *** | * |
| 129. | 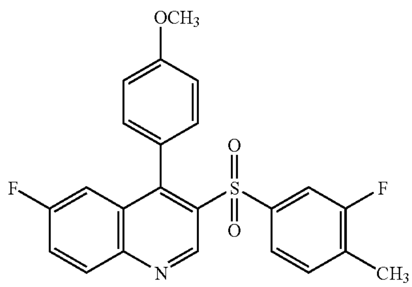 | 426.3 | *** | * |
| 130. | 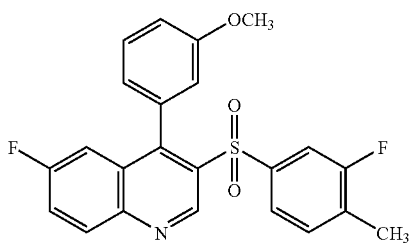 | 426.3 | *** | * |
| 131. | 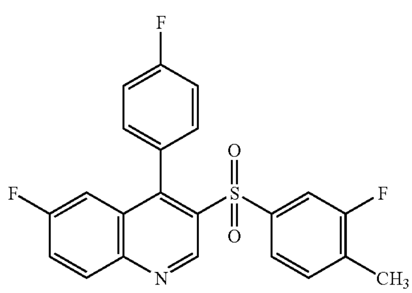 | 414.2 | *** | * |
| 132. | 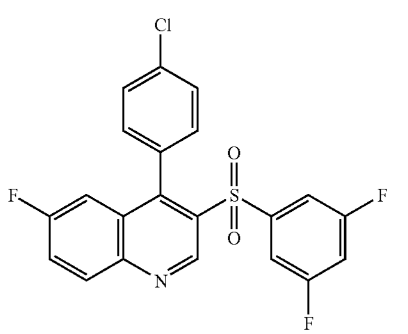 | 434.2 | ** | * |

TABLE 1-continued

| Comp. No. | Structure | (M + H)+ or M+ | mGlu5 K$_i$ (nM) | mGlu1 K$_i$ (nM) |
|---|---|---|---|---|
| 133. | 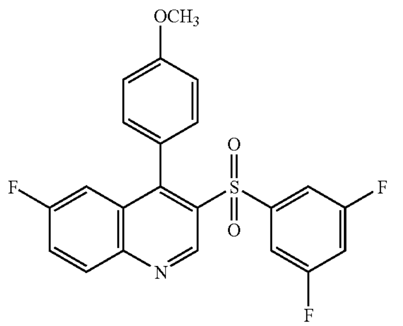 | 430.3 | ** | * |
| 134. | 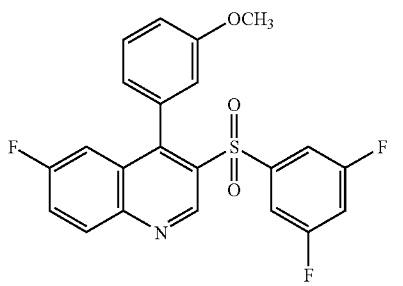 | 430.3 | ** | * |
| 135. | 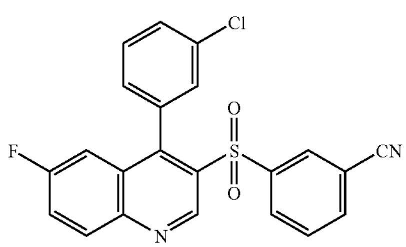 | 423.2 | * |  |
| 136. | 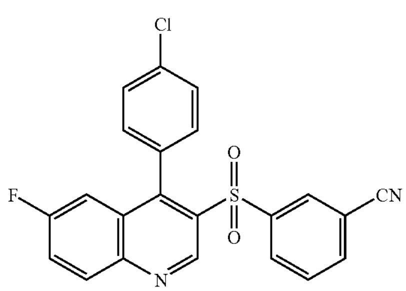 | 423.2 | * |  |
| 137. | 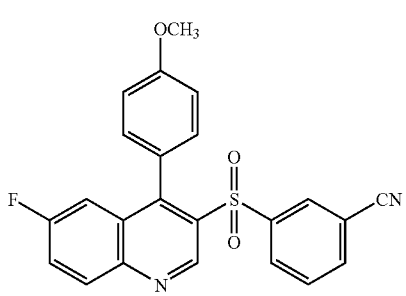 | 419.3 | *** | * |

TABLE 1-continued

| Comp. No. | Structure | (M + H)+ or M+ | mGlu5 K$_i$ (nM) | mGlu1 K$_i$ (nM) |
|---|---|---|---|---|
| 138. | 4-(3-chlorophenyl)-3-[(3-chloro-4-methylphenyl)sulfonyl]-6-fluoroquinoline | 447.2 | *** | * |
| 139. | 4-(4-chlorophenyl)-3-[(3-chloro-4-methylphenyl)sulfonyl]-6-fluoroquinoline | 447.2 | *** | * |
| 140. | 3-[(3-chloro-4-methylphenyl)sulfonyl]-6-fluoro-4-(3-fluorophenyl)quinoline | 430.2 | *** | * |
| 141. | 3-[(3-chloro-4-methylphenyl)sulfonyl]-6-fluoro-4-(3-methoxyphenyl)quinoline | 442.2 | *** | * |
| 142. | 3-[(3-chloro-4-methylphenyl)sulfonyl]-6-fluoro-4-(4-fluorophenyl)quinoline | 430.2 | *** | * |

TABLE 1-continued

| Comp. No. | Structure | (M + H)+ or M+ | mGlu5 $K_i$ (nM) | mGlu1 $K_i$ (nM) |
|---|---|---|---|---|
| 143. | 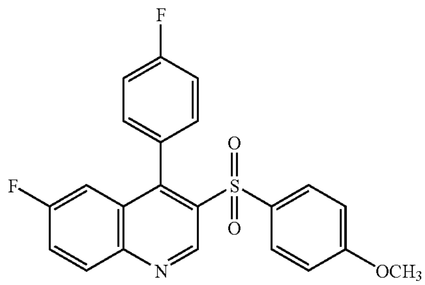 | 412.2 | ** | * |
| 144. | 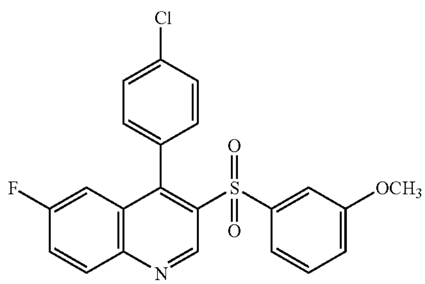 | 428.2 | *** | * |
| 145. | 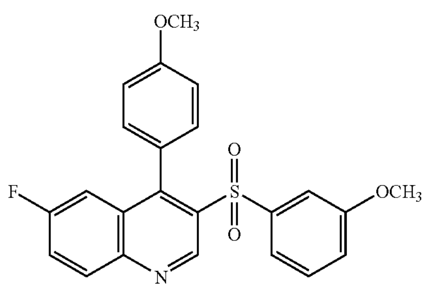 | 424.2 | *** | * |
| 146. | 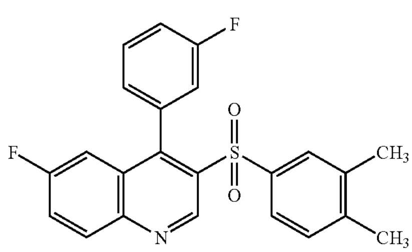 | 410.2 | *** | * |
| 147. | 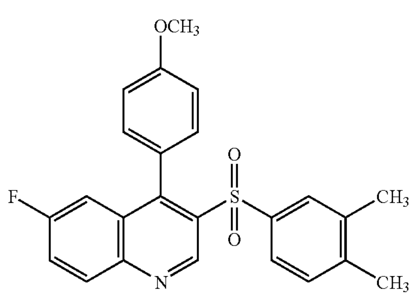 | 422.3 | *** | * |

TABLE 1-continued

| Comp. No. | Structure | (M + H)+ or M+ | mGlu5 K_i (nM) | mGlu1 K_i (nM) |
|---|---|---|---|---|
| 148. | 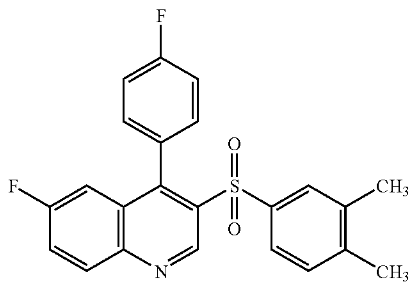 | 410.2 | *** | * |
| 149. | 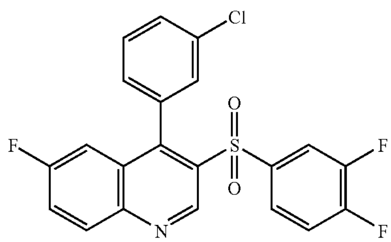 | 434.2 |  |  |
| 150. | 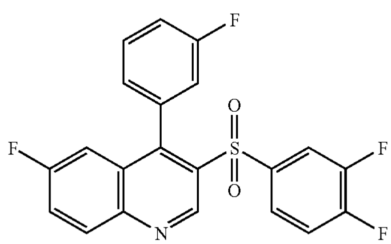 | 418.2 | * |  |
| 151. | 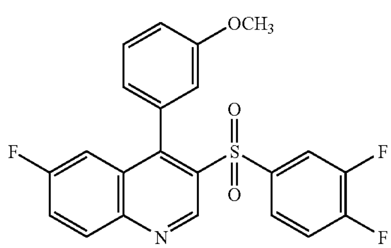 | 430.3 | ** | * |
| 152. | 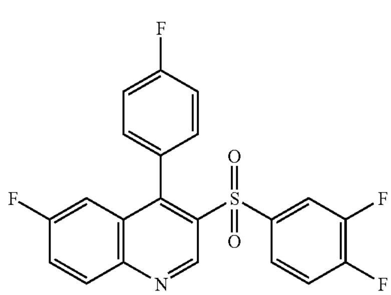 | 418.2 | * |  |

TABLE 1-continued

| Comp. No. | Structure | (M + H)+ or M+ | mGlu5 K$_i$ (nM) | mGlu1 K$_i$ (nM) |
|---|---|---|---|---|
| 153. | 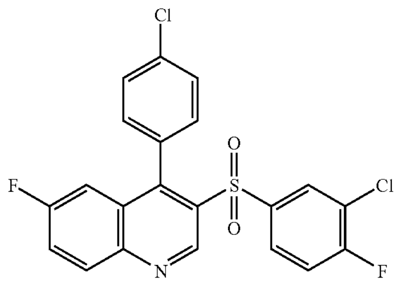 | 451.2 | * |  |
| 154. | 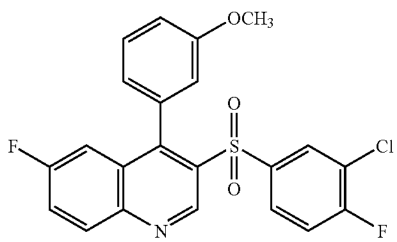 | 446.2 | *** | * |
| 155. | 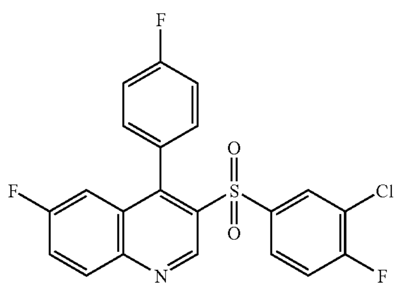 | 434.2 | * |  |
| 156. | 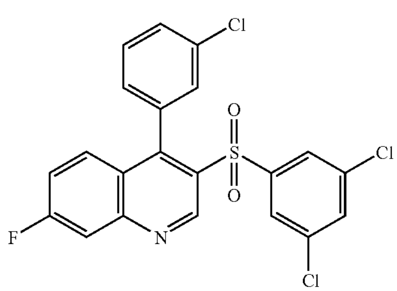 | 468.1 | * |  |
| 157. | 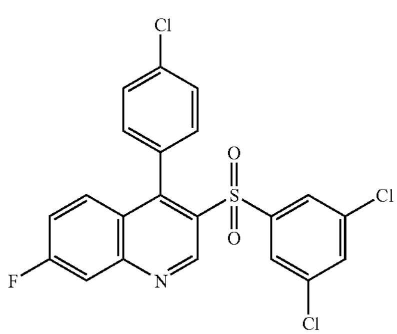 | 468.1 | * |  |

TABLE 1-continued

| Comp. No. | Structure | (M + H)+ or M+ | mGlu5 K$_i$ (nM) | mGlu1 K$_i$ (nM) |
|---|---|---|---|---|
| 158. | 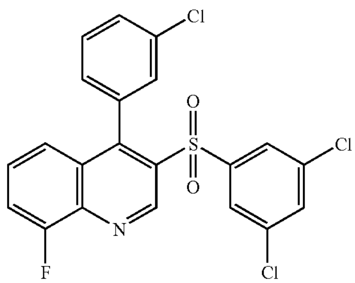 | 468.1 | * |  |
| 159. | 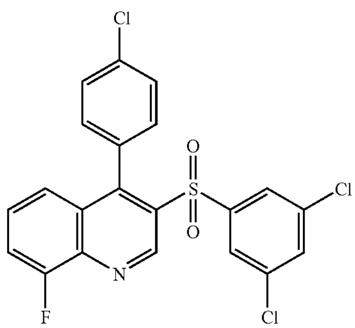 | 468.1 | * |  |
| 160. | 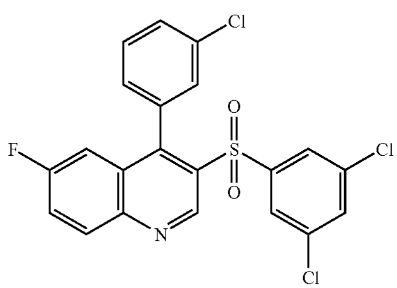 | 468.1 | *** | * |
| 161. | 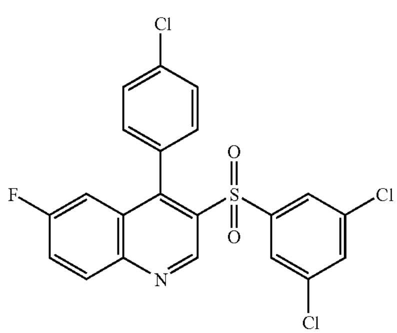 | 468.1 | *** | * |
| 162. | 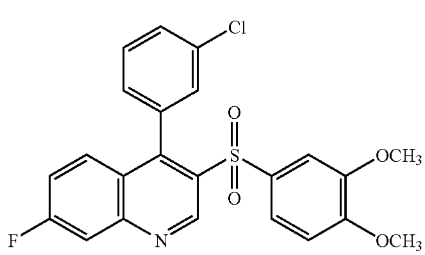 | 458.3 | * | * |

TABLE 1-continued

| Comp. No. | Structure | (M + H)+ or M+ | mGlu5 K$_i$ (nM) | mGlu1 K$_i$ (nM) |
|---|---|---|---|---|
| 163. | 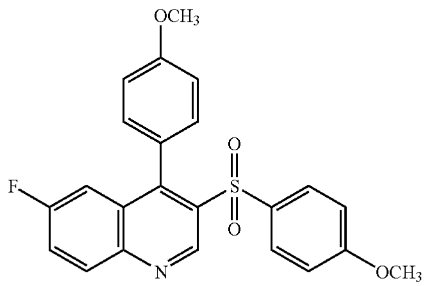 | 424.2 | *** | * |
| 164. | 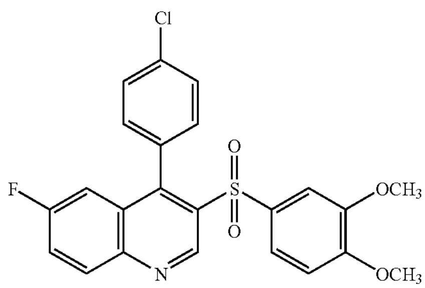 | 458.3 | * | * |
| 165. | 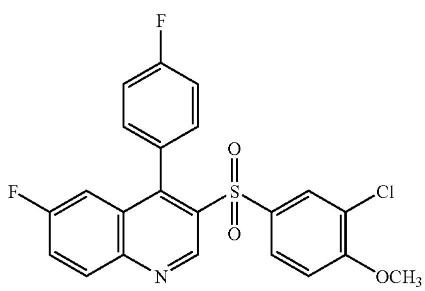 | 446.2 | * | * |
| 166. | 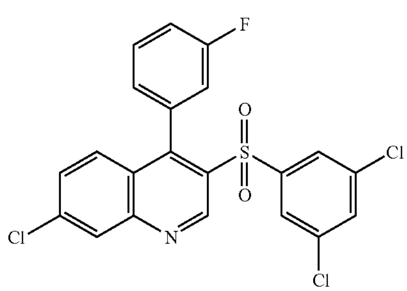 | 468.1 | *** | * |
| 167. | 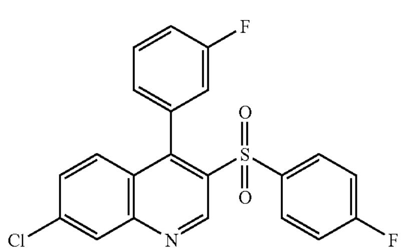 | 416.2 | *** | * |

TABLE 1-continued

| Comp. No. | Structure | (M + H)+ or M+ | mGlu5 $K_i$ (nM) | mGlu1 $K_i$ (nM) |
|---|---|---|---|---|
| 168. | 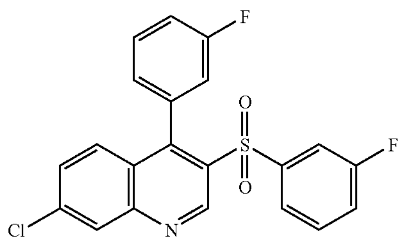 | 416.2 | *** | * |
| 169. | 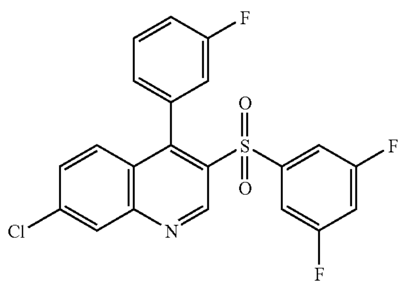 | 434.2 | *** | * |
| 170. | 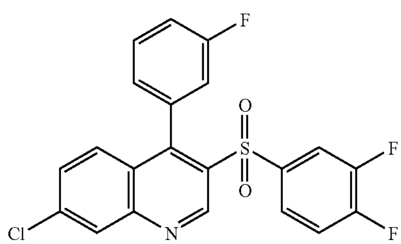 | 434.2 | *** | * |
| 171. | 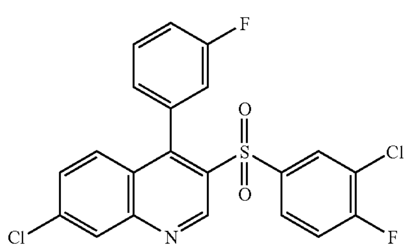 | 451.2 | *** | * |
| 172. | 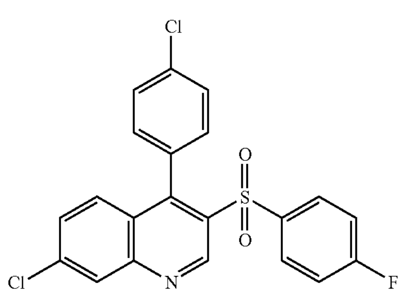 | 433.2 | *** | * |

TABLE 1-continued

| Comp. No. | Structure | (M + H)+ or M+ | mGlu5 K$_i$ (nM) | mGlu1 K$_i$ (nM) |
|---|---|---|---|---|
| 173. | 7-chloro-4-(4-chlorophenyl)-3-[(3-fluorophenyl)sulfonyl]quinoline | 433.2 | *** | * |
| 174. | 7-chloro-4-(4-chlorophenyl)-3-[(3,5-difluorophenyl)sulfonyl]quinoline | 451.2 | *** | * |
| 175. | 7-chloro-4-(4-chlorophenyl)-3-[(3,4-difluorophenyl)sulfonyl]quinoline | 451.2 | *** | * |
| 176. | 7-chloro-4-(4-chlorophenyl)-3-[(3-chloro-4-fluorophenyl)sulfonyl]quinoline | 468.1 | *** | * |
| 177. | 7-chloro-4-(4-chlorophenyl)-3-[(3-cyanophenyl)sulfonyl]quinoline | 440.2 | *** | * |

TABLE 1-continued

| Comp. No. | Structure | (M + H)+ or M+ | mGlu5 $K_i$ (nM) | mGlu1 $K_i$ (nM) |
|---|---|---|---|---|
| 178. | 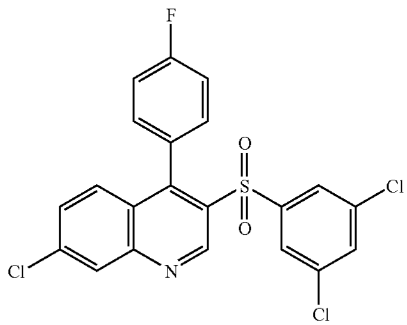 | 468.1 | *** | * |
| 179. | 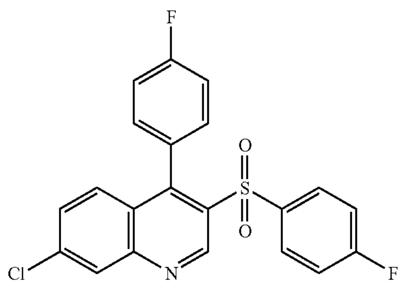 | 416.2 | *** | * |
| 180. | 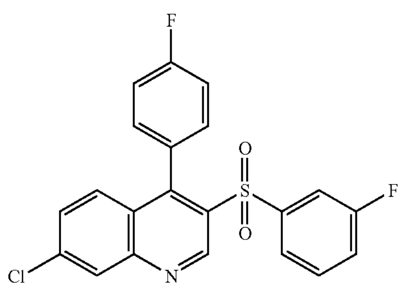 | 416.2 | *** | * |
| 181. | 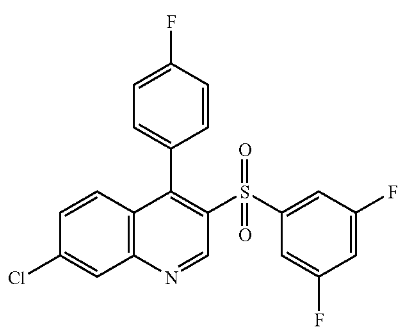 | 434.2 | *** | * |
| 182. | 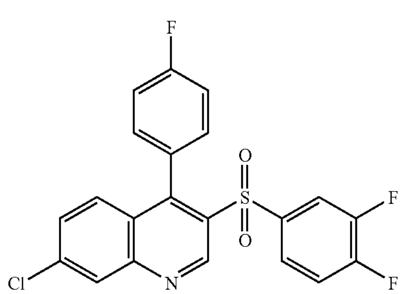 | 434.2 | *** | * |

TABLE 1-continued
| Comp. No. | Structure | (M + H)+ or M+ | mGlu5 $K_i$ (nM) | mGlu1 $K_i$ (nM) |
|---|---|---|---|---|
| 183. | 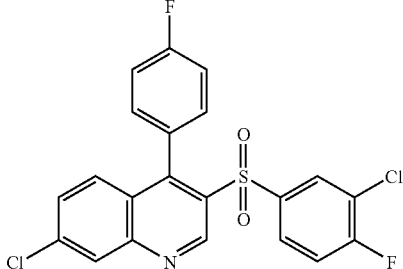 | 451.2 | *** | * |
| 184. | 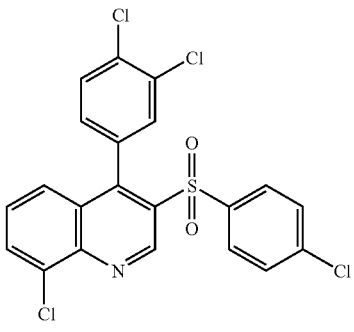 | 484.1 | * | * |
| 185. | 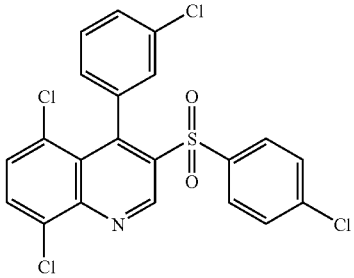 | 484.1 | * | * |
| 186. | 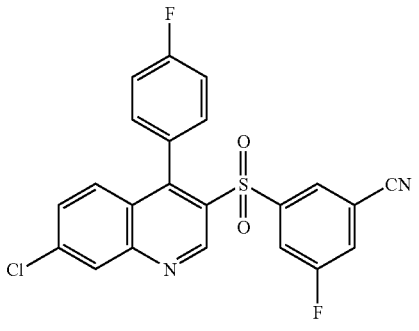 | 441.2 | *** | * |
| 187. | 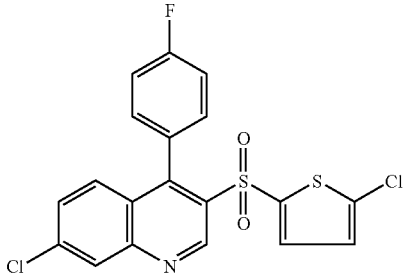 | 439.2 | ** | * |

TABLE 1-continued

| Comp. No. | Structure | (M + H)+ or M+ | mGlu5 K$_i$ (nM) | mGlu1 K$_i$ (nM) |
|---|---|---|---|---|
| 188. | 4-(3-fluorophenyl)-6-chloro-7-fluoro-3-(3-fluoro-4-chlorophenylsulfonyl)quinoline | 469.2 | ** | * |
| 189. | 4-(4-chlorophenyl)-6-chloro-7-fluoro-3-(3-fluoro-4-chlorophenylsulfonyl)quinoline | 485.2 | *** | * |
| 190. | 4-(4-fluorophenyl)-6-chloro-7-fluoro-3-(3-fluoro-4-chlorophenylsulfonyl)quinoline | 469.2 | *** | * |
| 191. | 4-(4-chlorophenyl)-7-cyano-3-(3-cyanophenylsulfonyl)quinoline | 430.2 | ** | * |
| 192. | 4-(4-fluorophenyl)-7-cyano-3-(3,4-difluorophenylsulfonyl)quinoline | 425.2 | * | * |

TABLE 1-continued

| Comp. No. | Structure | (M + H)+ or M+ | mGlu5 K$_i$ (nM) | mGlu1 K$_i$ (nM) |
|---|---|---|---|---|
| 193. | 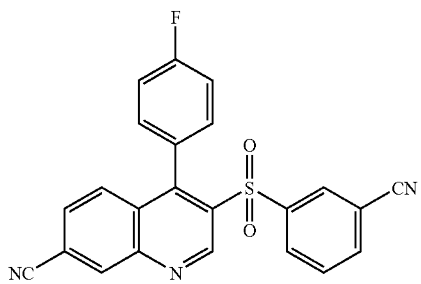 | 414.3 | ** | * |
| 194. | 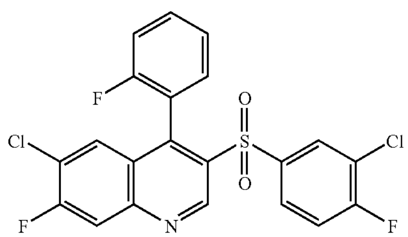 | 469.2 | * | * |
| 195. | 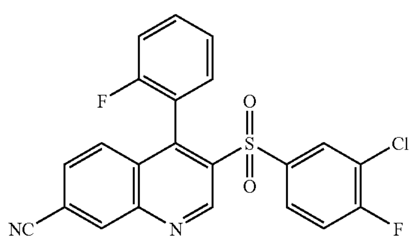 | 441.2 | *** | * |
| 196. | 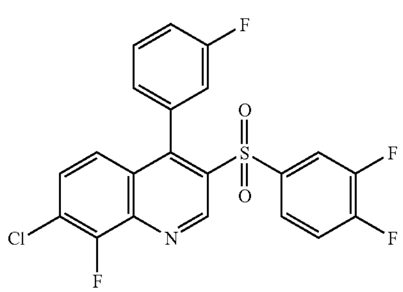 | 452.2 | *** | * |
| 197. | 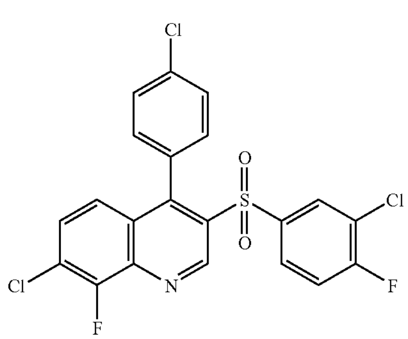 | 485.2 | *** | * |

TABLE 1-continued

| Comp. No. | Structure | (M + H)+ or M+ | mGlu5 K_i (nM) | mGlu1 K_i (nM) |
|---|---|---|---|---|
| 198. | 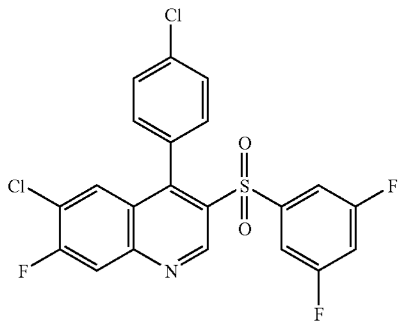 | 469.2 | * | * |
| 199. | 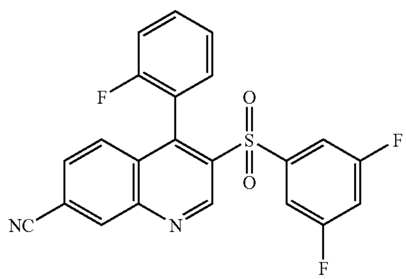 | 425.3 | ** | * |
| 200. | 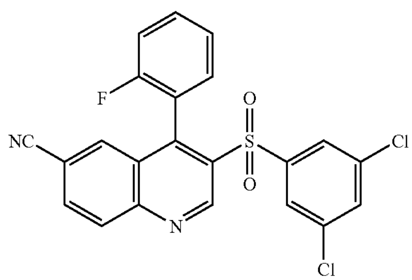 | 458.2 | * | * |
| 201. | 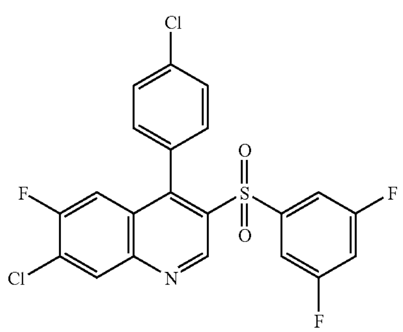 | 469.2 | * | * |
| 202. | 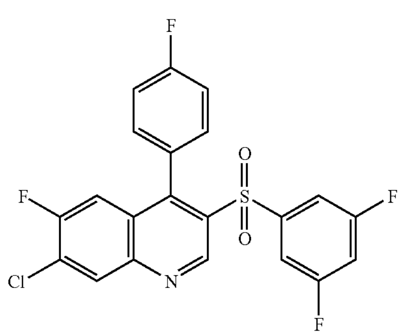 | 452.2 | ** | * |

TABLE 1-continued

| Comp. No. | Structure | (M + H)+ or M+ | mGlu5 $K_i$ (nM) | mGlu1 $K_i$ (nM) |
|---|---|---|---|---|
| 203. | 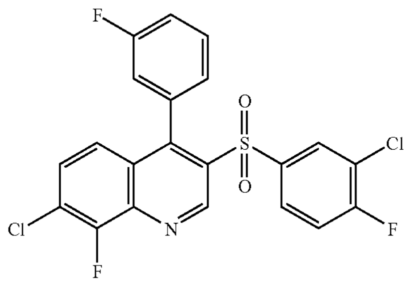 | 469.2 | *** | * |
| 204. | 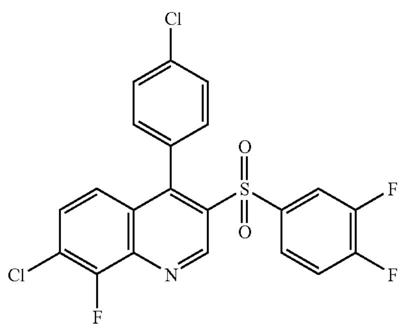 | 469.2 | *** | * |
| 205. | 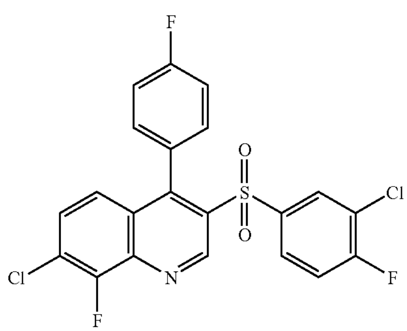 | 469.2 | *** | * |
| 206. | 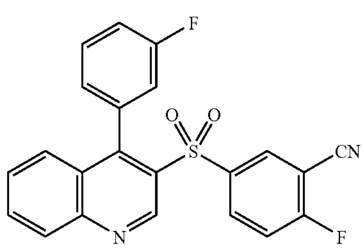 | 407.3 | *** | * |
| 207. | 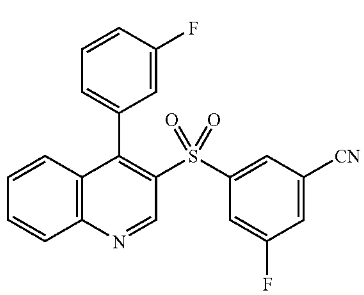 | 407.3 | *** | * |

TABLE 1-continued

| Comp. No. | Structure | (M + H)+ or M+ | mGlu5 $K_i$ (nM) | mGlu1 $K_i$ (nM) |
|---|---|---|---|---|
| 208. | 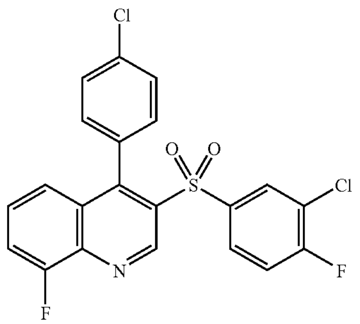 | 451.1 | * |  |
| 209. | 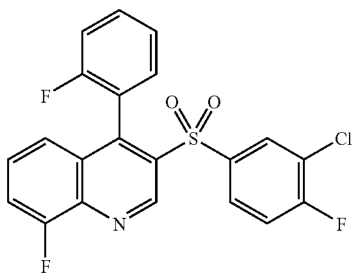 | 434.2 | * |  |
| 210. | 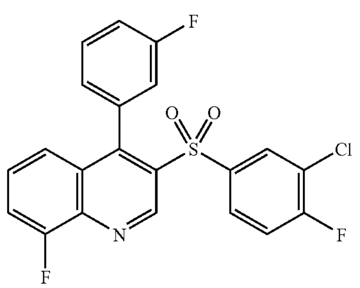 | 434.2 | * |  |
| 211. | 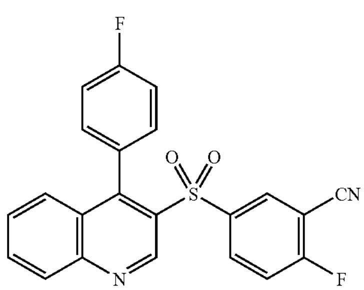 | 407.3 | *** | * |
| 212. | 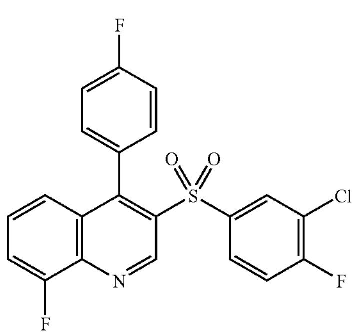 | 434.2 | * |  |

TABLE 1-continued

| Comp. No. | Structure | (M + H)+ or M+ | mGlu5 $K_i$ (nM) | mGlu1 $K_i$ (nM) |
|---|---|---|---|---|
| 213. | 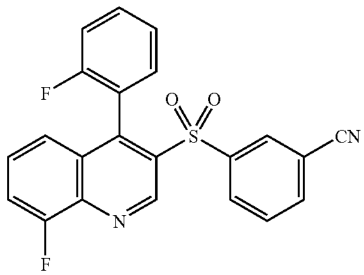 | 407.2 | *** | * |
| 214. | 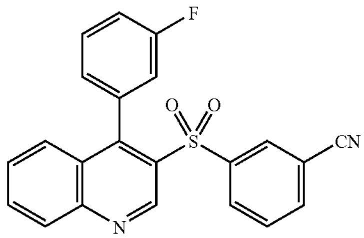 | 389.1 | *** | * |
| 215. | 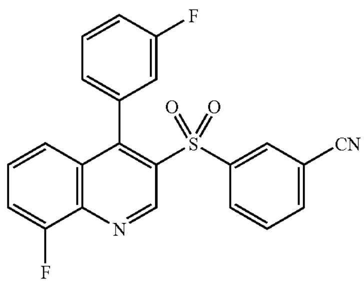 | 407.2 | *** | * |
| 216. | 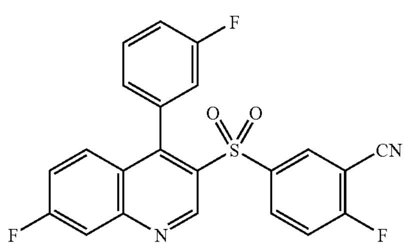 | 425.1 | *** | * |
| 217. | 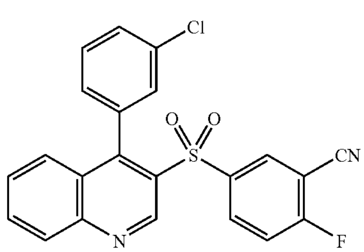 | 423.2 | *** | * |

TABLE 1-continued
| Comp. No. | Structure | (M + H)+ or M+ | mGlu5 $K_i$ (nM) | mGlu1 $K_i$ (nM) |
|---|---|---|---|---|
| 218. | 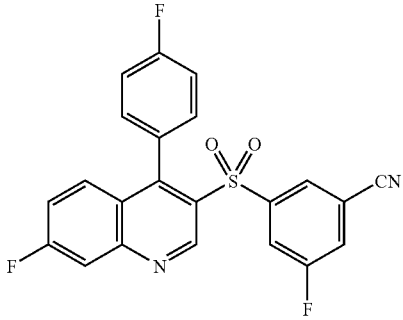 | 425.1 | *** | * |
| 219. | 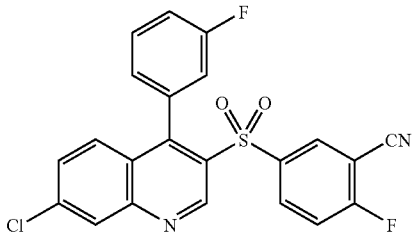 | 441.0 | * | * |
| 220. | 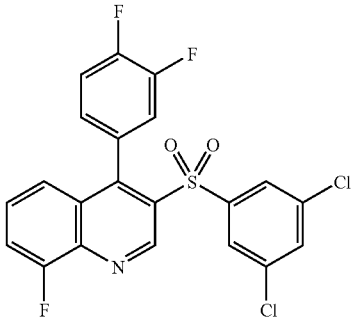 | 469.4 | *** | * |
| 221. | 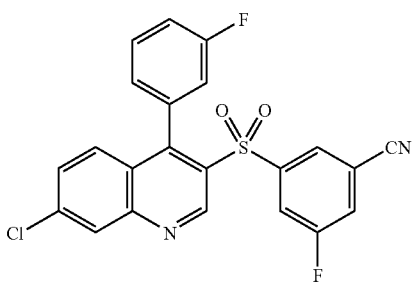 | 441.0 | * |  |
| 222. | 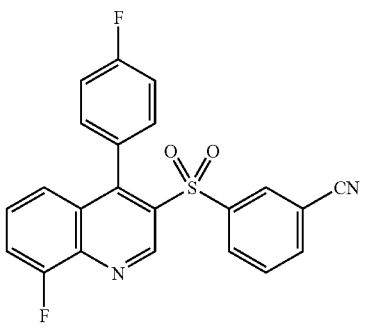 | 407.2 | *** | * |

TABLE 1-continued

| Comp. No. | Structure | (M + H)+ or M+ | mGlu5 $K_i$ (nM) | mGlu1 $K_i$ (nM) |
|---|---|---|---|---|
| 223. | 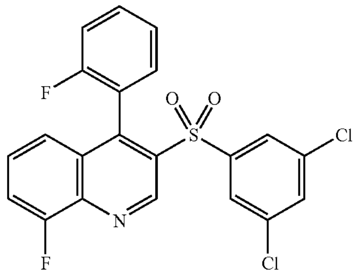 | 451.2 | *** | * |
| 224. | 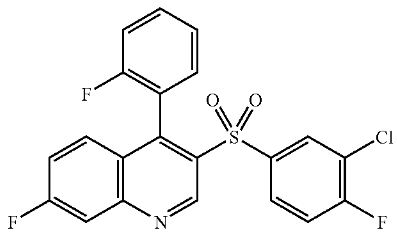 | 434.2 | * |  |
| 225. | 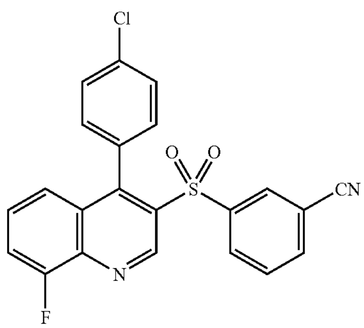 | 423.2 | *** | * |
| 226. | 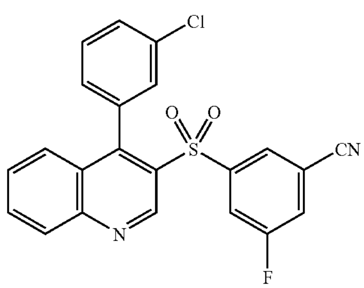 | 423.2 | *** | * |
| 227. | 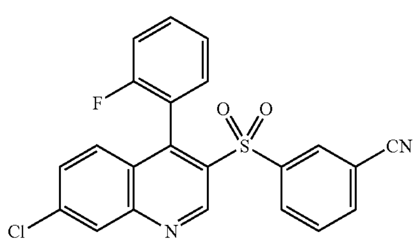 | 423.2 | * | * |

TABLE 1-continued

| Comp. No. | Structure | (M + H)+ or M+ | mGlu5 $K_i$ (nM) | mGlu1 $K_i$ (nM) |
|---|---|---|---|---|
| 228. | 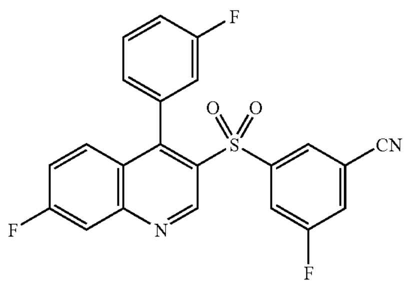 | 425.1 | *** | * |
| 229. | 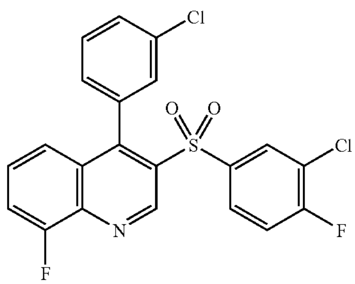 | 451.2 | * |  |
| 230. | 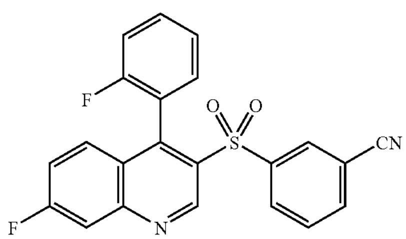 | 407.2 | *** | * |
| 231. | 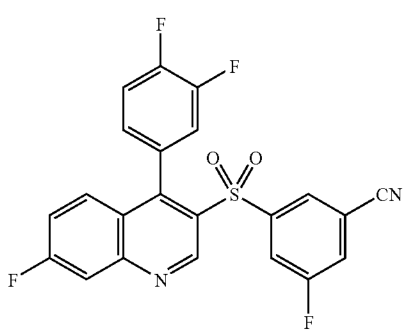 | 443.4 | *** | * |
| 232. | 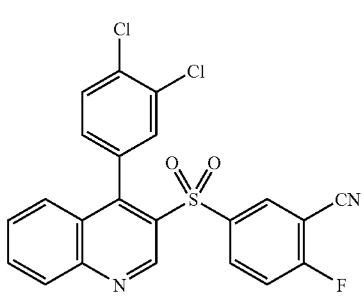 | 457.3 | *** | * |

TABLE 1-continued

| Comp. No. | Structure | (M + H)+ or M+ | mGlu5 K$_i$ (nM) | mGlu1 K$_i$ (nM) |
|---|---|---|---|---|
| 233. | 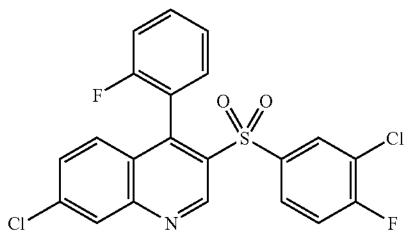 | 451.2 | * | * |
| 234. | 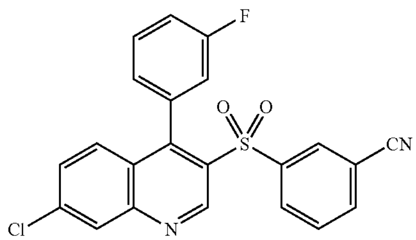 | 423.3 | * | * |
| 235. | 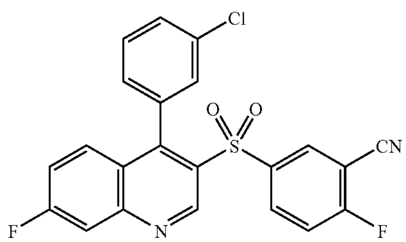 | 441.2 | *** | * |
| 236. | 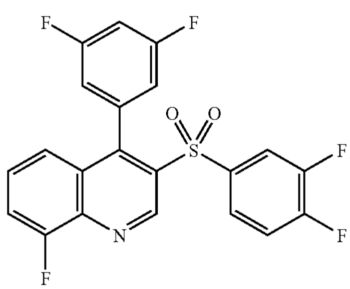 | 436.2 | * |  |
| 237. | 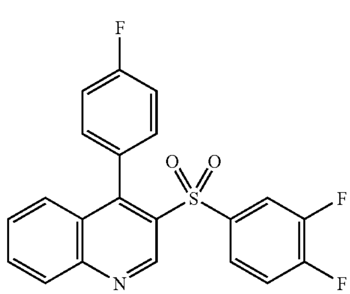 | 400.3 | *** | * |

TABLE 1-continued

| Comp. No. | Structure | (M + H)+ or M+ | mGlu5 K$_i$ (nM) | mGlu1 K$_i$ (nM) |
|---|---|---|---|---|
| 238. | 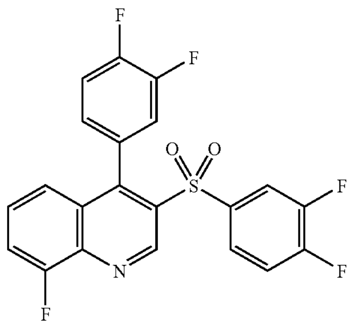 | 436.2 | *** | * |
| 239. | 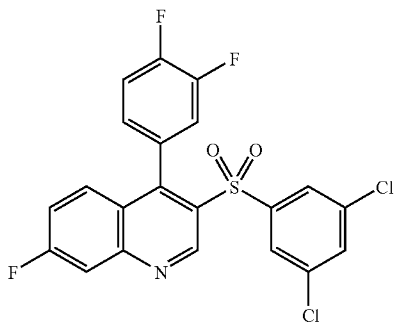 | 468.8 | *** | * |
| 240. | 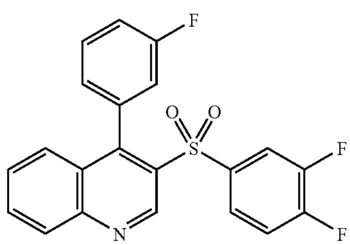 | 400.1 | *** | * |
| 241. | 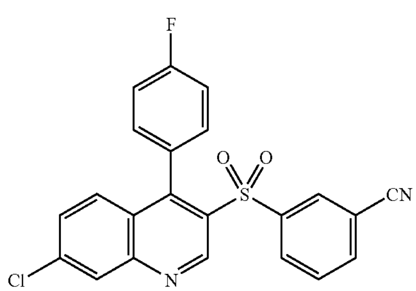 | 423.3 | * |  |
| 242. | 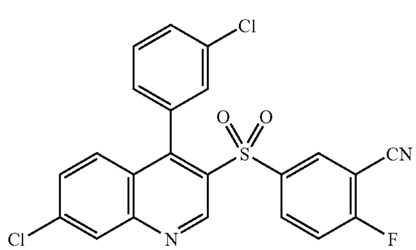 | 458.0 | * | * |

TABLE 1-continued

| Comp. No. | Structure | $(M+H)^+$ or $M^+$ | mGlu5 $K_i$ (nM) | mGlu1 $K_i$ (nM) |
|---|---|---|---|---|
| 243. | 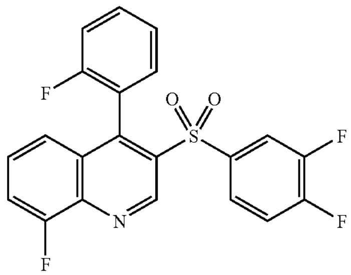 | 418.2 | *** | * |
| 244. | 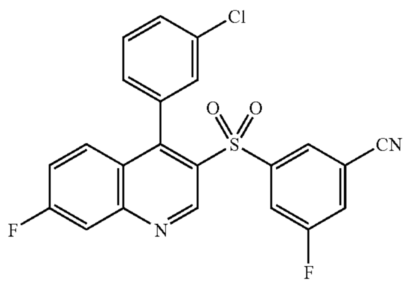 | 441.2 | *** | * |
| 245. | 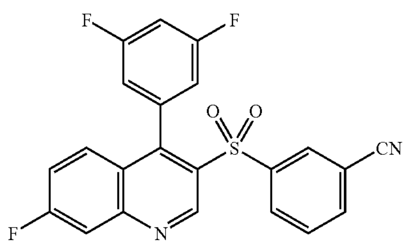 | 425.2 | * |  |
| 246. | 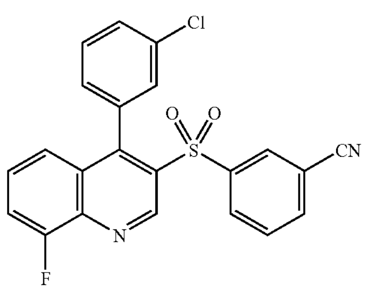 | 423.2 | *** | * |
| 247. | 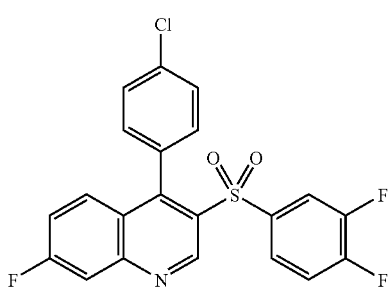 | 434.2 | *** | * |

TABLE 1-continued

| Comp. No. | Structure | (M + H)+ or M+ | mGlu5 K$_i$ (nM) | mGlu1 K$_i$ (nM) |
|---|---|---|---|---|
| 248. | 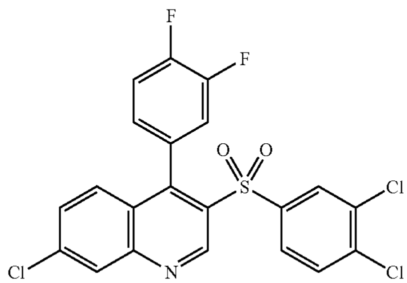 | 486.2 | * |  |
| 249. | 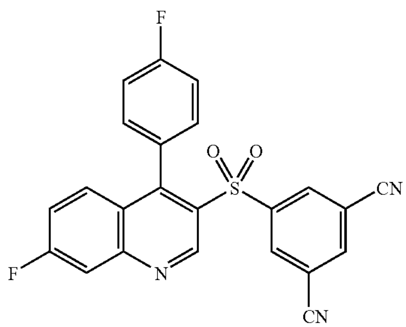 | 432.3 | *** | * |
| 250. | 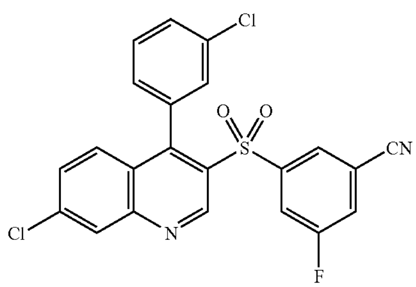 | 458.0 | * |  |
| 251. | 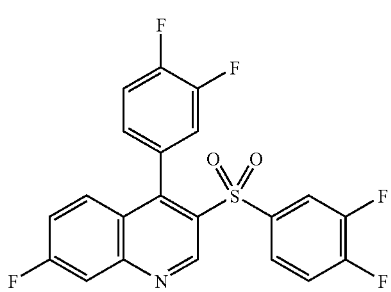 | 436.2 | *** | * |
| 252. | 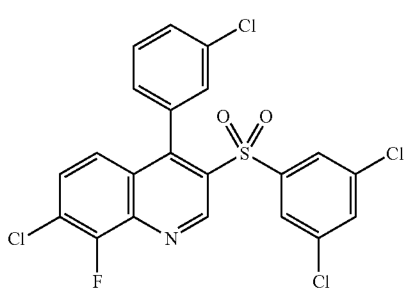 | 503.8 | * |  |

TABLE 1-continued

| Comp. No. | Structure | (M + H)+ or M+ | mGlu5 K$_i$ (nM) | mGlu1 K$_i$ (nM) |
|---|---|---|---|---|
| 253. | 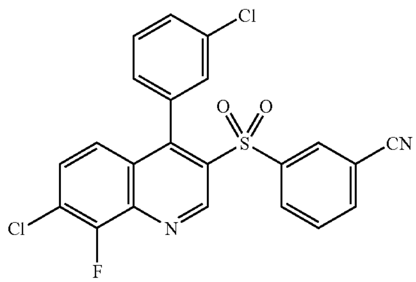 | 458.2 | * |  |
| 254. | 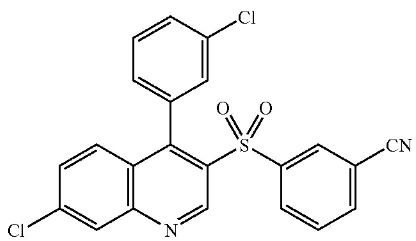 | 440.1 | * |  |
| 255. | 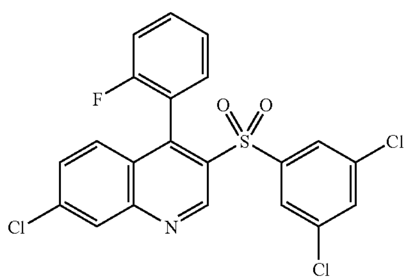 | 468.1 | * |  |
| 256. | 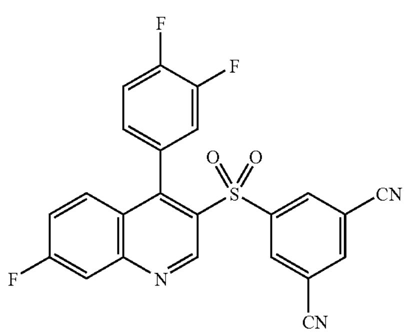 | 450.3 | *** | * |
| 257. | 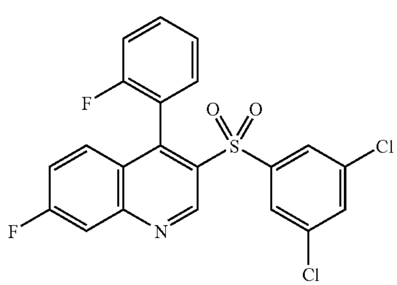 | 450.8 | *** | * |

TABLE 1-continued

| Comp. No. | Structure | (M + H)⁺ or M⁺ | mGlu5 K$_i$ (nM) | mGlu1 K$_i$ (nM) |
|---|---|---|---|---|
| 258. | 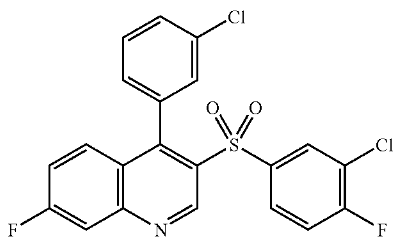 | 451.1 | * |  |
| 259. | 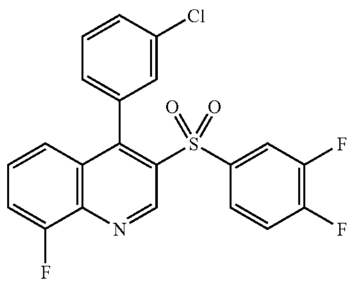 | 434.2 | *** | * |
| 260. | 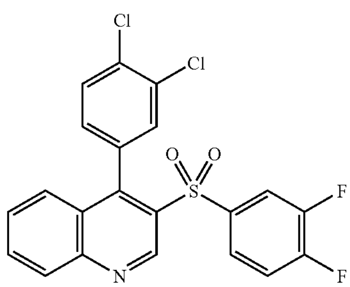 | 451.3 | *** | * |
| 261. | 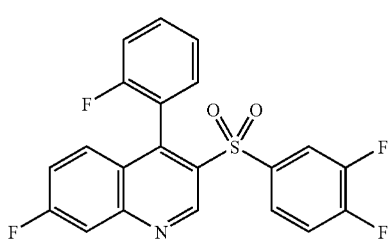 | 417.9 | *** | * |
| 262. | 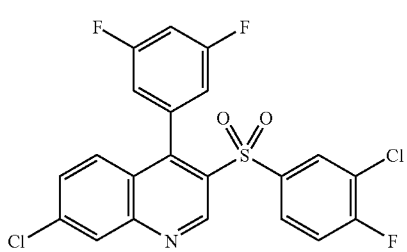 | 469.4 | * | * |

TABLE 1-continued

| Comp. No. | Structure | (M + H)+ or M+ | mGlu5 $K_i$ (nM) | mGlu1 $K_i$ (nM) |
|---|---|---|---|---|
| 263. | 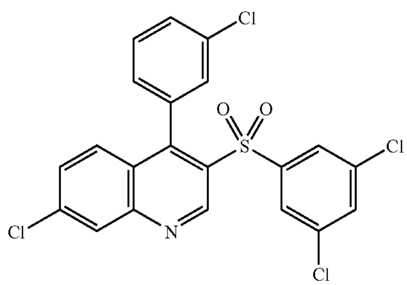 | 484.2 | * |  |
| 264. | 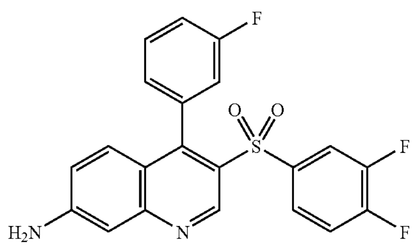 | 415.1 | * |  |
| 265. | 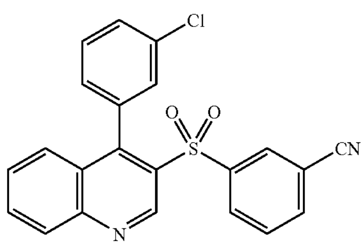 | 405.0 | *** | * |
| 266. | 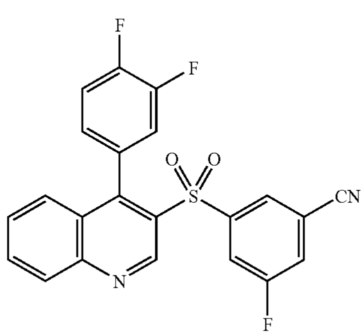 | 425.1 | *** | * |
| 267. | 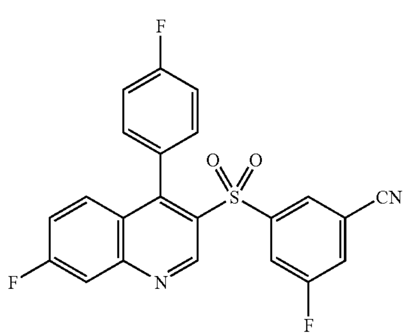 | 425.2 | *** | * |

TABLE 1-continued

| Comp. No. | Structure | (M + H)+ or M+ | mGlu5 $K_i$ (nM) | mGlu1 $K_i$ (nM) |
|---|---|---|---|---|
| 268. | 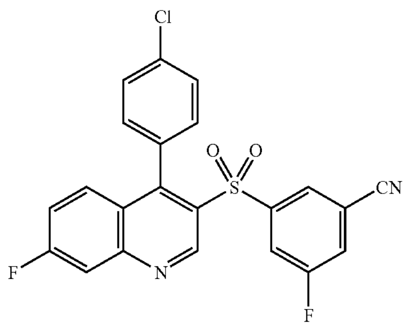 | 441.2 | *** | * |
| 269. | 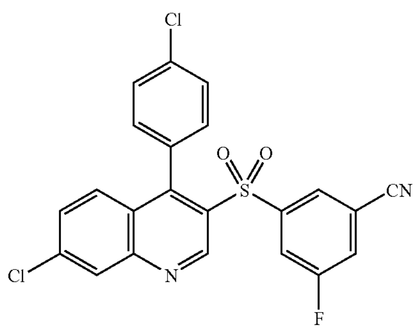 | 458.2 | *** | * |
| 270. | 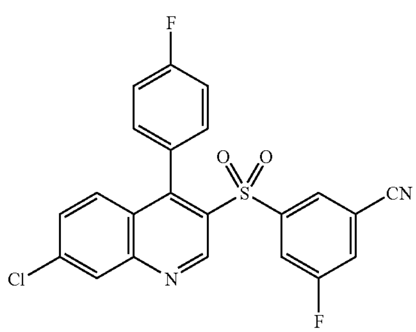 | 441.2 | *** | * |
| 271. | 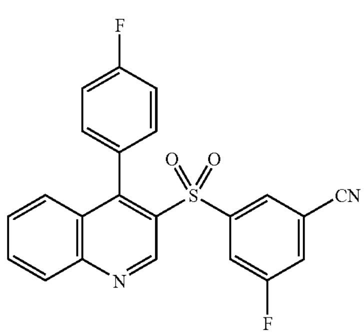 | 407.3 | *** | * |

TABLE 1-continued
| Comp. No. | Structure | (M + H)+ or M+ | mGlu5 K_i (nM) | mGlu1 K_i (nM) |
|---|---|---|---|---|
| 272. | 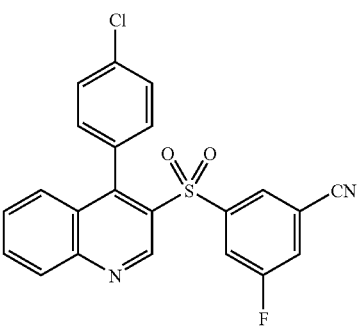 | 423.2 | *** | * |
| 273. | 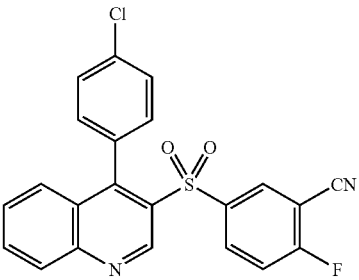 | 423.2 | *** | * |
| 274. | 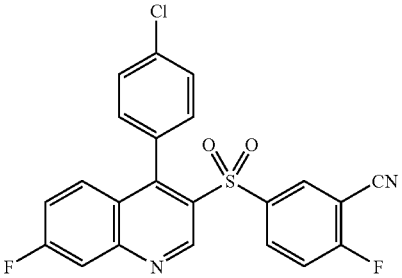 | 441.2 | *** | * |
| 275. | 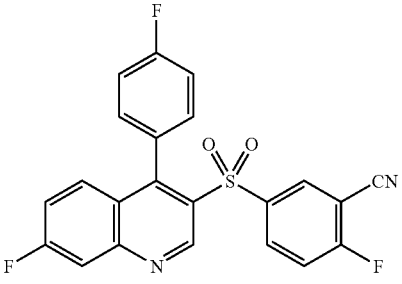 | 425.2 | *** | * |
| 276. | 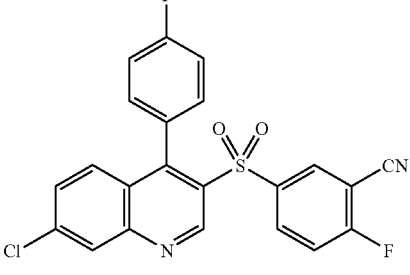 | 441.2 | * |  |

TABLE 1-continued

| Comp. No. | Structure | (M + H)+ or M+ | mGlu5 K_i (nM) | mGlu1 K_i (nM) |
|---|---|---|---|---|
| 277. | 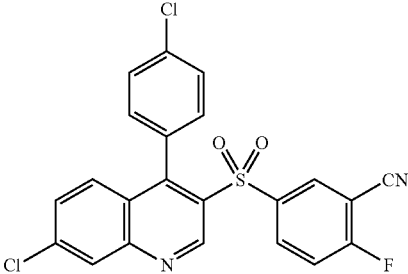 | 458.2 | * |  |
| 278. | 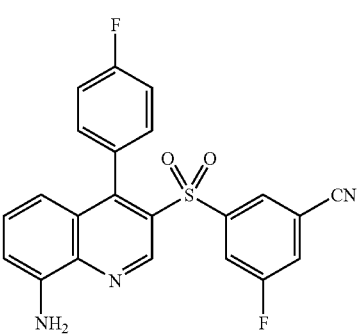 | 422.1 | *** | * |
| 279. | 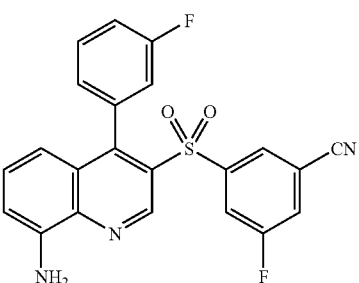 | 422.1 | *** | * |

*** $K_i < 200$ nM
** $200$ nM $< K_i < 500$ nM
* $500$ nM $< K_i$

While the invention has been depicted and described by reference to exemplary embodiments of the invention, such a reference does not imply a limitation on the invention, and no such limitation is to be inferred. The invention is capable of considerable modification, alteration, and equivalents in form and function, as will occur to those ordinarily skilled in the pertinent arts having the benefit of this disclosure. The depicted and described embodiments of the invention are exemplary only, and are not exhaustive of the scope of the invention. Consequently, the invention is intended to be limited only by the spirit and scope of the appended claims, giving full cognizance to equivalence in all respects.

We claim:

1. A compound having the formula (I):

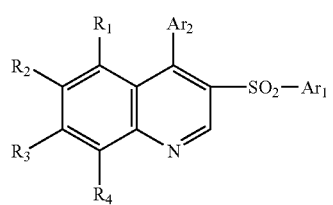

(I)

wherein
- Ar$_1$ represents an optionally substituted phenyl group, wherein the phenyl group is optionally substituted with one to three substituents selected from fluoro, chloro, cyano, methyl, and methoxy;
- Ar$_2$ represents a substituted phenyl group, wherein the substituted phenyl group is substituted with one to three substituents selected from fluoro, chloro, cyano, methyl, or methoxy;
- R$_1$, R$_2$, R$_3$ and R$_4$ represent independently a substituent selected from hydrogen, halogen, cyano, alkyl, alkoxy, hydroxy, trifluoromethyl, amino, alkylamino, dialkylamino, aminomethyl, alkylaminomethyl, and dialkylaminomethyl;

or salts thereof.

2. A compound according to claim 1, wherein:
- R$_1$, R$_2$, R$_3$ and R$_4$ represent independently a substituent selected from hydrogen, fluoro, chloro, cyano, methyl, methoxy, hydroxy, trifluoromethyl, amino, methylamino, dimethylamino, aminomethyl, methylaminomethyl, and dimethylaminomethyl;

or salts thereof.

3. A compound according to claim 1 selected from:
- 4-(4-chloro-phenyl)-3-(4-methyl-benzenesulfonyl)-quinoline,
- 7-chloro-3-(4-chloro-benzenesulfonyl)-4-(4-fluoro-phenyl)-quinoline,
- 8-chloro-4-(3-chloro-phenyl)-3-(3,4-dichloro-benzenesulfonyl)-quinoline,
- 7-fluoro-3-(4-fluoro-benzenesulfonyl)-4-(3-fluoro-phenyl)-quinoline,
- 4-(4-chloro-phenyl)-7-fluoro-3-(4-methoxy-benzenesulfonyl)-quinoline,
- 7-fluoro-3-(4-methoxy-benzenesulfonyl)-4-(4-methoxy-phenyl)-quinoline,
- 7-fluoro-3-(3-fluoro-benzenesulfonyl)-4-(3-fluoro-phenyl)-quinoline,
- 7-fluoro-3-(3-fluoro-benzenesulfonyl)-4-(4-fluoro-phenyl)-quinoline,
- 4-(3-chloro-phenyl)-3-(3,4-dimethyl-benzenesulfonyl)-7-fluoro-quinoline,
- 3-(3,4-dimethyl-benzenesulfonyl)-7-fluoro-4-(3-fluoro-phenyl)-quinoline,
- 3-(3,4-dimethyl-benzenesulfonyl)-7-fluoro-4-(3-methoxy-phenyl)-quinoline,
- 4-(3-chloro-phenyl)-8-fluoro-3-(4-fluoro-benzenesulfonyl)-quinoline,
- 4-(4-chloro-phenyl)-8-fluoro-3-(4-fluoro-benzenesulfonyl)-quinoline,
- 8-fluoro-3-(4-fluoro-benzenesulfonyl)-4-(3-fluoro-phenyl)-quinoline,
- 8-fluoro-3-(4-fluoro-benzenesulfonyl)-4-(3-methoxy-phenyl)-quinoline,
- 4-(4-chloro-phenyl)-6-fluoro-3-(4-methoxy-benzenesulfonyl)-quinoline,
- 4-(4-chloro-phenyl)-3-(3,4-dimethyl-benzenesulfonyl)-6-fluoro-quinoline,
- 4-(4-chloro-phenyl)-3-(3,5-difluoro-benzenesulfonyl)-7-fluoro-quinoline,
- 3-(3,5-difluoro-benzenesulfonyl)-7-fluoro-4-(4-fluoro-phenyl)-quinoline,
- 4-(4-chloro-phenyl)-3-(3-cyano-benzenesulfonyl)-7-fluoro-quinoline,
- 3-(3-cyano-benzenesulfonyl)-7-fluoro-4-(3-fluoro-phenyl)-quinoline,
- 3-(3-cyano-benzenesulfonyl)-7-fluoro-4-(4-fluoro-phenyl)-quinoline,
- 7-fluoro-3-(4-fluoro-benzenesulfonyl)-4-(4-fluoro-phenyl)-quinoline,
- 4-(4-chloro-phenyl)-7-fluoro-3-(3-fluoro-benzenesulfonyl)-quinoline,
- 4-(3-chloro-phenyl)-7-fluoro-3-(3-methoxy-benzenesulfonyl)-quinoline,
- 7-fluoro-4-(4-fluoro-phenyl)-3-(3-methoxy-benzenesulfonyl)-quinoline,
- 4-(4-chloro-phenyl)-3-(3,4-dimethyl-benzenesulfonyl)-7-fluoro-quinoline,
- 3-(3,4-dimethyl-benzenesulfonyl)-7-fluoro-4-(4-fluoro-phenyl)-quinoline,
- 4-(3-chloro-phenyl)-3-(3-chloro-4-methoxy-benzenesulfonyl)-7-fluoro-quinoline,
- 3-(3-chloro-4-methoxy-benzenesulfonyl)-7-fluoro-4-(3-fluoro-phenyl)-quinoline,
- 3-(3-chloro-4-methoxy-benzenesulfonyl)-7-fluoro-4-(4-fluoro-phenyl)-quinoline,
- 3-(3,5-dichloro-benzenesulfonyl)-8-fluoro-4-(4-fluoro-phenyl)-quinoline,
- 3-(3,5-difluoro-benzenesulfonyl)-8-fluoro-4-(3-fluoro-phenyl)-quinoline,
- 8-fluoro-3-(4-fluoro-benzenesulfonyl)-4-(4-methoxy-phenyl)-quinoline,
- 4-(3-chloro-phenyl)-8-fluoro-3-(4-methoxy-benzenesulfonyl)-quinoline,
- 4-(4-chloro-phenyl)-8-fluoro-3-(4-methoxy-benzenesulfonyl)-quinoline,
- 8-fluoro-4-(4-fluoro-phenyl)-3-(4-methoxy-benzenesulfonyl)-quinoline,
- 8-fluoro-3-(4-methoxy-benzenesulfonyl)-4-(4-methoxy-phenyl)-quinoline,
- 8-fluoro-3-(4-methoxy-benzenesulfonyl)-4-(3-methoxy-phenyl)-quinoline,
- 4-(3-chloro-phenyl)-8-fluoro-3-(3-fluoro-benzenesulfonyl)-quinoline,
- 4-(4-chloro-phenyl)-8-fluoro-3-(3-fluoro-benzenesulfonyl)-quinoline,
- 8-fluoro-3-(3-fluoro-benzenesulfonyl)-4-(3-fluoro-phenyl)-quinoline,
- 8-fluoro-3-(3-fluoro-benzenesulfonyl)-4-(4-methoxy-phenyl)-quinoline,
- 8-fluoro-3-(3-fluoro-benzenesulfonyl)-4-(3-methoxy-phenyl)-quinoline,
- 8-fluoro-3-(3-fluoro-benzenesulfonyl)-4-(4-fluoro-phenyl)-quinoline,
- 3-(3-cyano-benzenesulfonyl)-6-fluoro-4-(3-fluoro-phenyl)-quinoline,
- 3-(3-cyano-benzenesulfonyl)-6-fluoro-4-(3-methoxy-phenyl)-quinoline,
- 3-(3-cyano-benzenesulfonyl)-6-fluoro-4-(4-fluoro-phenyl)-quinoline,
- 4-(3-chloro-phenyl)-6-fluoro-3-(3-methoxy-benzenesulfonyl)-quinoline,
- 6-fluoro-4-(4-fluoro-phenyl)-3-(3-methoxy-benzenesulfonyl)-quinoline,
- 3-(3-chloro-4-methoxy-benzenesulfonyl)-6-fluoro-4-(4-methoxy-phenyl)-quinoline,
- 3-(3-chloro-4-methoxy-benzenesulfonyl)-6-fluoro-4-(3-methoxy-phenyl)-quinoline,
- 4-(4-chloro-phenyl)-7-fluoro-3-(4-fluoro-benzenesulfonyl)-quinoline,
- 3-(3,4-dimethyl-benzenesulfonyl)-7-fluoro-4-(4-methoxy-phenyl)-quinoline,
- 3-(3-chloro-4-methoxy-benzenesulfonyl)-4-(4-chloro-phenyl)-6-fluoro-quinoline, 3-(3-chloro-4-methoxy-benzenesulfonyl)-6-fluoro-4-(3-fluoro-phenyl)-quinoline,
3-(3,5-dichloro-benzenesulfonyl)-7-fluoro-4-(4-methoxy-phenyl)-quinoline,
3-(3,5-dichloro-benzenesulfonyl)-7-fluoro-4-(3-methoxy-phenyl)-quinoline,
3-(3,5-difluoro-benzenesulfonyl)-7-fluoro-4-(4-fluoro-phenyl)-quinoline,
4-(3-chloro-phenyl)-7-fluoro-3-(3-fluoro-4-methyl-benzenesulfonyl)-quinoline,
7-fluoro-3-(3-fluoro-4-methyl-benzenesulfonyl)-4-(3-fluoro-phenyl)-quinoline,
7-fluoro-3-(3-fluoro-4-methyl-benzenesulfonyl)-4-(4-fluoro-phenyl)-quinoline,
3-(3,5-difluoro-benzenesulfonyl)-7-fluoro-4-(3-fluoro-phenyl)-quinoline,
3-(3,5-difluoro-benzenesulfonyl)-7-fluoro-4-(4-methoxy-phenyl)-quinoline,
3-(3,5-difluoro-benzenesulfonyl)-7-fluoro-4-(3-methoxy-phenyl)-quinoline,
4-(3-chloro-phenyl)-3-(3-cyano-benzenesulfonyl)-7-fluoro-quinoline,
3-(3-cyano-benzenesulfonyl)-7-fluoro-4-(4-methoxy-phenyl)-quinoline,
3-(3-cyano-benzenesulfonyl)-7-fluoro-4-(3-methoxy-phenyl)-quinoline,
3-(3-chloro-4-methyl-benzenesulfonyl)-7-fluoro-4-(3-fluoro-phenyl)-quinoline,
3-(3,4-difluoro-benzenesulfonyl)-7-fluoro-4-(3-fluoro-phenyl)-quinoline,
3-(3,4-difluoro-benzenesulfonyl)-7-fluoro-4-(4-methoxy-phenyl)-quinoline,
3-(3,4-difluoro-benzenesulfonyl)-7-fluoro-4-(3-methoxy-phenyl)-quinoline,
3-(3,4-difluoro-benzenesulfonyl)-7-fluoro-4-(4-fluoro-phenyl)-quinoline,
3-(3-chloro-4-fluoro-benzenesulfonyl)-4-(4-chloro-phenyl)-7-fluoro-quinoline,
3-(3-chloro-4-fluoro-benzenesulfonyl)-7-fluoro-4-(3-fluoro-phenyl)-quinoline,
3-(3-chloro-4-fluoro-benzenesulfonyl)-7-fluoro-4-(4-methoxy-phenyl)-quinoline,
3-(3-chloro-4-fluoro-benzenesulfonyl)-7-fluoro-4-(4-fluoro-phenyl)-quinoline,
3-(3,5-dichloro-benzenesulfonyl)-8-fluoro-4-(3-fluoro-phenyl)-quinoline,
3-(3,5-dichloro-benzenesulfonyl)-8-fluoro-4-(4-methoxy-phenyl)-quinoline,
3-(3,5-dichloro-benzenesulfonyl)-8-fluoro-4-(3-methoxy-phenyl)-quinoline,
4-(3-chloro-phenyl)-8-fluoro-3-(3-fluoro-4-methyl-benzenesulfonyl)-quinoline,
4-(4-chloro-phenyl)-8-fluoro-3-(3-fluoro-4-methyl-benzenesulfonyl)-quinoline,
8-fluoro-3-(3-fluoro-4-methyl-benzenesulfonyl)-4-(3-fluoro-phenyl)-quinoline,
8-fluoro-3-(3-fluoro-4-methyl-benzenesulfonyl)-4-(4-methoxy-phenyl)-quinoline,
8-fluoro-3-(3-fluoro-4-methyl-benzenesulfonyl)-4-(3-methoxy-phenyl)-quinoline,
8-fluoro-3-(3-fluoro-4-methyl-benzenesulfonyl)-4-(4-fluoro-phenyl)-quinoline,
4-(3-chloro-phenyl)-3-(3,5-difluoro-benzenesulfonyl)-8-fluoro-quinoline,
4-(4-chloro-phenyl)-3-(3,5-difluoro-benzenesulfonyl)-8-fluoro-quinoline,
3-(3,5-difluoro-benzenesulfonyl)-8-fluoro-4-(4-methoxy-phenyl)-quinoline,
3-(3,5-difluoro-benzenesulfonyl)-8-fluoro-4-(3-methoxy-phenyl)-quinoline,
3-(3,5-difluoro-benzenesulfonyl)-8-fluoro-4-(4-fluoro-phenyl)-quinoline,
4-(4-chloro-phenyl)-3-(3,4-difluoro-benzenesulfonyl)-8-fluoro-quinoline,
3-(3,4-difluoro-benzenesulfonyl)-8-fluoro-4-(3-fluoro-phenyl)-quinoline,
3-(3,4-difluoro-benzenesulfonyl)-8-fluoro-4-(4-methoxy-phenyl)-quinoline,
3-(3,4-difluoro-benzenesulfonyl)-8-fluoro-4-(4-fluoro-phenyl)-quinoline,
3-(3,5-dichloro-benzenesulfonyl)-6-fluoro-4-(3-fluoro-phenyl)-quinoline,
3-(3,5-dichloro-benzenesulfonyl)-6-fluoro-4-(4-methoxy-phenyl)-quinoline,
3-(3,5-dichloro-benzenesulfonyl)-6-fluoro-4-(3-methoxy-phenyl)-quinoline,
4-(3-chloro-phenyl)-6-fluoro-3-(3-fluoro-4-methyl-benzenesulfonyl)-quinoline,
6-fluoro-3-(3-fluoro-4-methyl-benzenesulfonyl)-4-(3-fluoro-phenyl)-quinoline,
6-fluoro-3-(3-fluoro-4-methyl-benzenesulfonyl)-4-(4-methoxy-phenyl)-quinoline,
6-fluoro-3-(3-fluoro-4-methyl-benzenesulfonyl)-4-(3-methoxy-phenyl)-quinoline,
6-fluoro-3-(3-fluoro-4-methyl-benzenesulfonyl)-4-(4-fluoro-phenyl)-quinoline,
4-(3-chloro-phenyl)-3-(3-cyano-benzenesulfonyl)-6-fluoro-quinoline,
4-(4-chloro-phenyl)-3-(3-cyano-benzenesulfonyl)-6-fluoro-quinoline,
3-(3-cyano-benzenesulfonyl)-6-fluoro-4-(4-methoxy-phenyl)-quinoline,
3-(3-chloro-4-methyl-benzenesulfonyl)-4-(3-chloro-phenyl)-6-fluoro-quinoline,
3-(3-chloro-4-methyl-benzenesulfonyl)-4-(4-chloro-phenyl)-6-fluoro-quinoline,
3-(3-chloro-4-methyl-benzenesulfonyl)-6-fluoro-4-(3-fluoro-phenyl)-quinoline,
3-(3-chloro-4-methyl-benzenesulfonyl)-6-fluoro-4-(3-methoxy-phenyl)-quinoline,
3-(3-chloro-4-methyl-benzenesulfonyl)-6-fluoro-4-(4-fluoro-phenyl)-quinoline,
4-(4-chloro-phenyl)-6-fluoro-3-(3-methoxy-benzenesulfonyl)-quinoline,
6-fluoro-3-(3-methoxy-benzenesulfonyl)-4-(3-methoxy-phenyl)-quinoline,
3-(3,4-dimethyl-benzenesulfonyl)-6-fluoro-4-(3-fluoro-phenyl)-quinoline,
3-(3,4-dimethyl-benzenesulfonyl)-6-fluoro-4-(4-methoxy-phenyl)-quinoline,
3-(3,4-dimethyl-benzenesulfonyl)-6-fluoro-4-(4-fluoro-phenyl)-quinoline,
3-(3,4-difluoro-benzenesulfonyl)-6-fluoro-4-(3-fluoro-phenyl)-quinoline,
3-(3,4-difluoro-benzenesulfonyl)-6-fluoro-4-(4-fluoro-phenyl)-quinoline,
3-(3-chloro-4-fluoro-benzenesulfonyl)-4-(4-chloro-phenyl)-6-fluoro-quinoline,
3-(3-chloro-4-fluoro-benzenesulfonyl)-6-fluoro-4-(3-methoxy-phenyl)-quinoline,
3-(3-chloro-4-fluoro-benzenesulfonyl)-6-fluoro-4-(4-fluoro-phenyl)-quinoline, 4-(3-chloro-phenyl)-3-(3,5-dichloro-benzenesulfonyl)-7-fluoro-quinoline,
4-(4-chloro-phenyl)-3-(3,5-dichloro-benzenesulfonyl)-7-fluoro-quinoline,
4-(3-chloro-phenyl)-3-(3,5-dichloro-benzenesulfonyl)-8-fluoro-quinoline,
4-(4-chloro-phenyl)-3-(3,5-dichloro-benzenesulfonyl)-8-fluoro-quinoline,
4-(3-chloro-phenyl)-3-(3,5-dichloro-benzenesulfonyl)-6-fluoro-quinoline,
4-(4-chloro-phenyl)-3-(3,5-dichloro-benzenesulfonyl)-6-fluoro-quinoline,
6-fluoro-3-(4-methoxy-benzenesulfonyl)-4-(4-methoxy-phenyl)-quinoline,
7-chloro-4-(4-chloro-phenyl)-3-(3,5-difluoro-benzenesulfonyl)-quinoline,
7-chloro-4-(4-chloro-phenyl)-3-(3,4-difluoro-benzenesulfonyl)-quinoline,
7-chloro-4-(4-chloro-phenyl)-3-(3-cyano-benzenesulfonyl)-quinoline,
7-chloro-3-(3,5-dichloro-benzenesulfonyl)-4-(4-fluoro-phenyl)-quinoline,
7-chloro-3-(4-fluoro-benzenesulfonyl)-4-(4-fluoro-phenyl)-quinoline,
7-chloro-3-(3-fluoro-benzenesulfonyl)-4-(4-fluoro-phenyl)-quinoline,
7-chloro-3-(3,4-difluoro-benzenesulfonyl)-4-(4-fluoro-phenyl)-quinoline,
7-chloro-3-(3-chloro-4-fluoro-benzenesulfonyl)-4-(4-fluoro-phenyl)-quinoline and 7-chloro-3-(3-cyano-5-fluoro-benzenesulfonyl)-4-(4-fluoro-phenyl)-quinoline
6-chloro-3-(3-chloro-4-fluoro-benzenesulfonyl)-4-(4-chloro-phenyl)-7-fluoro-quinoline,
6-chloro-3-(3-chloro-4-fluoro-benzenesulfonyl)-7-fluoro-4-(4-fluoro-phenyl)-quinoline,
3-(3-chloro-4-fluoro-benzenesulfonyl)-7-cyano-4-(2-fluoro-phenyl)-quinoline,
7-chloro-3-(3,4-difluoro-benzenesulfonyl)-8-fluoro-4-(3-fluoro-phenyl)-quinoline,
7-chloro-3-(3-chloro-4-fluoro-benzenesulfonyl)-4-(4-fluoro-phenyl)-8-fluoro-quinoline,
7-chloro-3-(3-chloro-4-fluoro-benzenesulfonyl)-8-fluoro-4-(3-fluoro-phenyl)-quinoline,
7-chloro-4-(4-chloro-phenyl)-3-(3,4-difluoro-benzenesulfonyl)-8-fluoro-quinoline,
7-chloro-3-(3-chloro-4-fluoro-benzenesulfonyl)-8-fluoro-4-(4-fluoro-phenyl)-quinoline,
3-(3-cyano-4-fluoro-benzenesulfonyl)-4-(3-fluoro-phenyl)-quinoline,
3-(3-cyano-5-fluoro-benzenesulfonyl)-4-(3-fluoro-phenyl)-quinoline,
3-(3-chloro-4-fluoro-benzenesulfonyl)-4-(4-chloro-phenyl)-8-fluoro-quinoline,
3-(3-chloro-4-fluoro-benzenesulfonyl)-8-fluoro-4-(2-fluoro-phenyl)-quinoline,
3-(3-chloro-4-fluoro-benzenesulfonyl)-8-fluoro-4-(3-fluoro-phenyl)-quinoline,
3-(3-cyano-4-fluoro-benzenesulfonyl)-4-(4-fluoro-phenyl)-quinoline,
3-(3-chloro-4-fluoro-benzenesulfonyl)-8-fluoro-4-(4-fluoro-phenyl)-quinoline,
3-(3-cyano-benzenesulfonyl)-8-fluoro-4-(2-fluoro-phenyl)-quinoline,
3-(3-cyano-benzenesulfonyl)-4-(3-fluoro-phenyl)-quinoline,
3-(3-cyano-benzenesulfonyl)-8-fluoro-4-(3-fluoro-phenyl)-quinoline,
3-(3-cyano-4-fluoro-benzenesulfonyl)-7-fluoro-4-(3-fluoro-phenyl)-quinoline,
4-(3-chloro-phenyl)-3-(3-cyano-4-fluoro-benzenesulfonyl)-quinoline,
3-(3-cyano-5-fluoro-benzenesulfonyl)-7-fluoro-4-(4-fluoro-phenyl)-quinoline,
7-chloro-3-(3-cyano-4-fluoro-benzenesulfonyl)-4-(3-fluoro-phenyl)-quinoline,
3-(3,5-dichloro-benzenesulfonyl)-4-(3,4-difluoro-phenyl)-8-fluoro-quinoline,
7-chloro-3-(3-cyano-5-fluoro-benzenesulfonyl)-4-(3-fluoro-phenyl)-quinoline,
3-(3-cyano-benzenesulfonyl)-8-fluoro-4-(4-fluoro-phenyl)-quinoline,
3-(3,5-dichloro-benzenesulfonyl)-8-fluoro-4-(2-fluoro-phenyl)-quinoline,
3-(3-chloro-4-fluoro-benzenesulfonyl)-7-fluoro-4-(2-fluoro-phenyl)-quinoline,
4-(4-chloro-phenyl)-3-(3-cyano-benzenesulfonyl)-8-fluoro-quinoline,
4-(3-chloro-phenyl)-3-(3-cyano-5-fluoro-benzenesulfonyl)-quinoline,
7-chloro-3-(3-cyano-benzenesulfonyl)-4-(2-fluoro-phenyl)-quinoline,
3-(3-cyano-5-fluoro-benzenesulfonyl)-7-fluoro-4-(3-fluoro-phenyl)-quinoline,
3-(3-chloro-4-fluoro-benzenesulfonyl)-4-(3-chloro-phenyl)-8-fluoro-quinoline,
3-(3-cyano-benzenesulfonyl)-7-fluoro-4-(2-fluoro-phenyl)-quinoline,
3-(3-cyano-5-fluoro-benzenesulfonyl)-4-(3,4-difluoro-phenyl)-7-fluoro-quinoline,
3-(3-cyano-4-fluoro-benzenesulfonyl)-4-(3,4-dichloro-phenyl)-quinoline,
7-chloro-3-(3-chloro-4-fluoro-benzenesulfonyl)-4-(2-fluoro-phenyl)-quinoline,
7-chloro-3-(3-cyano-benzenesulfonyl)-4-(3-fluoro-phenyl)-quinoline,
4-(3-chloro-phenyl)-3-(3-cyano-4-fluoro-benzenesulfonyl)-7-fluoro-quinoline,
3-(3,4-difluoro-benzenesulfonyl)-4-(3,5-difluoro-phenyl)-8-fluoro-quinoline,
3-(3,4-difluoro-benzenesulfonyl)-4-(4-fluoro-phenyl)-quinoline,
3-(3,4-difluoro-benzenesulfonyl)-4-(3,4-difluoro-phenyl)-8-fluoro-quinoline,
3-(3,5-dichloro-benzenesulfonyl)-4-(3,4-difluoro-phenyl)-7-fluoro-quinoline,
3-(3,4-difluoro-benzenesulfonyl)-4-(3-fluoro-phenyl)-quinoline,
7-chloro-3-(3-cyano-benzenesulfonyl)-4-(4-fluoro-phenyl)-quinoline,
7-chloro-4-(3-chloro-phenyl)-3-(3-cyano-4-fluoro-benzenesulfonyl)-quinoline,
3-(3,4-difluoro-benzenesulfonyl)-8-fluoro-4-(2-fluoro-phenyl)-quinoline,
4-(3-chloro-phenyl)-3-(3-cyano-5-fluoro-benzenesulfonyl)-7-fluoro-quinoline,
3-(3-cyano-benzenesulfonyl)-4-(3,5-difluoro-phenyl)-7-fluoro-quinoline,
4-(3-chloro-phenyl)-3-(3-cyano-benzenesulfonyl)-8-fluoro-quinoline,
4-(4-chloro-phenyl)-3-(3,4-difluoro-benzenesulfonyl)-7-fluoro-quinoline,
7-chloro-3-(3,4-dichloro-benzenesulfonyl)-4-(3,4-difluoro-phenyl)-quinoline, 3-(3,5-dicyano-benzenesulfonyl)-7-fluoro-4-(4-fluoro-phenyl)-quinoline,
7-chloro-3-(3-chloro-5-fluoro-benzenesulfonyl)-4-(3-chloro-phenyl)-quinoline,
3-(3,4-difluoro-benzenesulfonyl)-4-(3,4-difluoro-phenyl)-7-fluoro-quinoline,
7-chloro-4-(3-chloro-phenyl)-3-(3,5-dichloro-benzenesulfonyl)-8-fluoro-quinoline,
7-chloro-4-(3-chloro-phenyl)-3-(3-cyano-benzenesulfonyl)-8-fluoro-quinoline,
7-chloro-4-(3-chloro-phenyl)-3-(3-cyano-benzenesulfonyl)-quinoline,
7-chloro-3-(3,5-dichloro-benzenesulfonyl)-4-(2-fluoro-phenyl)-quinoline,
3-(3,5-dicyano-benzenesulfonyl)-4-(3,4-difluoro-phenyl)-7-fluoro-quinoline,
3-(3,5-dichloro-benzenesulfonyl)-7-fluoro-4-(2-fluoro-phenyl)-quinoline,
3-(3-chloro-4-fluoro-benzenesulfonyl)-4-(3-chloro-phenyl)-7-fluoro-quinoline,
4-(3-chloro-phenyl)-3-(3,4-difluoro-benzenesulfonyl)-8-fluoro-quinoline,
4-(3,4-dichloro-phenyl)-3-(3,4-difluoro-benzenesulfonyl)-quinoline,
3-(3,4-difluoro-benzenesulfonyl)-7-fluoro-4-(2-fluoro-phenyl)-quinoline,
7-chloro-3-(3-chloro-4-fluoro-benzenesulfonyl)-4-(3,5-difluoro-phenyl)-quinoline,
7-chloro-4-(3-chloro-phenyl)-3-(3,5-dichloro-benzenesulfonyl)-quinoline,
7-amino-3-(3,4-difluoro-benzenesulfonyl)-4-(3-fluoro-phenyl)-quinoline,
4-(3-chloro-phenyl)-3-(3-cyano-benzenesulfonyl)-quinoline,
3-(3-cyano-5-fluoro-benzenesulfonyl)-4-(3,4-difluoro-phenyl)-quinoline,
3-(3-cyano-5-fluoro-benzenesulfonyl)-7-fluoro-4-(4-fluoro-phenyl)-quinoline,
4-(4-chloro-phenyl)-3-(3-cyano-5-fluoro-benzenesulfonyl)-7-fluoro-quinoline,
7-chloro-3-(3-chloro-5-fluoro-benzenesulfonyl)-4-(4-chloro-phenyl)-quinoline,
7-chloro-3-(3-chloro-5-fluoro-benzenesulfonyl)-4-(4-fluoro-phenyl)-quinoline,
3-(3-chloro-5-fluoro-benzenesulfonyl)-4-(4-fluoro-phenyl)-quinoline,
3-(3-chloro-5-fluoro-benzenesulfonyl)-4-(4-chloro-phenyl)-quinoline,
3-(3-chloro-4-fluoro-benzenesulfonyl)-4-(4-chloro-phenyl)-quinoline,
3-(3-chloro-4-fluoro-benzenesulfonyl)-4-(4-chloro-phenyl)-7-fluoro-quinoline,
3-(3-chloro-4-fluoro-benzenesulfonyl)-7-fluoro-4-(4-fluoro-phenyl)-quinoline,
7-chloro-3-(3-chloro-4-fluoro-benzenesulfonyl)-4-(4-fluoro-phenyl)-quinoline,
7-chloro-3-(3-chloro-4-fluoro-benzenesulfonyl)-4-(4-chloro-phenyl)-quinoline,
7-amino-3-(3-chloro-5-fluoro-benzenesulfonyl)-4-(4-fluoro-phenyl)-quinoline, and,
7-amino-3-(3-chloro-5-fluoro-benzenesulfonyl)-4-(3-fluoro-phenyl)-quinoline;
or salts thereof.

4. A compound according to claim 1, wherein the compound is a mGluR1 and mGluR5 receptor subtype preferring ligand.

5. A process for the preparation of a compound of formula (I):

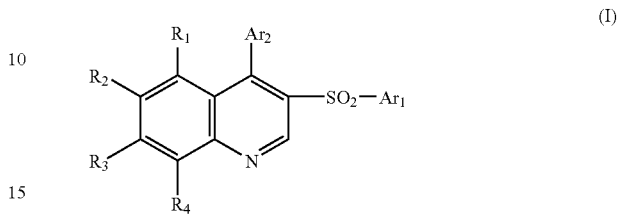

wherein $Ar_1$ represents an optionally substituted phenyl group, wherein the phenyl group is optionally substituted with one to three substituents selected from fluoro, chloro, cyano, methyl, and methoxy;

$Ar_2$ represents a substituted phenyl group, wherein the substituted phenyl group is substituted with one to three substituents selected from fluoro, chloro, cyano, methyl, or methoxy;

$R_1$, $R_2$, $R_3$ and $R_4$ represent independently a substituent selected from hydrogen, halogen, cyano, alkyl, alkoxy, hydroxy, trifluoromethyl, amino, alkylamino, dialkylamino, aminomethyl, alkylaminomethyl, and dialkylaminomethyl;

or salts thereof, comprising:

reacting a compound of formula (II):

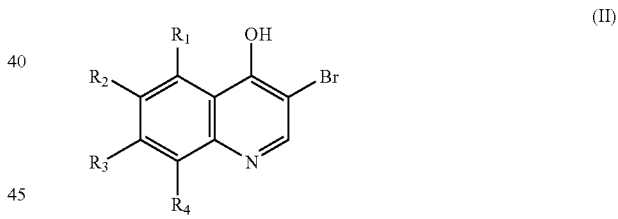

wherein $R_1$, $R_2$, $R_3$ and $R_4$ are as defined above for a compound of formula (I), with a compound of formula (III):

wherein $Ar_1$ is as defined above for compounds of formula (I), M is selected from alkali metals and alkaline-earth metals, to give a compound of formula (IV):

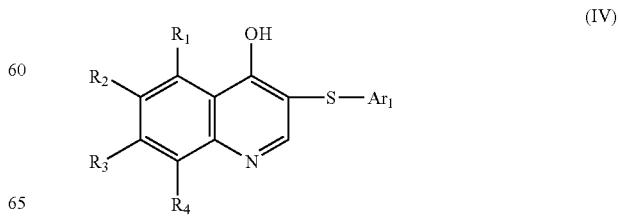

wherein
Ar₁, R₁, R₂, R₃ and R₄ and are as defined above for compounds of formula (I);
thereafter oxidizing the compound of formula (IV) to obtain a compound of formula (V):

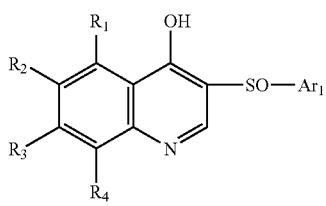
(V)

wherein
Ar₁, R₁, R₂, R₃ and R₄ are as defined above for compounds of formula (I);
thereafter oxidizing the compound of formula (V) to obtain a compound of formula (VI):

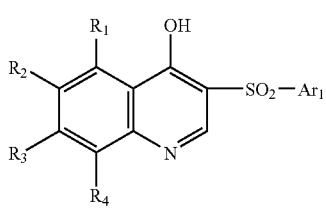
(VI)

wherein
Ar₁, R₁, R₂, R₃ and R₄ are as defined above for compounds of formula (I);
thereafter converting the compound of formula (VI) to a compound of formula (VII):

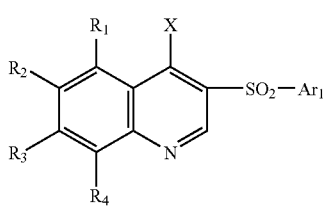
(VII)

wherein
Ar₁, R₁, R₂, R₃ and R₄ are as defined above for compounds of formula (I), and X is selected from chloro, bromo, benzenesulfonyloxy, 4-fluoro-benzenesulfonyloxy, 4-methyl-benzenesulfonyloxy, methanesulfonyloxy and trifluoromethanesulfonyloxy;
thereafter reacting the compound of formula (VII) with a boronic acid derivative of formula (VIII):

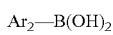   Ar₂—B(OH)₂   (VIII)

wherein
Ar₂ is as defined above for a compound of formula (I), in the presence of base and catalyst in a solvent to obtain the compound of formula (I); and,
optionally thereafter forming salts of formula (I).

6. A method according to claim 5, further comprising interconverting one compound of formula (I) to a different compound of formula (I).

7. A process for the preparation of a compound of formula (I):

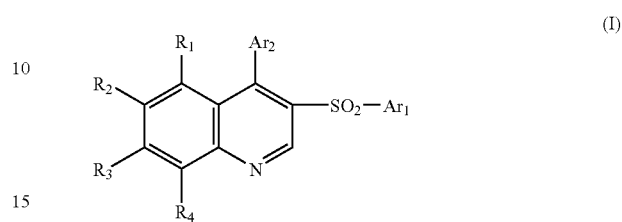
(I)

wherein:
Ar₁ represents an optionally substituted phenyl group, wherein the phenyl group is optionally substituted with one to three substituents selected from fluoro, chloro, cyano, methyl, and methoxy;
Ar₂ represents a substituted phenyl group, wherein the substituted phenyl group is substituted with one to three substituents selected from fluoro, chloro, cyano, methyl, or methoxy;
R₁, R₂, R₃ and R₄ represent independently a substituent selected from hydrogen, halogen, cyano, alkyl, alkoxy, hydroxy, trifluoromethyl, amino, alkylamino, dialkylamino, aminomethyl, alkylaminomethyl, and dialkylaminomethyl;
or salts thereof, comprising:
reacting a compound of formula (IX):

   Ar₁—SO₂Na   (IX)

wherein: Ar₁ is as defined above for a compound of formula (I), with α-halogen-acetic acid esters of formula (X):

   Hlg-CH₂—COOR₅   (X)

wherein: Hlg is halogen and R₅ is an ethyl or methyl group, to obtain a compound of formula (XI):

   Ar₁—SO₂—CH₂—COOR₅   (XI)

wherein: Ar₁ is as defined above for a compound of formula (I) and R₅ is as defined above for compounds of formula (X);
thereafter reacting the compound of formula (XI) with a trialkyl orthoformate of formula (XII):

   CH(OR₆)₃   (XII)

wherein: R₆ is an ethyl or methyl group, to obtain a compound of formula (XIII):

(XIII)

wherein: Ar₁ is as defined above for a compound of formula (I), R₅ is as defined above for compounds of formula (X) and R₆ is as defined above for compounds of formula (XII);

thereafter reacting a compound of formula (XIII) with an aniline derivative of formula (XIV):

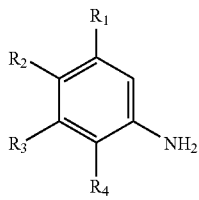

(XIV)

wherein: $R_1$, $R_2$, $R_3$ and $R_4$ are as defined above for a compound of formula (I), to obtain a compound of formula (VI):

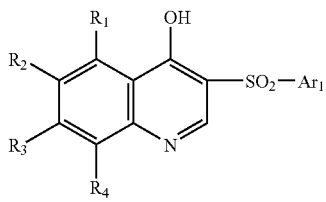

(VI)

wherein: $Ar_1$, $R_1$, $R_2$, $R_3$ and $R_4$ are as defined above for a compound of formula (I);

thereafter converting the compound of formula (VI) to a compound of formula (VII):

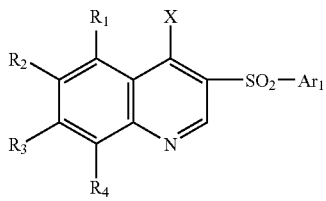

(VII)

wherein:

$Ar_1$, $R_1$, $R_2$, $R_3$ and $R_4$ are as defined above for compounds of formula (I), and X is selected from chloro, bromo, benzenesulfonyloxy, 4-fluoro-benzenesulfonyloxy, 4-methyl-benzenesulfonyloxy, methanesulfonyloxy and trifluoromethanesulfonyloxy;

thereafter reacting the compound of formula (VII) with a boronic acid derivative of formula (VIII):

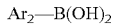 $Ar_2$—$B(OH)_2$ (VIII)

wherein $Ar_2$ is as defined above for a compound of formula (I), in the presence of base and catalyst in a solvent to obtain the compound of formula (I); and, optionally thereafter forming salts of compounds of formula (I).

8. A pharmaceutical formulation comprising a therapeutically effective amount of a compound of formula (I):

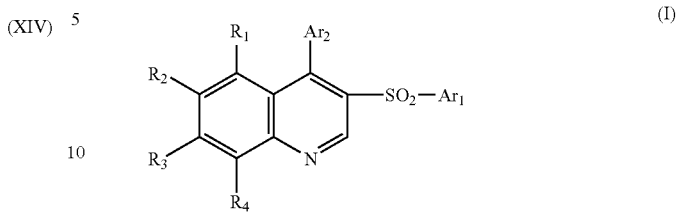

(I)

wherein
$Ar_1$ represents an optionally substituted phenyl group, wherein the phenyl group is optionally substituted with one to three substituents selected from fluoro, chloro, cyano, methyl, and methoxy;
$Ar_2$ represents a substituted phenyl or an optionally substituted heteroaryl group, wherein the substituted phenyl group is substituted with one to three substituents selected from fluoro, chloro, cyano, methyl, or methoxy;
$R_1$, $R_2$, $R_3$ and $R_4$ represent independently a substituent selected from hydrogen, halogen, cyano, alkyl, alkoxy, hydroxy, trifluoromethyl, amino, alkylamino, dialkylamino, aminomethyl, alkylaminomethyl, and dialkylaminomethyl;
or salts thereof and, one or more physiologically acceptable diluents, excipients or inert carriers.

9. A pharmaceutical formulation comprising a therapeutically effective amount of a compound of formula (I):

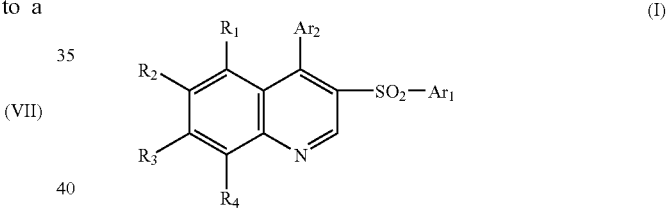

(I)

wherein
$Ar_1$ represents an optionally substituted phenyl group, wherein the phenyl group is optionally substituted with one to three substituents selected from fluoro, chloro, cyano, methyl, and methoxy;
$Ar_2$ represents a substituted phenyl group, wherein the substituted phenyl group is substituted with one to three substituents selected from fluoro, chloro, cyano, methyl, or methoxy;
$R_1$, $R_2$, $R_3$ and $R_4$ represent independently a substituent selected from hydrogen, fluoro, chloro, cyano, methyl, methoxy, hydroxy, trifluoromethyl, amino, methylamino, dimethylamino, aminomethyl, methylaminomethyl, and dimethylaminomethyl;
or physiologically acceptable salts thereof; and, one or more physiologically acceptable diluents, excipients or inert carriers.

10. A compound selected from the group consisting of:
3-(3-cyano-benzenesulfonyl)-7-fluoro-4-(4-fluoro-phenyl)-quinoline;
3-(3-chloro-4-fluoro-benzenesulfonyl)-4-(4-chloro-phenyl)-7-fluoro-quinoline;
3-(3-chloro-4-fluoro-benzenesulfonyl)-7-fluoro-4-(4-fluoro-phenyl)-quinoline;
7-chloro-3-(3-cyano-5-fluoro-benzenesulfonyl)-4-(3-fluoro-phenyl)-quinoline;

3-(3-chloro-4-fluoro-benzenesulfonyl)-7-fluoro-4-(2-fluoro-phenyl)-quinoline;
4-(4-chloro-phenyl)-3-(3-cyano-benzenesulfonyl)-7-fluoro-quinoline;
3-(3-cyano-5-fluoro-benzenesulfonyl)-7-fluoro-4-(3-fluoro-phenyl)-quinoline;
7-chloro-3-(3-cyano-benzenesulfonyl)-4-(3-fluoro-phenyl)-quinoline;
4-(3-chloro-phenyl)-3-(3-cyano-4-fluoro-benzenesulfonyl)-7-fluoro-quinoline;
7-chloro-3-(3-cyano-benzenesulfonyl)-4-(4-fluoro-phenyl)-quinoline;
4-(4-chloro-phenyl)-3-(3,4-difluoro-benzenesulfonyl)-7-fluoro-quinoline; and
4-(4-chloro-phenyl)-3-(3-cyano-5-fluoro-benzenesulfonyl)-7-fluoro-quinoline,
or a salt thereof.

11. A pharmaceutical formulation comprising a therapeutically effective amount of a compound selected from the group consisting of:
3-(3-cyano-benzenesulfonyl)-7-fluoro-4-(4-fluoro-phenyl)-quinoline;
3-(3-chloro-4-fluoro-benzenesulfonyl)-4-(4-chloro-phenyl)-7-fluoro-quinoline;
3-(3-chloro-4-fluoro-benzenesulfonyl)-7-fluoro-4-(4-fluoro-phenyl)-quinoline;
7-chloro-3-(3-cyano-5-fluoro-benzenesulfonyl)-4-(3-fluoro-phenyl)-quinoline;
3-(3-chloro-4-fluoro-benzenesulfonyl)-7-fluoro-4-(2-fluoro-phenyl)-quinoline;
4-(4-chloro-phenyl)-3-(3-cyano-benzenesulfonyl)-7-fluoro-quinoline;
3-(3-cyano-5-fluoro-benzenesulfonyl)-7-fluoro-4-(3-fluoro-phenyl)-quinoline;
7-chloro-3-(3-cyano-benzenesulfonyl)-4-(3-fluoro-phenyl)-quinoline;
4-(3-chloro-phenyl)-3-(3-cyano-4-fluoro-benzenesulfonyl)-7-fluoro-quinoline;
7-chloro-3-(3-cyano-benzenesulfonyl)-4-(4-fluoro-phenyl)-quinoline;
4-(4-chloro-phenyl)-3-(3,4-difluoro-benzenesulfonyl)-7-fluoro-quinoline; and
4-(4-chloro-phenyl)-3-(3-cyano-5-fluoro-benzenesulfonyl)-7-fluoro-quinoline,
or a physiologically acceptable salt thereof, and one or more physiologically acceptable diluents, excipients or inert carriers.

12. A compound selected from the group consisting of:
3-(3-cyano-benzenesulfonyl)-7-fluoro-4-(4-fluoro-phenyl)-quinoline;
3-(3-chloro-4-fluoro-benzenesulfonyl)-4-(4-chloro-phenyl)-7-fluoro-quinoline;
3-(3-chloro-4-fluoro-benzenesulfonyl)-7-fluoro-4-(4-fluoro-phenyl)-quinoline; and
7-chloro-3-(3-cyano-5-fluoro-benzenesulfonyl)-4-(3-fluoro-phenyl)-quinoline;
or a salt thereof.

13. A pharmaceutical formulation comprising a therapeutically effective amount of a compound selected from the group consisting of:
3-(3-cyano-benzenesulfonyl)-7-fluoro-4-(4-fluoro-phenyl)-quinoline;
3-(3-chloro-4-fluoro-benzenesulfonyl)-4-(4-chloro-phenyl)-7-fluoro-quinoline;
3-(3-chloro-4-fluoro-benzenesulfonyl)-7-fluoro-4-(4-fluoro-phenyl)-quinoline; and
7-chloro-3-(3-cyano-5-fluoro-benzenesulfonyl)-4-(3-fluoro-phenyl)-quinoline;
or a physiologically acceptable salt thereof, and one or more physiologically acceptable diluents, excipients or inert carriers.

14. A compound selected from the group consisting of:
3-(3-chloro-4-fluoro-benzenesulfonyl)-7-fluoro-4-(2-fluoro-phenyl)-quinoline;
4-(4-chloro-phenyl)-3-(3-cyano-benzenesulfonyl)-7-fluoro-quinoline;
3-(3-cyano-5-fluoro-benzenesulfonyl)-7-fluoro-4-(3-fluoro-phenyl)-quinoline; and
7-chloro-3-(3-cyano-benzenesulfonyl)-4-(3-fluoro-phenyl)-quinoline;
or a salt thereof.

15. A pharmaceutical formulation comprising a therapeutically effective amount of a compound selected from the group consisting of:
3-(3-chloro-4-fluoro-benzenesulfonyl)-7-fluoro-4-(2-fluoro-phenyl)-quinoline;
4-(4-chloro-phenyl)-3-(3-cyano-benzenesulfonyl)-7-fluoro-quinoline;
3-(3-cyano-5-fluoro-benzenesulfonyl)-7-fluoro-4-(3-fluoro-phenyl)-quinoline; and
7-chloro-3-(3-cyano-benzenesulfonyl)-4-(3-fluoro-phenyl)-quinoline;
or a physiologically acceptable salt thereof, and one or more physiologically acceptable diluents, excipients or inert carriers.

16. A compound selected from the group consisting of:
4-(3-chloro-phenyl)-3-(3-cyano-4-fluoro-benzenesulfonyl)-7-fluoro-quinoline;
7-chloro-3-(3-cyano-benzenesulfonyl)-4-(4-fluoro-phenyl)-quinoline;
4-(4-chloro-phenyl)-3-(3,4-difluoro-benzenesulfonyl)-7-fluoro-quinoline; and
4-(4-chloro-phenyl)-3-(3-cyano-5-fluoro-benzenesulfonyl)-7-fluoro-quinoline,
or a salt thereof.

17. A pharmaceutical formulation comprising a therapeutically effective amount of a compound selected from the group consisting of:
4-(3-chloro-phenyl)-3-(3-cyano-4-fluoro-benzenesulfonyl)-7-fluoro-quinoline;
7-chloro-3-(3-cyano-benzenesulfonyl)-4-(4-fluoro-phenyl)-quinoline;
4-(4-chloro-phenyl)-3-(3,4-difluoro-benzenesulfonyl)-7-fluoro-quinoline; and
4-(4-chloro-phenyl)-3-(3-cyano-5-fluoro-benzenesulfonyl)-7-fluoro-quinoline,
or a physiologically acceptable salt thereof, and one or more physiologically acceptable diluents, excipients or inert carriers.

* * * * *

UNITED STATES PATENT AND TRADEMARK OFFICE
CERTIFICATE OF CORRECTION

PATENT NO.        : 8,063,220 B2                                Page 1 of 1
APPLICATION NO.   : 12/144490
DATED             : November 22, 2011
INVENTOR(S)       : Janos Galambos It is certified that error appears in the above-identified patent and that said Letters Patent is hereby corrected as shown below:

First Page, Column 2, Line 9, please delete "4-quinolone" and insert -- 4-quinoline --, therefor.

Column 150, Line 52 (Claim 5), below "formula (III):" please insert -- $Ar_1\text{-}S^-M^+$ --.

Column 154, Lines 19-20 (Claim 8), after "phenyl" please delete "or an optionally substituted heteroaryl".

Signed and Sealed this
Twenty-seventh Day of March, 2012

David J. Kappos
*Director of the United States Patent and Trademark Office*